United States Patent
Osl et al.

(10) Patent No.: US 11,944,691 B2
(45) Date of Patent: Apr. 2, 2024

(54) CXCR4-TARGETED DIAGNOSTIC AND THERAPEUTIC AGENTS WITH REDUCED SPECIES SELECTIVITY

(71) Applicant: TECHNISCHE UNIVERSITÄT MÜNCHEN, Munich (DE)

(72) Inventors: Theresa Osl, Garching bei München (DE); Hans-Jürgen Wester, Ilmmünster (DE); Margret Schottelius, Munich (DE); Tobias Kapp, Lörrach (DE); Horst Kessler, Garching bei München (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 0 days.

(21) Appl. No.: 17/275,880

(22) PCT Filed: Sep. 11, 2019

(86) PCT No.: PCT/EP2019/074196
§ 371 (c)(1),
(2) Date: Mar. 12, 2021

(87) PCT Pub. No.: WO2020/053256
PCT Pub. Date: Mar. 19, 2020

(65) Prior Publication Data
US 2022/0040339 A1 Feb. 10, 2022

(30) Foreign Application Priority Data
Sep. 12, 2018 (EP) ..................... 18194124

(51) Int. Cl.
*A61K 51/08* (2006.01)
(52) U.S. Cl.
CPC .................. *A61K 51/088* (2013.01)
(58) Field of Classification Search
CPC ...... A61K 51/00; A61K 51/08; A61K 51/088; A61P 43/00; A61P 35/00; C07K 7/64
USPC .......... 424/1.11, 1.65, 1.69, 1.81, 1.85, 1.89, 424/9.1, 9.2, 9.3, 9.4, 9.5, 9.6, 1.77; 534/7, 10–16
See application file for complete search history.

(56) References Cited

U.S. PATENT DOCUMENTS

| | | | | |
|---|---|---|---|---|
| 8,614,290 B2* | 12/2013 | Wester | .................. | A61K 51/08 435/7.1 |
| 9,266,924 B2* | 2/2016 | Demmer | ................. | C07K 7/64 |
| 10,919,938 B2* | 2/2021 | Wester | .................. | A61P 35/00 |

FOREIGN PATENT DOCUMENTS

| | | | |
|---|---|---|---|
| WO | WO 2008/083312 | 7/2008 | |
| WO | WO 2008/150689 | 12/2008 | |
| WO | WO 2011/131731 | 10/2011 | |
| WO | WO-2011131731 A1 * | 10/2011 | ............. A61K 51/08 |
| WO | WO 2015/185162 | 12/2015 | |

OTHER PUBLICATIONS

Lee et al., Peptide Science, vol. 110, No. 3, e24063/1-e24063/10 (Year: 2018).*
Benham et al., "C-terminal residue optimization and fragemtn merging: discovery of a potent peptide-hybrid inhibitor of Dengue protease," *ACS Medicinal Chemistry Letters*, 5(9):1037-1042, 2014.
Demmer et al., "A comformationally frozen peptoid boosts CXCR4 affinity and anti-HIV activity," *Angewandte Chemie International Edition*, 51(32):8110-8113, 2012.
Osl, "Development of cyclic pentapeptide ligands for chemokind receptor targeting," retrieved from http://mediatum.ub.tum.de/doc/1342124/1342124.pdf, 2018.
PCT International Search Report and Written Opinion issued in International Application No. PCT/EP2019/074196, dated Dec. 17, 2019.
PCT International Search Report and Written Opinion issued in International Application No. PCT/EP2019/074195, dated Oct. 9, 2019.
Schottelius et al., "[$^{177}$Lu]pentixather: Comprehensive Preclinical Characterization of a First CXCR4-directed Endoradiotherapeutic Agent," *Theranostics*, 7(9):2350-2362, 2017.

* cited by examiner

Primary Examiner — D. L. Jones
(74) Attorney, Agent, or Firm — Parker Highlander PLLC

(57) ABSTRACT

The present disclosure relates to imaging and endoradiotherapy of diseases involving chemokine receptor 4 (CXCR4). Provided are compounds which bind or inhibit hCXCR4 and mCXCR4 and furthermore carry at least one moiety which is amenable to labeling. Provided are also medical uses of such compounds.

10 Claims, 13 Drawing Sheets

FC131 (1)

CPCR4.2

CPCR4.3 (2)

3

CXCR4-TARGETED DIAGNOSTIC AND THERAPEUTIC AGENTS WITH REDUCED SPECIES SELECTIVITY

This application is a national phase application under 35 U.S.C. § 371 of International Application No. PCT/EP2019/074196, filed Sep. 11, 2019, which claims the benefit of EP 18194124.6, filed Sep. 12, 2018, the entire contents of each of which are hereby incorporated by reference.

The present disclosure relates to imaging and endoradiotherapy of diseases involving chemokine receptor 4 (CXCR4), Provided are compounds which bind or inhibit CXCR4 and furthermore carry at least one moiety which is amenable to labeling. Provided are also medical uses of such compounds.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Binding of the only endogenous ligand CXCL12 (formerly termed SDF-1α) to its cognate receptor, the chemokine receptor 4 (CXCR4) [1], activates the downstream protein kinase B (AKT)/mitogen-activated protein kinases (MAPK) signaling pathway, which leads to the alteration of gene expression, actin polymerization, cell skeleton rearrangement and cell migration. The physiological functions of the CXCL12/CXCR4 axis include embryogenesis (regulation of embryonic stem cell migration and positioning), immune response (leucocyte trafficking to sites of inflammation), embryo implantation (positioning of blastocysts in maternal endometrium), hematopoiesis (homing and differentiation of hematopoietic stem/progenitor cells in the bone marrow), brain development and neo-angiogenesis [2-6], Consequently, genetic defects displayed in CXCL12 and CXCR4 gene-deleted mice exhibit identical, lethal phenotypes with severely impaired hematopoiesis and CNS development [7].

The CXCR4 receptor has been found to be involved in a variety of diseases. For example, it mediates HIV-1 entry into T-cells as a co-receptor where it was first identified [3], Furthermore, in rheumatoid arthritis (RA) CXCR4 expressing CD4+ memory T cells accumulate in the inflamed synovium because of the high local CXCL12 concentration [8]. In the pathogenesis of atherosclerosis, chronic inflammation of the arterial wall characterized by chemokine-mediated influx of leukocytes plays a central role [9], The cytokine macrophage migration inhibitory factor (MIF) is a unique pro-inflammatory regulator of many acute and chronic inflammatory diseases that contribute to lesion progression and plaque inflammation. These chemokine-like functions are mediated through interaction of MIF with the chemokine receptors CXCR2 and CXCR4, thus suggesting a central role of CXCR4 in atherosclerotic plaque development, vascular remodeling after injury, in atherosclerosis plaque destabilization and aneurysm formation [10].

In addition, CXCR4 is involved in B-cell trafficking and tissue localization in chronic leukemia patients [11] as well as the regulation of organ specific metastasis in different breast cancer models [12]. Furthermore, pronounced CXCR4 overexpression has been detected in more than 20 human tumor types, including hematopoietic malignancies, brain neoplasm, gastrointestinal cancer and other cancer types [2, 13-14]. A method for the early assessment of the metastatic potential and metastatic spread of tumors therefore represents a valuable tool for therapy planning, monitoring and control, since cancer metastasis is one of the critical factors affecting the life expectancy of patients.

Given the undisputed relevance of CXCR4 as a diagnostic and therapeutic molecular target, a multitude of CXCR4 targeted peptidic and non-peptidic antagonists have been developed during the last decade. Amongst them, the bicyclam AMD3100 (plerixafor/Mozobil) is the only compound that has been approved by the FDA (in 2008) for the mobilization of stem cells and for the treatment of hematological and other cancers [7, 15-17], In preclinical studies using mouse models of a variety of human hematological as well as solid cancers, antitumor therapies using either alternative small molecule CXCR4 antagonists such as AMD3465 [18-19] or MSX-122 [20], peptidic CXCL12 derivatives (CTCE-9908 [21], BKT-140 [22-24], POL-5551 [25-27]) or anti-CXCR4-antibodies [28-29] were shown to consistently lead to prolonged overall survival, primarily by effectively preventing distant organ metastasis [30]. Another potent CXCR4 antagonist, LY2510924 (cyclo[Phe-Tyr-Lys(iPr)-D-Arg-2-Nal-Gly-D-Glu]-Lys(iPr)—NH2) [31-32], exhibited high antitumor activities in solid tumor and breast cancer metastatic models and is currently evaluated in phase II clinical studies (NCT01391130 and NCT1439568). Lactam-cyclized heptapeptides were reported to be potent CXCR4 antagonists with high efficiency in the treatment of cancers, rheumatoid arthritis, pulmonary fibrosis, and HIV infection (WO 2008150689 A1). Recently, disulfide-bridged cyclic heptapeptide antagonists (WO/2011/092575A1) were shown to exhibit high in vivo stability [33-34], to efficiently inhibit lung metastasis in a melanoma model [35] and to reduce the metastatic potential of HOC and osteosarcoma in a mouse model [36], A modified analog (R29, Ac-Arg-Ala-[D-Cys-Arg-Phe-His-Pen]-COOH) efficiently reverts the suppressive activity of T-regulatory cells in renal cancer [37].

Amongst these CXCR4 targeted antagonists, T-140 based peptides were the first compounds to be employed for molecular imaging of CXCR4-expression in vivo; different analogs, either radiolabeled with $^{18}$F or $^{68}$Ga or conjugated with fluorescent dyes as well as corresponding bimodal probes have been employed for the non-invasive detection and visualization of CXCR4-expressing tissues using positron emission tomography (PET), optical or SPECT imaging [38-45].

Furthermore, cyclic pentapeptides based on the N-terminal sequence of CXCL12 [46] or, more importantly, the downsized T-140 binding sequence cyclo(Gly-Nal-Arg-Arg-D-Tyr) (FC-131) [47] have been extensively evaluated. Detailed structure activity relationship (SAR) studies have highlighted the relevance of single amino acid residues and their stereochemistry as well as of amide bond methylation [48-53] for optimal CXCR4 affinity and antagonistic activity. Based on these findings and own SAR studies, our group has developed a first pentapeptide-based CXCR4-targeted molecular imaging agent, [$^{68}$Ga]pentixafor. Substitution of Arg$^2$ (in FC131) by D-Ornithine and N-methylation of D-Orn led to the CPCR4-scaffold (cyclo(D-Tyr$^1$-D-[NMe]Orn$^2$-Arg$^3$-Nal$^4$-Gly$^5$)), which showed excellent binding affinity towards CXCR4 [54]. Further functionalization of the Orn$^2$ sidechain with a suitable linker (4-aminomethylbenzoic acid, AMBS) and a DOTA (1,4,7,10-tetraazacyclododecane-1,4,7,10-tetraacetic acid) chelator led to pentixafor (cyclo(D-Tyr$^1$-D-[NMe]Orn$^2$(AMBS-DOTA)-Arg$^3$-Nal$^4$-Gly$^5$), also termed CPCR4.2) [54-56]; WO2007/

096662, WO 2009/027706, WO 2011/131735). Its [68Ga]-labeled analog, [[68Ga]pentixafor [57] shows high affinity and selectivity for human CXCR4, rapid renal excretion and very low non-specific background accumulation and thus allows sensitive and high-contrast imaging of CXCR4 expressing tissues in vivo using PET. Besides its successful application in patients with lymphoma [58], multiple myeloma [59-61], AML [62], SCLC [63], glioblastoma [64] or other solid tumors [65], [[68Ga]pentixafor-PET has recently been shown to be a valuable tool for the in vivo detection of inflammatory processes e.g. after myocardial infarction [66-68] or stroke [69], in atherosclerosis [70-72] or other inflammatory diseases [73-74].

An alternative peptide backbone (cyclo(D-3-iodo-Tyr$^1$-D-[NMe]Orn$^2$-Arg$^3$-Nal$^4$-Gly$^5$)) was employed for the synthesis of a first CXCR4 targeted endoradiotherapeutic agent, namely pentixather (cyclo(D-3-iodo-Tyr$^1$-D-[NMe]Orn$^2$(AMBS-DOTA)-Arg$^3$-Nal$^4$-Gly$^5$) [75-76] (WO 2015/185162). First very promising results have been obtained using [[177Lu]- and [[90Y]pentixather for PRRT (peptide receptor targeted radionuclide therapy) in patients with multiple myeloma [77-78], and consequently a clinical trial further evaluating the [[68Ga]pentixafor/[[177Lu/90Y]pentixather based CXCR4 targeted theranostic concept has recently been initiated. Furthermore, ongoing preclinical studies are directed towards establishing the potential of alpha-therapy in disseminated micrometastatic hematological cancers using [[213Bi/225Ac]pentixather.

While having undisputed clinical potential for CXCR4-targeted theranostics, however, both [[68Ga]pentixafor and [[177Lu/90Y]pentixather display pronounced selectivity for the human CXCR4 (hCXCR4) receptor and show virtually no affinity to the murine receptor (mCXCR4). To date, this precludes their use as preclinical tools for the investigation of CXCR4-related pathologies such as carcinogenesis or inflammatory diseases in mouse models. Recently, an alternative pentapeptide scaffold with a modified N-alkylation pattern compared to pentixafor/pentixather has been introduced [79], and peptides based on this backbone were shown to have hCXCR4 affinities in the low nanomolar to sub-nanomolar range. Recent studies have demonstrated that, surprisingly, the analog with the highest hCXCR4 affinity (cyclo(D-Tyr$^1$-D-[N-hexyl-6-guanidino]D-Ala$^2$-Arg$^3$-Nal$^4$-Gly$^5$); CPCR4.3) also binds with equally high affinity to mCXCR4. Based on these results, radioiodinated CPCR4.3 has been very recently shown to sensitively detect CXCR4-expressing immune cells in a mouse model of esophageal cancer [80].

Unfortunately, however, radioiodinated CPCR4.3 is not well suited for imaging purposes beyond autoradiography studies; due to its lipophilicity, the peptide shows suboptimal pharmacokinetics characterized by significant hepatobiliary clearance, precluding its application for in vivo imaging studies. The implementation of alternative labelling strategies such as radiometallation via a DOTA chelator (as in pentixafor/pentixather), however, requires the identification of suitable attachment sites for further structural modification within the peptide sequence.

Based on this hypothesis, the present invention describes the design of novel CPCR4.3 analogs functionalized at the guanidino-group of the 6-guanidino-hexyl-sidechain on D-Ala$^2$, either via acylation or alkylation. It summarizes approaches for the identification of a suitable linker moiety between the peptide core and the radiolabel/signaling unit and describes the resulting design of novel CXCR4-targeted probes with high m/hCXCR4 affinity (reduced species selectivity) labelled with a broad palette of radionuclides and/or fluorescent dyes for molecular imaging and therapeutic applications.

Accordingly, in a first aspect, the present invention relates to a compound of the following formula (I)

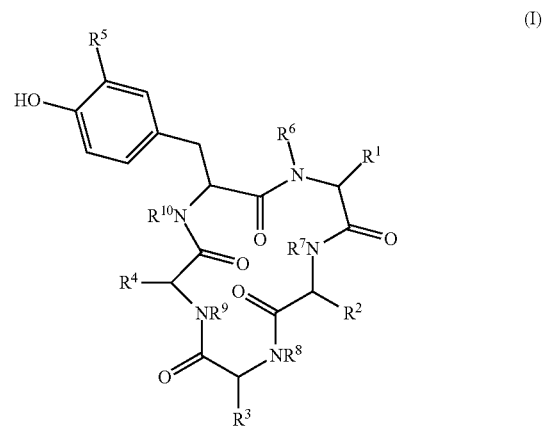

or a pharmaceutically acceptable salt thereof, wherein:
$R^1$ is alkyl, preferably C1-C6 alkyl, more preferably methyl;
$R^2$ is H or alkyl, which alkyl may be unsubstituted or substituted with at least one substituent selected from —NH$_2$, —NH—C(=NH)—NH$_2$, —C(O)NH$_2$, —C(O)OH, —OH, —SH, —SCH$_3$ and a 5 to 10-membered carbocycle or 5 to 10-membered heterocycle containing oxygen, nitrogen or sulfur as heteroatom(s), wherein the alkyl is preferably C1-C6 alkyl;
$R^3$ is H or alkyl, which alkyl may be unsubstituted or substituted with at least one substituent selected from —NH$_2$, —NH—C(=NH)—NH$_2$, —C(O)NH$_2$, —C(O)OH, —OH, —SH, —SCH$_3$ and a 5 to 10-membered carbocycle or 5 to 10-membered heterocycle containing oxygen, nitrogen or sulfur as heteroatom(s), wherein the alkyl is preferably C1-C6 alkyl;
$R^4$ is H or alkyl, which alkyl may be unsubstituted or substituted with at least one substituent selected from —NH$_2$, —NH—C(=NH)—NH$_2$, —C(O)NH$_2$, —C(O)OH, —OH, —SH, —SCH$_3$, —SR$^4$, —SR$^{11}$, and a 5 to 10-membered carbocycle or 5 to 10-membered heterocycle containing oxygen, nitrogen or sulfur as heteroatom(s), wherein the alkyl is preferably C1-C6 alkyl;
$R^5$ is H or I;
$R^6$ is alkyl substituted with at least one substituent selected from —NH$_2$, —NH—C(=NH)—NH$_2$, —NH—R$^6$, —NH—C(=NH)—NH—R$^B$, —NH—C(=NH)—NH—R$^{14}$, and —NH—C(=NH)—NH—C(=O)—R$^{15}$, wherein the alkyl is preferably C1-C8 alkyl,
$R^7$ to $R^{10}$ are each independently H or alkyl; preferably H or C1-C6 alkyl; and more preferably H;
$R^{11}$ is selected from —(CH$_2$)—C(=O)—NH—R$^{12}$—NH—C(=O)—CH$_3$ and —(CH$_2$)—C(=O)—NH—(CH$_2$)$_r$—R$^{13}$—(CH$_2$)$_s$—NH—C(=O)—CH$_3$, wherein R$^{12}$ is a C2-C10 alkanediyl group, preferably a C3-C6 alkanediyl group, which alkanediyl group may be substituted by a group —C(=O)—NH$_2$, R$^{13}$ is a phenylene group, preferably a 1,3-phenylene group, and r and s are independently integers selected from 0, 1 or 2, and are preferably both 1;

$R^{14}$ and $R^{15}$ are independently C1-C10 alkyl, preferably C2-C6 alkyl, which alkyl may be substituted by at least one substituent selected from —NH—C(=O)—CH$_3$ and —C≡CH;

$R^A$ is a group which comprises at least one selected from:
(i) a chelating moiety,
(ii) a chelate formed by a chelating moiety (i) with a chelated radioactive or non-radioactive cation,
(iii) a moiety carrying a covalently bound radioisotope, or a precursor suitable to be labeled with such a radioisotope,
(iv) a phosphonate moiety, and
(v) a fluorescent label, such as a quantum dot or fluorescent dye; and $R^B$ is a group which comprises at least one selected from:
(i) a chelating moiety,
(ii) a chelate formed by a chelating moiety with a chelated radioactive or non-radioactive cation,
(iii) a group carrying a covalently bound radioisotope, or a precursor suitable to be labeled with such a radioisotope,
(iv) a phosphonate moiety, and
(v) a fluorescent label, such as a quantum dot or fluorescent dye, and $R^B$ may further comprise a group of formula (II)

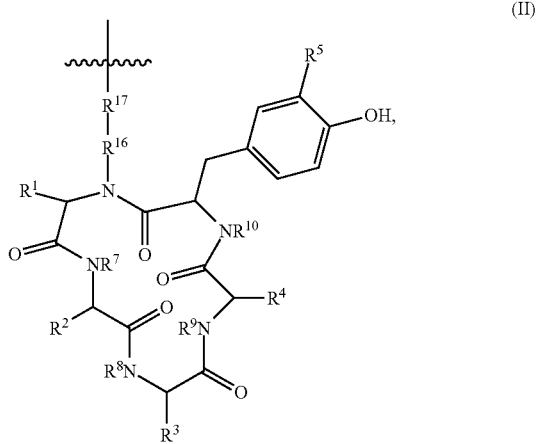

(II)

which is bound to the remainder of the compound with the bond marked with ⌇⌇⌇, wherein $R^1$ to $R^5$ and $R^7$ to $R^{10}$ are as defined above, and wherein $R^{16}$ is an alkanediyl group, preferably a C1-C6 alkanediyl group, and $R^{17}$ is selected from —NH— and —NH—C(=NH)—NH—; and wherein said compound of formula (I) comprises at least one substituent selected from —S—$R^A$, —NH—$R^6$ and —NH—C(=NH)—NH—$R^B$.

Compounds in accordance with the first aspect of the present invention deviate from CXCR4 binders known in the art with respect to at least one feature. To explain further, one of these features is that the amide nitrogen bearing $R^6$ is substituted in compounds of the invention. More specifically, it is substituted with an alkyl group which bears a substituent selected from amino and guanidinium groups, which amino and guanidinium groups may be further substituted in turn. These further substituents include the moiety $R^B$. Embodiments of $R^B$ include a chelating moiety as well as other labels or groups amenable to labeling. In other words, not only is the mentioned nitrogen atom bearing $R^6$ substituted, but furthermore by such substituting an anchor point has been introduced in the molecule which anchor point provides for further options of the derivatization. Preferred derivatizations are further detailed below and include the introduction of moieties useful for diagnostic molecular imaging and endoradiotherapy. The present invention demonstrates that such derivatizations are possible without negatively interfering with target binding.

A further difference from CXCR4 binders known in the art is that group $R^1$ is not the side chain of ornithin, but instead an alkyl group, preferably methyl.

The introduction of the above defined substituent $R^6$ alongside with the altered alkylation pattern at $R^1$, also referred to as an "alkyl shift", provides for distinct advantages, said advantages including—apart from the option of introducing the mentioned labels or moieties amenable to labeling at $R^6$—
a significant increase of the affinity for the target human CXCR4 (hCXCR4), and
a substantial reduction in the species selectivity of ligand binding, leading to almost equally high affinities of the peptides modified at $R^6$ for the human (hCXCR4) and mouse (mCXCR4) receptor.

As noted above, the present inventors aim at the provision of CXCR4 binding molecules for diagnostic molecular imaging and endoradiotherapy. Surprisingly, it has been discovered that there is one further site except $R^6$ which is amenable to functionalization with a signaling unit such as a radiolabel or fluorescent dye. Such second site is provided by embodiments of $R^4$. In particular, those embodiments where $R^4$ comprises $R^A$, use is made of $R^A$ as an anchor point for modifications, said modifications including, in analogy to $R^B$ discussed above, the introduction of radioactive labels, moieties amenable to radioactive labeling or other signaling units suitable for molecular imaging.

In accordance with the invention, at least one of $R^A$ and $R^B$ are present. Both of them may be present.

$R^1$ in formula (I) is alkyl, preferably linear alkyl. It is preferred that the alkyl group is a C1-C6 alkyl group, more preferably a C1 or C2 alkyl, and most preferably methyl.

$R^2$ in formula (I) is H or alkyl, which alkyl may be unsubstituted or substituted with at least one substituent selected from —NH$_2$, —NH—C(=NH)—NH$_2$, —C(O)NH$_2$, —C(O)OH, —OH, —SH, —SCH$_3$ and a 5 to 10-membered carbocycle or 5 to 10-membered heterocycle containing oxygen, nitrogen or sulfur as heteroatom(s). The alkyl is preferably a linear alkyl group. As regards the number of carbon atoms, it is preferred that the alkyl is C1-C6 alkyl, more preferably C2-C3 alkyl, and most preferably C3 alkyl. In terms of the substituent, it is preferred that $R^2$ is substituted with at least one group selected from —NH$_2$ and guandino (—NH—C(=NH)—NH$_2$), Particularly preferred as a group $R^2$ is a linear C3 alkyl group, substituted at its terminal C-atom (i.e. the C atom most remote from the point of attachment of $R^2$ in formula (I)) with one of —NH$_2$ and guandino (—NH—C(=NH)—NH$_2$). Most preferred is —CH$_2$—CH$_2$—CH$_2$—NH—C(=NH)—NH$_2$.

As will be understood by the skilled reader, any 5 to 10-membered carbocycle referred to herein may be formed by a single ring having a number of ring members falling within the defined range, or by fused rings (e.g. two fused rings) having a total number of ring members falling within the defined range. Likewise, any 5 to 10-membered heterocycle referred to herein may be formed by a single ring having a number of ring members falling within the defined range, or by fused rings (e.g. two fused rings) having a total number of ring members falling within the defined range.

$R^3$ in formula (I) is H or alkyl, which alkyl may be unsubstituted or substituted with at least one substituent selected from —$NH_2$, —NH—C(=NH)—$NH_2$, —C(O)$NH_2$, —C(O)OH, —OH, —SH, —$SCH_3$ and a 5 to 10-membered carbocycle or 5 to 10-membered heterocycle containing oxygen, nitrogen or sulfur as heteroatom(s). As regards the number of carbon atoms, it is preferred that the alkyl is C1-C6 alkyl, more preferably C1-C2 alkyl, and most preferably methyl. In terms of the substituent, it is preferred that $R^3$ is substituted with a 5 to 10-membered carbocycle, more preferably a phenyl or naphthyl group. Particularly preferred as a group $R^3$ is a methyl group substituted with one phenyl or one naphthyl group, and most preferred is a group —$CH_2$-naphthyl, such as —$CH_2$-(2-naphtyl), $R^4$ in formula (I) is H or alkyl, which alkyl may be unsubstituted or substituted with at least one substituent selected from —$NH_2$, —NH—C(=NH)—$NH_2$, —C(O)$NH_2$, —C(O)OH, —OH, —SH, —$SCH_3$, —$SR^A$, —$SR^{11}$, and a 5 to 10-membered carbocycle or 5 to 10-membered heterocycle containing oxygen, nitrogen or sulfur as heteroatom(s). The alkyl is preferably C1-C6 alkyl more preferably C1-C2 alkyl, and most preferably methyl. Generally preferred as $R^4$ are H and alkyl substituted with one substituent selected from —SH, —$SR^A$ and —$SR^{11}$. Particularly preferred as $R^4$ are H, —$CH_2$—SH, —$CH_2$—$SR^A$ and —$CH_2$—$SR^{11}$.

$R^{11}$ is selected from —($CH_2$)—C(=O)—NH—$R^{12}$—NH—C(=O)—$CH_3$ and
—($CH_2$)—C(=O)—NH—($CH_2$)$_r$—$R^{13}$—($CH_2$)$_s$—NH—C(=O)—$CH_3$. $R^{12}$ is a C2-C10 alkanediyl group, preferably a C3-C6 alkanediyl group, and more preferably a C4-C6 alkanediyl group. Preferably, the alkanediyl group is a linear group. The alkanediyl group may be substituted by a group —C(=O)—$NH_2$.
$R^{13}$ is a phenylene group, preferably a 1,3-phenylene group, and r and s are independently integers selected from 0, 1 or 2, and are preferably both 1;

$R^5$ in formula (I) is H or I, and is preferably H.

$R^6$ in formula (I) is alkyl substituted with at least one substituent selected from —$NH_2$, —NH—C(=NH)—$NH_2$, —NH—$R^B$, —NH—C(=NH)—NH—$R^B$, —NH—C(=NH)—NH—$R^{14}$, and —NH—C(=NH)—NH—C(=O)—$R^{15}$. The alkyl is preferably a linear alkyl group. As regards the number of carbon atoms, it is preferred that the alkyl is C1-C8 alkyl, more preferably C2-C6 alkyl, and most preferably C6 alkyl. In terms of the substituent, it is preferred that $R^6$ is substituted with one group selected from —NH—C(=NH)—$NH_2$, —NH—C(=NH)—NH—$R^B$, —NH—C(=NH)—NH—$R^{14}$, and —NH—C(=NH)—NH—C(=O)—$R^{15}$. Particularly preferred as a group $R^6$ is thus a linear C2-C6 alkyl, even more preferred a linear C6 alkyl, substituted at its terminal C-atom (i.e. the C atom most remote from the point of attachment of $R^6$ in formula (I)) with one group selected from —NH—C(=NH)—$NH_2$, —NH—C(=NH)—NH—$R^B$, —NH—C(=NH)—NH—$R^{14}$, and —NH—C(=NH)—NH—C(=O)—$R^{15}$.

$R^{14}$ and $R^{15}$ are independently C1-C10 alkyl, preferably C2-C6 alkyl. The alkyl group is preferably a linear alkyl group. The alkyl, preferably linear alkyl, may be substituted by at least one substituent selected from —NH—C(=O)—$CH_3$ and —C≡CH. Preferably, the alkyl group is a linear C1-C10 alkyl group, more preferably a linear C2-C6 alkyl group, which is unsubstituted or substituted at its terminal C-atom (i.e. the C atom most remote from the point of attachment of $R^{14}$ and $R^{15}$ in the above formulae) by one substituent selected from —NH—C(=O)—$CH_3$ and —C≡CH.

$R^7$ to $R^{10}$ in formula (I) are each independently H or alkyl; preferably H or C1-C6 alkyl; and are more preferably H.

In line with the above, it will be understood that the compound of formula (I) is preferably represented by the following formula (III):

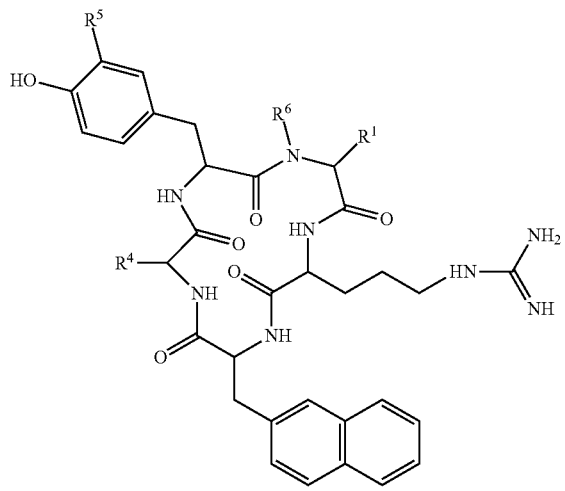

(III)

wherein $R^1$, $R^4$, $R^5$ and $R^6$ are defined as for formula (I), including their preferred meanings.

More preferably, the compound of formula (I) is represented by the following formula (IV):

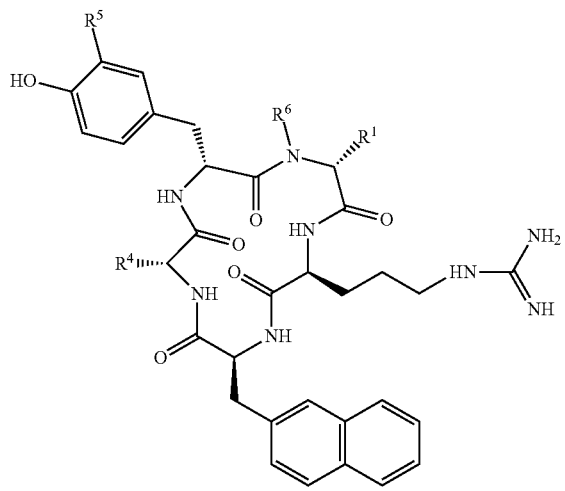

(IV)

wherein $R^1$, $R^4$, $R^5$ and $R^6$ are defined as for formula (I), including their preferred meanings.

As noted above, the compound of formula (I), or the preferred formulae (III) and (IV), comprises at least one substituent selected from —$SR^A$, —NH—$R^6$ and —NH—C(=NH)—NH—$R^B$. It is preferred that the compound of formula (I) or the preferred formulae (III) and (IV) comprises one substituent selected from —SR$^A$, —NH—R$^6$ and —NH—C(=NH)—NH—R$^B$. It is more preferred that the compound of formula (I) or the preferred formulae (III) and (IV) comprises one substituent selected from —SR$^A$ and —NH—C(=NH)—NH—R$^B$ (and thus no substituent —NH—R$^6$).

Thus, in one preferred embodiment, the compound of formula (I) or the preferred formulae (III) and (IV) comprises one of the substituents —NH—R$^6$ and —NH—C(=NH)—NH—R$^B$, more preferably —NH—C(=NH)—NH—R$^6$, and no substituent of formula —SR$^A$. In another preferred embodiment, the compound of formula (I) or the preferred formulae (III) and (IV) comprises one substituent of formula —SR$^A$, and none of the substituents —NH—R$^6$ and —NH—C(=NH)—NH—R$^B$.

In line with the above, a preferred subgroup of the compounds in accordance with the invention has the formula (Ia):

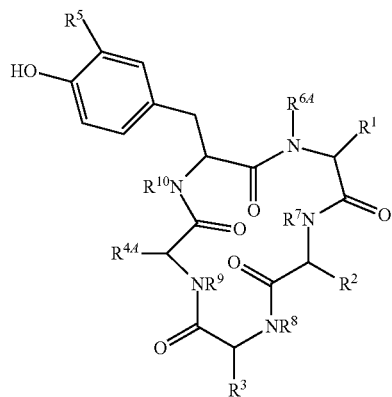

(Ia)

wherein R$^1$ to R$^3$, R$^5$ and R$^7$ to R$^{10}$ are defined as for formula (I), including their preferred meanings.

R$^{6A}$ is alkyl substituted with one substituent selected from —NH—R$^B$ and —NH—C(=NH)—NH—R$^B$, preferably substituted with —NH—C(=NH)—NH—R$^B$, wherein R$^B$ is defined as for formula (I), including its preferred meanings. The alkyl group is preferably a linear alkyl group. In terms of the number of carbon atoms, it is preferably C1-C8 alkyl, more preferably C2-C6 alkyl, and most preferably C6 alkyl. Particularly preferred as a group R$^{6A}$ is thus a linear C2-C6 alkyl, even more preferred a linear C6 alkyl, substituted at its terminal C-atom (i.e. the C atom most remote from the point of attachment of R$^6$ in formula (Ia)) with one group —NH—C(=NH)—NH—R$^B$. It is most preferred that R$^{6A}$ is -(linear C6 alkyl)-NH—C(=NH)—NH—R$^B$.

R$^{4A}$ is H or alkyl, which alkyl may be unsubstituted or substituted with one substituent selected from —NH$_2$, —NH—C(=NH)—NH$_2$, —C(O)NH$_2$, —C(O)OH, —OH, —SH, —SCH$_3$, —SR$^{11}$, and a 5 to 10-membered carbocycle or 5 to 10-membered heterocycle containing oxygen, nitrogen or sulfur as heteroatom(s), wherein R$^{11}$ is defined as for formula (I), including its preferred meanings. The alkyl is preferably C1-C6 alkyl, more preferably C1-C2 alkyl, and most preferably methyl. Generally preferred as R$^{4A}$ are H and alkyl substituted with one substituent selected from —SH, and —SR$^{11}$. Particularly preferred as R$^{4A}$ are H, —CH$_2$—SH, and —CH$_2$—SR$^{11}$. R$^{4A}$ is most preferably H. R$^{11}$ is defined as for formula (I), including its preferred meanings.

Another preferred subgroup of the compounds in accordance with the invention has the formula (Ib):

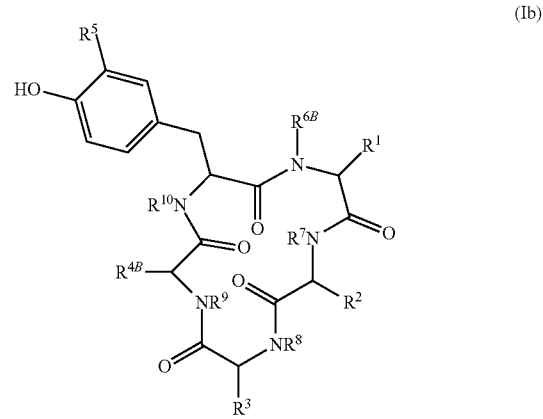

(Ib)

wherein R$^1$ to R$^3$, R$^5$ and R$^7$ to R$^{10}$ are defined as for formula (I), including their preferred meanings.

R$^{4B}$ is alkyl substituted with one substituent —SR$^A$ wherein R$^A$ is as defined for formula (I), including its preferred meanings. Preferably, the substituted alkyl is a C1-C6 alkyl, more preferably a C1 or C2 alkyl, and most preferred is methyl. Thus, it is particularly preferred that R$^{4B}$ is —CH$_2$—SR$^A$.

R$^{6B}$ is alkyl substituted with one substituent selected from —NH$_2$, —NH—C(=NH)—NH$_2$, —NH—C(=NH)—NH—R$^{14}$, and —NH—C(=NH)—NH—C(=O)—R$^{15}$, wherein R$^{14}$ and R$^{15}$ are defined as for formula (I), including their preferred embodiments. The alkyl is preferably a linear alkyl group. In terms of the number of carbon atoms, it is preferably C1-C8 alkyl, more preferably C2-C6 alkyl, and most preferably C6 alkyl. Particularly preferred as a group R$^{6B}$ is thus a linear C2-C6 alkyl, even more preferred a linear C6 alkyl, substituted at its terminal C-atom (i.e. the C atom most remote from the point of attachment of R$^{6B}$ in formula (Ib)) with one group —NH—C(=NH)—NH$_2$. Most preferred is that R$^{6B}$ is -(linear C6 alkyl)-NH—C(=NH)—NH$_2$. R$^{14}$ and R$^{15}$ are as defined for formula (I), including their preferred meanings.

In line with the above, it is preferred that the compound of formula (Ia) is a compound of formula (IIIa):

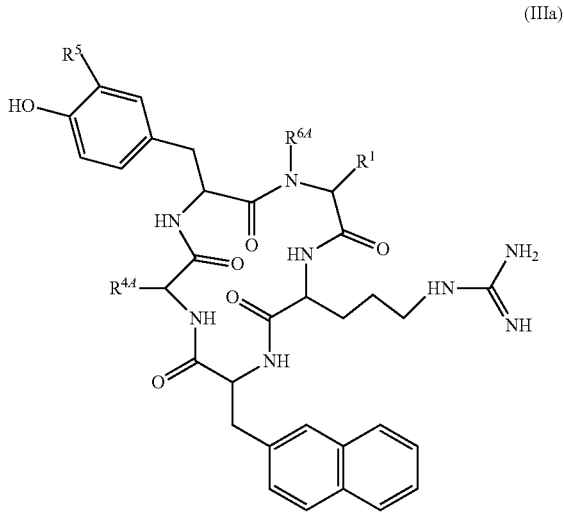

(IIIa)

wherein $R^1$, $R^{4A}$, $R^{6A}$ and $R^5$ are defined as for formula (I) and (Ia), respectively, including their preferred meanings. It is even further preferred that the compound of formula (Ia) is a compound of formula (IVa):

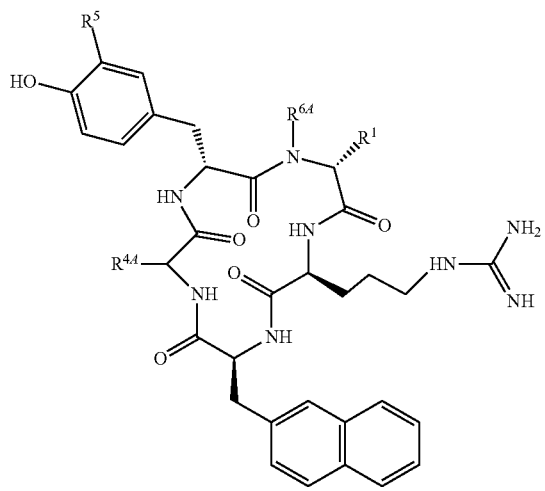

(IVa)

wherein $R^1$, $R^{4A}$, $R^{6A}$ and $R^5$ are defined as for formula (I) and (Ia), respectively, including their preferred meanings.

Similarly, it is preferred that the compound of formula (Ib) is a compound of formula (IIIb):

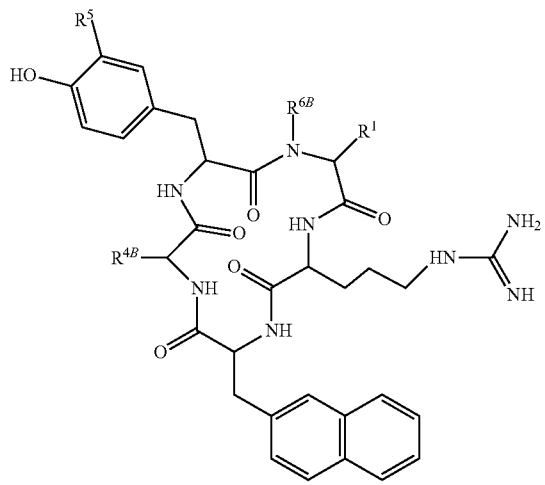

(IIIb)

wherein $R^1$, $R^{4B}$, $R^{6B}$ and $R^5$ are defined as for formula (I) or (Ib), respectively, including their preferred meanings. It is even further preferred that the compound of formula (Ib) is a compound of formula (IVb):

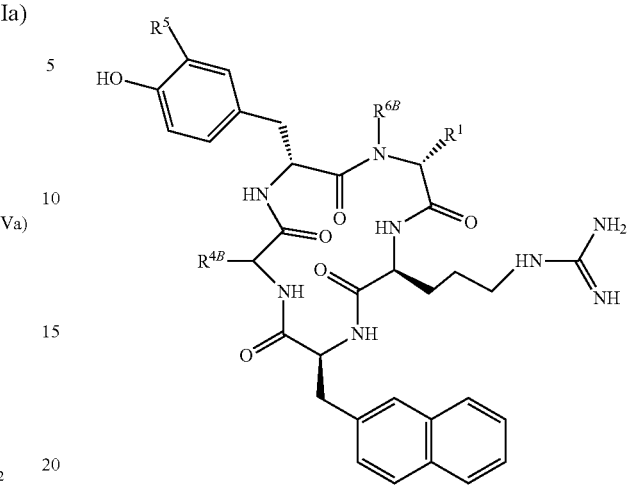

(IVb)

wherein $R^1$, $R^{4B}$, $R^{6B}$ and $R^5$ are defined as for formula (I) or (Ib), respectively, including their preferred meanings.

In formula (I) and the preferred formulae (Ia), (Ib), (III), (IIIa), (IIIb), (IV), (IVa) and (IVb), $R^4$ is a group which comprises at least one selected from:
  (i) a chelating moiety,
  (ii) a chelate formed by a chelating moiety (i) with a chelated radioactive or non-radioactive cation,
  (iii) a moiety carrying a covalently bound radioisotope, or a precursor suitable to be labeled with such a radioisotope,
  (iv) a phosphonate moiety, and
  (v) a fluorescent label, such as a quantum dot or fluorescent dye.

Typically, $R^4$ comprises one of (i) to (v), i.e. it is not necessary that two or more of (i) to (v) are present in one compound in accordance with the invention. Among the moieties (i) to (v), preference is given to (i) and (ii). Thus, it is particularly preferred that $R^4$ comprises one of (i) and (ii).

As will be understood by the skilled reader, the above definition, according to which $R^4$ comprises at least one of the above (i) to (v) encompasses the case that $R^4$ comprises a further moiety or further moieties together with the at least one of (i) to (v). In accordance with a preferred example, $R^4$ may comprise, in addition to the at least one moiety of the above (i) to (v), a linking group which attaches the at least one moiety of (i) to (v) to the remainder of the compound. The linking group may be a divalent linking group which attaches one of (i) to (v) to the remainder of the compound, or a branched linking group which allows two or more of (i) to (v) to be attached to the remainder of the compound. Preferably, $R^4$ comprises a divalent linking group.

Thus, it is further preferred that $R^4$ is a group of the formula -$L^{41}$-$R^{41}$, wherein $L^{41}$ is a divalent linking group and $R^{41}$ is or comprises one group selected from: (i) a chelating moiety, (ii) a chelate formed by a chelating moiety (i) with a chelated radioactive or non-radioactive cation, (iii) a moiety carrying a covalently bound radioisotope, or a precursor suitable to be labeled with such a radioisotope, (iv) a phosphonate moiety, and (v) a fluorescent label, such as a quantum dot or fluorescent dye. Among these, (i) and (ii) are more preferred.

It is particularly preferred that -L$^{A1}$-R$^{A1}$ is selected from the groups of formulae (Va) and (Vb):

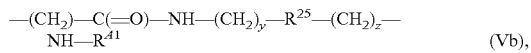

wherein R$^{24}$ is a C2-C10 alkanediyl group, preferably a C3-C6 alkanediyl group, which alkanediyl group is preferably linear and may be substituted by a group —C(=O)—NH$_2$, R$^{25}$ is a phenylene group, preferably a 1,3-phenylene group, and y and z are independently integers selected from 0, 1 or 2, and are preferably both 1. R$^{A1}$ is as defined above, including its preferred meanings. Among these, it is particularly preferred that -L$^{A1}$-R$^{A1}$ is a group of formula (Vb).

The chelating moiety of (i) and (ii), both in the context of the definition of R$^{A}$ and R$^{A1}$, is suitable to form a chelate with a radioactive or non-radioactive cation. Suitable chelating moieties for diverse cations are well known in the art, and can be used in the context of the present invention.

Preferably, the chelating moiety comprises at least one of
a macrocyclic ring structure with 8 to 20 ring atoms of which 2 or more, preferably 3 or more, are selected from oxygen atoms, sulfur atoms and nitrogen atoms; and
an acyclic, open chain chelating structure with 8 to 20 main chain atoms of which 2 or more, preferably 3 or more are heteroatoms selected from oxygen atoms, sulfur atoms and nitrogen atoms.

A preferred example for the chelating moiety is a residue of a chelating agent such as bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicyclo[6.6.2]hexadecane (DO2A), 1,4,7,10-tetraazacyclododecane-N,N',N'',N'''-tetraacetic acid (DOTA), α-(2-carboxyethyl)-1,4,7,10-tetraazacyclododecane-1,4,7, 1D-tetraacetic acid or 2-[1,4,7,10-tetraazacyclododecane-4,7,10-triacetic acid]-pentanedioic acid (DOTAGA), N,N'-dipyridoxylethylendiamine-N,N'-diacetate-5,5'-bis(phosphate) (DPDP), diethylenetriaminepentaacetic acid (DTPA), ethylenediamine-N,N'-tetraacetic acid (EDTA), ethyleneglycol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecane-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2]hexadecane (TE2A), 1,4,8,11-tetraazacyclododecane-1,4,8,11-tetraacetic acid (TETA), terpyridin-bis(methyleneamintetraacetic acid (TMT), 1,4,7,10-tetraazacyclotridecan-N,N',N'',N'''-tetraacetic acid (TRITA), triethylenetetraaminehexaacetic acid (TTHA), N,N'-bis[(6-carboxy-2-pyridyl)methyl]-4,13-diaza-18-crown-6 (H$_2$macropa), and 4-amino-4-{2-[(3-hydroxy-1,6-dimethyl-4-oxo-1,4-dihydro-pyridin-2-ylmethyl)-carbamoyl]-ethyl} heptanedioic acid bis-[(3-hydroxy-1,6-dimethyl-4-oxo-1,4-dihydro-pyridin-2-ylmethyl)-amide] (THP), which residue is obtainable by covalently binding a carboxyl group contained in the chelating agent to the remainder of the compound via an ester or an amide bond, preferably an amide bond. For example, in formulae (Va) and (Vb), an amide bond can be conveniently formed directly from a carboxyl group contained in the above exemplary chelating agents and the nitrogen atom to which R$^{A}$ or R$^{A1}$, respectively, is attached in these formulae.

In a more preferred example, the chelating moiety of (i) or (ii) in the context of the definition of R$^{A}$ or R$^{A1}$ is a residue of a chelating agent selected from DOTA and DOTAGA, still more preferably a residue obtainable by forming an amide bond from a carboxyl group contained in DOTA and DOTAGA, and the nitrogen atom to which R$^{A1}$ is attached in formulae (Va) and (Vb).

Exemplary radioactive cations that are optionally chelated by the chelating moiety in accordance with (ii), both in the context of the definition of R$^{A}$ and R$^{A1}$ are selected from the cations of $^{44}$Sc, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{89}$Zr, $^{90}$Y, $^{89}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At, $^{212}$Bi, $^{213}$Bi, $^{223}$Ra, $^{225}$Ac, and $^{227}$Th, or a cationic molecule comprising $^{18}$F, such as $^{18}$F—[AlF]$^{2+}$.

Preferred chelated cations are selected from the cations of $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, and $^{227}$Th, or a cationic molecule comprising $^{18}$F. Even further preferred are cations of $^{68}$Ga, $^{90}$Y, $^{177}$Lu, $^{212}$Bi, and $^{213}$Bi.

Moieties (iii) carrying a covalently bound radioisotope, preferably $^{18}$F-fluoride, or precursors suitable to be labeled with such radioisotope as referred to in the definition of R$^{A}$ and R$^{A1}$ can be used as known in the art. As examples of such a precursor, reference can be made to a group of formula —N$^{+}$(CH$_3$)$_2$—CH$_2$—BF$_3^{-}$ and to a group of the formula —Ar—SiF(C(CH$_3$)$_3$)$_2$, wherein Ar is a divalent aromatic group, preferably a phenylene group. As will be appreciated by the skilled reader, such a group of the formula —Ar—SiF(C(CH$_3$)$_3$)$_2$ can be conveniently bound to the remainder of the compounds in accordance with the invention by a functional group which may be attached to Ar at the open valence as indicated in the formula, and which is suitable for covalent coupling of the group —Ar—SiF(C(CH$_3$)$_3$)$_2$. For example, reference can be made to an amide bond or an ester bond which can be formed e.g. if the group —Ar—SiF(C(CH$_3$)$_3$)$_2$ is provided as a part of a benzoic acid derivative of the formula —C(O)—C6H4-SiF(C(CH$_3$)$_3$)$_2$.

Phosphonate moieties (iv), i.e. moieties comprising the structure —P(=O)(OH)$_2$ or salts thereof as referred to in the definition of R$^{A}$ and R$^{A1}$ can also be used as known in the art.

As a fluorescent label (v) as referred to in the definition of R$^{A}$ and R$^{A1}$, a fluorescent dye, such as Cy5 or Cy7, or a quantum dot may be used.

In formula (I) and the preferred formulae (Ia), (Ib), (III), (IIIa), (IIIb), (IV), (IVa) and (IVb), R$^{B}$ is a group which comprises at least one selected from:
(i) a chelating moiety,
(ii) a chelate formed by a chelating moiety with a chelated radioactive or non-radioactive cation,
(iii) a group carrying a covalently bound radioisotope, or a precursor suitable to be labeled with such a radioisotope,
(iv) a phosphonate moiety, and
(v) a fluorescent label, such as a quantum dot or fluorescent dye, and $R^B$ may further comprise a group of formula (II)

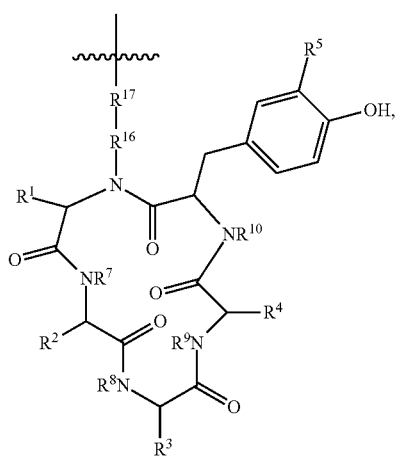

(II)

which is bound to the remainder of the compound with the bond marked with ⁓⁓⁓, wherein $R^1$ to $R^5$ and $R^7$ to $R^{10}$ are as defined for formula (I) including their preferred meanings, and wherein $R^{16}$ is an alkanediyl group, preferably a C1-C6 alkanediyl group, and $R^{17}$ is selected from —NH— and —NH—C(=NH)—NH—;

Typically, $R^B$ comprises one of (i) to (v), i.e. it is not necessary that two or more of (i) to (v) are present in one compound in accordance with the invention.

As will be understood by the skilled reader, the above definition, according to which $R^B$ comprises at least one of the above (i) to (v) encompasses the case that $R^B$ comprises a further moiety or further moieties together with the at least one of (i) to (v). In accordance with a preferred example, $R^B$ may comprise, in addition to the at least one moiety of the above (i) to (v), a linking group which attaches the at least one moiety of (i) to (v) to the remainder of the compound. The linking group may be a divalent linking group which attaches one of (i) to (v) to the remainder of the compound, or a branched linking group which allows two or more of (i) to (v) to be attached to the remainder of the compound. Preferably, $R^B$ comprises a divalent linking group.

Thus, it is further preferred that $R^B$ is a group of the formula -$L^{B1}$-$R^{B1}$, wherein $L^{B1}$ is a divalent linking group, and $R^{B1}$ is or comprises one group selected from (i) a chelating moiety, (ii) a chelate formed by a chelating moiety (i) with a chelated radioactive or non-radioactive cation, (iii) a moiety carrying a covalently bound radioisotope, or a precursor suitable to be labeled with such a radioisotope, (iv) a phosphonate moiety, and (v) a fluorescent label, such as a quantum dot or fluorescent dye. Moreover, $R^{B1}$ may further comprise a group of formula (II) as defined above.

It is particularly preferred that $L^{B1}$-$R^{B1}$ is selected from the groups of formulae (VIa) to (VIf):

—$R^{18}$—NH—$R^{B1}$ (VIa),

—$R^{18}$—NH—(C(=O)—$R^{19}$—NH)$_u$—$R^{B1}$ (VIb),

—$R^{18}$—NH—(C(=O)—$R^{20}$—NH)$_v$—$R^{B1}$ (VIc),

—C(=O)—$R^{21}$—NH—$R^{b1}$ (VId),

—C(=O)—$R^{21}$—NH—(C(=O)—$R^{22}$—NH)$_w$—$R^{b1}$ (VIe),

—C(=O)—$R^{21}$—NH—(C(=O)—$R^{23}$—NH)$_x$—$R^{B1}$ (VIf), wherein:
$R^{18}$ is C1-C10 alkanediyl, preferably linear alkanediyl, more preferably linear C2-C6 alkanediyl, and most preferably linear C6 alkanediyl,
$R^{19}$ is C1-C10 alkanediyl, preferably linear alkanediyl, more preferably linear C2-C6 alkanediyl, u is 1, 2 or 3, preferably 1 or 2,
$R^{20}$ is an oligoether moiety, preferably a linear oligoether moiety, more preferably a linear oligoether moiety having 5 to 10 carbon atoms and 2 or 3 oxygen atoms providing the ether bonds, v is 1, 2 or 3, preferably 1 or 2,
$R^{21}$ is C1-C10 alkanediyl, preferably linear alkanediyl, more preferably linear C2-C6 alkanediyl, and most preferably linear C6 alkanediyl,
$R^{22}$ is C1-C10 alkanediyl, preferably linear alkanediyl, more preferably linear C2-C6 alkanediyl, w is 1, 2 or 3, preferably 1 or 2,
$R^{23}$ is an oligoether moiety, preferably a linear oligoether moiety, more preferably a linear oligoether moiety having 5 to 10 carbon atoms and 2 or 3 oxygen atoms providing the ether bonds, x is 1, 2 or 3, preferably 1 or 2,
and $R^{B1}$ is as defined above.

The chelating moiety of (i) and (ii), both in the context of the definition of $R^B$ and $R^{B1}$, is suitable to form a chelate with a radioactive or non-radioactive cation. Suitable chelating moieties for diverse cations are well known in the art, and can be used in the context of the present invention.

Preferably, the chelating moiety comprises at least one of
a macrocyclic ring structure with 8 to 20 ring atoms of which 2 or more, preferably 3 or more, are selected from oxygen atoms, sulfur atoms and nitrogen atoms; and
an acyclic, open chain chelating structure with 8 to 20 main chain atoms of which 2 or more, preferably 3 or more are heteroatoms selected from oxygen atoms, sulfur atoms and nitrogen atoms.

A preferred example for the chelating moiety is a residue of a chelating agent such as bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicyclo[6.6.2]hexadecane (DO2A), 1,4,7,10-tetraazacyclododecane-N,N',N'',N'''-tetraacetic acid (DOTA), α-(2-carboxyethyl)-1,4,7,10-tetraazacyclododecane-1,4,7,10-tetraacetic acid or 2-[1,4,7,10-tetraazacyclododecane-4,7,10-triacetic acid]-pentanedioic acid (DOTAGA), N,N'-dipyridoxylethylendiamine-N,N'-diacetate-5,5'-bis(phosphate) (DPDP), diethylenetriaminepentaacetic acid (DTPA), ethylenediamine-N,N'-tetraacetic acid (EDTA), ethyleneglycol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecane-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2]hexadecane (TE2A), 1,4,8,11-tetraazacyclododecane-1,4,8,11-tetraacetic acid (TETA), terpyridin-bis(methyleneamintetraacetic acid (TMT), 1,4,7,10-tetraazacyclotridecan-N,N',N",N"'-tetraacetic acid (TRITA), triethylenetetraaminehexaacetic acid (TTHA), N,N'-bis[(6-carboxy-2-pyridyl)methyl]-4,13-diaza-18-crown-6 (H$_2$macropa), and 4-amino-4-{2-[(3-hydroxy-1,6-dimethyl-4-oxo-1,4-dihydro-pyridin-2-ylmethyl)-carbamoyl]-ethyl} heptanedioic acid bis-[(3-hydroxy-1,6-dimethyl-4-oxo-1,4-dihydro-pyridin-2-ylmethyl)-amide] (THP), which residue is obtainable by covalently binding a carboxyl group contained in the chelating agent to the remainder of the compound via an ester or an amide bond, preferably an amide bond. For example, in formulae (VIa) to (VIf), an amide bond can be conveniently formed directly from a carboxyl group contained in the above exemplary chelating agents and the nitrogen atom to which $R^B$ or $R^{B1}$, respectively, is attached in these formulae.

In a more preferred example, the chelating moiety of (i) or (ii) in the context of the definition of $R^B$ or $R^{B1}$ is a residue of a chelating agent selected from DOTA and DOTAGA, still more preferably a residue obtainable by forming an amide bond from a carboxyl group contained in DOTA and DOTAGA, and the nitrogen atom to which $R^{B1}$ is attached in formulae (VIa) to (VIf).

Exemplary radioactive cations that are optionally chelated by the chelating moiety in accordance with (ii), both in the context of the definition of $R^B$ and $R^{B1}$ are selected from the cations of $^{44}$Sc, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{89}$Zr, $^{90}$Y, $^{89}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At, $^{212}$Bi, $^{213}$Bi, $^{223}$Ra, $^{225}$AC, and $^{227}$Th, or a cationic molecule comprising $^{18}$F, such as $^{18}$F—[AlF]$^{2+}$.

Preferred chelated cations are selected from the cations of $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, and $^{227}$Th, or a cationic molecule comprising $^{18}$F. Even further preferred are cations of $^{68}$Ga, $^{90}$Y, $^{177}$Lu, $^{212}$Bi, and $^{213}$Bi.

Moieties (iii) carrying a covalently bound radioisotope, preferably $^{18}$F-fluoride, or precursors suitable to be labeled with such radioisotope as referred to in the definition of $R^B$ and $R^{B1}$ can be used as known in the art.

As examples of such a precursor, reference can be made to a group of formula —N$^+$(CH$_3$)$_2$—CH$_2$—BF$_3^-$ and to a group of the formula —Ar—SiF(C(CH$_3$)$_3$)$_2$, wherein Ar is a divalent aromatic group, preferably a phenylene group. As will be appreciated by the skilled reader, such a group of the formula —Ar—SiF(C(CH$_3$)$_3$)$_2$ can be conveniently bound to the remainder of the compounds in accordance with the invention by a functional group which may be attached to Ar at the open valence as indicated in the formula, and which is suitable for covalent coupling of the group —Ar—SiF(C(CH$_3$)$_3$)$_2$. For example, reference can be made to an amide bond or an ester bond which can be formed e.g. if the group —Ar—SiF(C(CH$_3$)$_3$)$_2$ is provided as a part of a benzoic acid derivative of the formula —C(O)—C6H4-SiF(C(CH$_3$)$_3$)$_2$.

Phosphonate moieties (iv), i.e. moieties comprising the structure —P(=O)(OH)$_2$ or salts thereof as referred to in the definition of $R^B$ and $R^{B1}$ can also be used as known in the art.

As a fluorescent label (v) as referred to in the definition of $R^B$ and $R^{B1}$, a fluorescent dye, such as Cy5 or Cy7, or a quantum dot may be used.

Furthermore, $R^B$ and $R^{B1}$, respectively, may further comprise a group of formula (II)

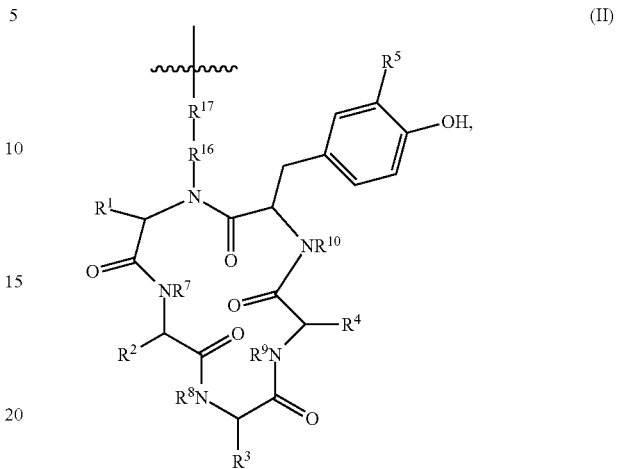

which is bound to the remainder of the compound with the bond marked with ⌇⌇⌇, wherein $R^1$ to $R^5$ and $R^7$ to $R^{10}$ are as defined for formula (I) including their preferred meanings, and wherein $R^{16}$ is an alkanediyl group, preferably a C1-C6 alkanediyl group, and $R^{17}$ is selected from —NH— and —NH—C(=NH)—NH—.

In a second aspect, the invention provides a pharmaceutical composition comprising or consisting of a compound or salt of the first aspect.

In a third aspect, the invention provides a diagnostic composition comprising or consisting of a compound or salt of the first aspect.

The pharmaceutical composition may further comprise pharmaceutically acceptable carriers, excipients and/or diluents. Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by wellknown conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection and/or delivery, e.g., to a site in the pancreas or into a brain artery or directly into brain tissue. The compositions may also be administered directly to the target site, e.g., by biolistic delivery to an external or internal target site, like the pancreas or brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Pharmaceutically active matter may be present in amounts between 0.1 ng and 10 mg/kg body weight per dose; however, doses below or above this exemplary range are envisioned, especially considering the aforementioned factors.

The above applies mutatis mutandis also to diagnostic compositions.

To the extent the above disclosed pharmaceutical composition, diagnostic composition and therapeutic composition comprises one or more compounds of the invention, it is preferred that no further pharmaceutically active compounds, diagnostically active compounds or therapeutically active compounds are present. In the alternative, further therapeutically active, diagnostically active or pharmaceutically active compounds may be present, for example, anticancer agents.

In a fourth aspect, the invention provides a compound or salt of the first aspect for use in medicine, preferably in nuclear medicine, for nuclear molecular imaging, optical imaging, and endoradiotherapy, preferably targeted endoradiotherapy.

In a fifth aspect, the invention provides a compound or salt of the first aspect for use in a method of treating or preventing cancer, cardiovascular diseases, AIDS or inflammatory disorders. These medical uses arise from expression, tissue distribution and/or activity of CXCR4 as discussed in the introductory section herein above.

In a sixth aspect, the invention provides a compound or salt of the first aspect for use in a method of diagnosing and/or staging cancer.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed. This applies likewise for the following items.

In particular, the invention includes the following items:
1. A compound of the following formula (I)

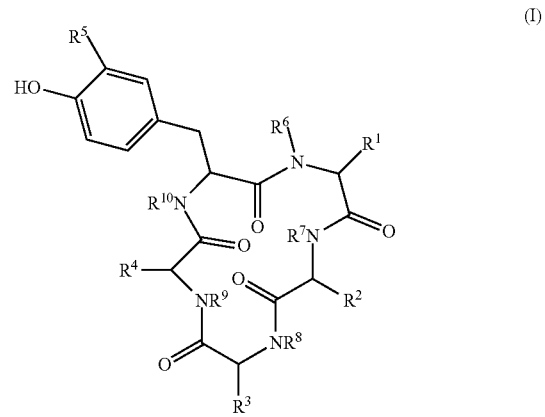

or a pharmaceutically acceptable salt thereof, wherein:
$R^1$ is alkyl, preferably C1-C6 alkyl, more preferably methyl;
$R^2$ is H or alkyl, which alkyl may be unsubstituted or substituted with at least one substituent selected from $-NH_2$, $-NH-C(=NH)-NH_2$, $-C(O)NH_2$, $-C(O)OH$, $-OH$, $-SH$, $-SCH_3$ and a 5 to 10-membered carbocycle or 5 to 10-membered heterocycle containing oxygen, nitrogen or sulfur as heteroatom(s), wherein the alkyl is preferably C1-C6 alkyl;
$R^2$ is H or alkyl, which alkyl may be unsubstituted or substituted with at least one substituent selected from $-NH_2$, $-NH-C(=NH)-NH_2$, $-C(O)NH_2$, $-C(O)OH$, $-OH$, $-SH$, $-SCH_3$ and a 5 to 10-membered carbocycle or 5 to 10-membered heterocycle containing oxygen, nitrogen or sulfur as heteroatom(s), wherein the alkyl is preferably C1-C6 alkyl;
$R^4$ is H or alkyl, which alkyl may be unsubstituted or substituted with at least one substituent selected from $-NH_2$, $-NH-C(=NH)-NH_2$, $-C(O)NH_2$, $-C(O)OH$, $-OH$, $-SH$, $-SCH_3$, $-SR^4$, $-SR^{11}$, and a 5 to 10-membered carbocycle or 5 to 10-membered heterocycle containing oxygen, nitrogen or sulfur as heteroatom(s), wherein the alkyl is preferably C1-C6 alkyl,
$R^5$ is H or I;
$R^6$ is alkyl substituted with at least one substituent selected from $-NH_2$, $-NH-C(=NH)-NH_2$, $-NH-R^B$, $-NH-C(=NH)-NH-R^B$, $-NH-C(=NH)-NH-R^{14}$, and $-NH-C(=NH)-NH-C(=O)-R^{15}$, wherein the alkyl is preferably C1-C8 alkyl,
$R^7$ to $R^{10}$ are each independently H or alkyl; preferably H or C1-C6 alkyl; and more preferably H;
$R^{11}$ is selected from $-(CH_2)-C(=O)-NH-R^{12}-NH-C(=O)-CH_3$ and $-(CH_2)-C(=O)-NH-(CH_2)_r-R^{13}-(CH_2)_s-NH-C(=O)-CH_3$, wherein $R^{12}$ is a C2-C10 alkanediyl group, preferably a C3-C6 alkanediyl group, which alkanediyl group may be substituted by a group $-C(=O)-NH_2$, $R^{13}$ is a phenylene group, preferably a 1,3-phenylene group, and r and s are independently integers selected from 0, 1 or 2, and are preferably both 1;

$R^{14}$ and $R^{15}$ are independently C1-C10 alkyl, preferably C2-C6 alkyl, which alkyl may be substituted by at least one substituent selected from —NH—C(=O)—CH$_3$ and —C≡CH;

$R^A$ is a group which comprises at least one selected from:
(i) a chelating moiety,
(ii) a chelate formed by a chelating moiety (i) with a chelated radioactive or non-radioactive cation,
(iii) a moiety carrying a covalently bound radioisotope, or a precursor suitable to be labeled with such a radioisotope,
(iv) a phosphonate moiety, and
(v) a fluorescent label, such as a quantum dot or fluorescent dye; and $R^B$ is a group which comprises at least one selected from:
(i) a chelating moiety,
(ii) a chelate formed by a chelating moiety with a chelated radioactive or non-radioactive cation,
(iii) a group carrying a covalently bound radioisotope, or a precursor suitable to be labeled with such a radioisotope,
(iv) a phosphonate moiety, and
(v) a fluorescent label, such as a quantum dot or fluorescent dye,
and $R^B$ may further comprise a group of formula (II)

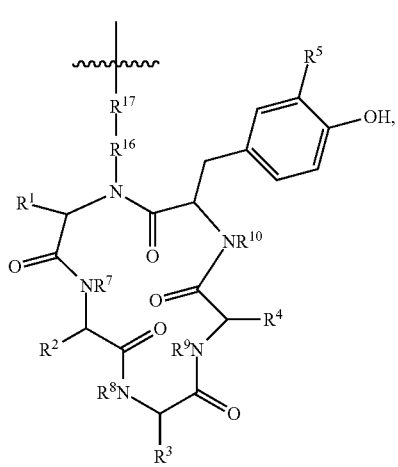

(II)

which is bound to the remainder of the compound with the bond marked with ~~~~, wherein $R^1$ to $R^5$ and $R^7$ to $R^{10}$ are as defined above, and wherein $R^{16}$ is an alkanediyl group, preferably a C1-C6 alkanediyl group, and $R^{17}$ is selected from —NH— and —NH—C(=NH)—NH—;
and wherein
said compound of formula (I) comprises at least one substituent selected from —S—$R^A$, —NH—$R^6$ and —NH—C(=NH)—NH—$R^B$.

2. The compound or salt of item 1, wherein $R^1$ is a C1-C6 alkyl group
3. The compound or salt of item 2, wherein $R^1$ is methyl.
4. The compound of salt of any of items 1 to 3, wherein $R^2$ is C1-C6 alkyl, substituted with one group selected from —NH$_2$ and —NH—C(=NH)—NH$_2$.
5. The compound or salt of item 4, wherein $R^2$ is —CH$_2$—CH$_2$—CH$_2$—NH—C(=NH)—NH$_2$.

6. The compound or salt of any of items 1 to 5, wherein $R^3$ is methyl, substituted with a 5 to 10-membered carbocycle.
7. The compound or salt of item 6, wherein $R^3$ is a group —(CH$_2$)-naphthyl.
8. The compound or salt of any of items 1 to 7, wherein $R^7$ to $R^{10}$ are H.
9. The compound or salt of any of items 1 to 8, wherein $R^5$ is H.
10. The compound of any of items 1 to 9, which is a compound of formula (III):

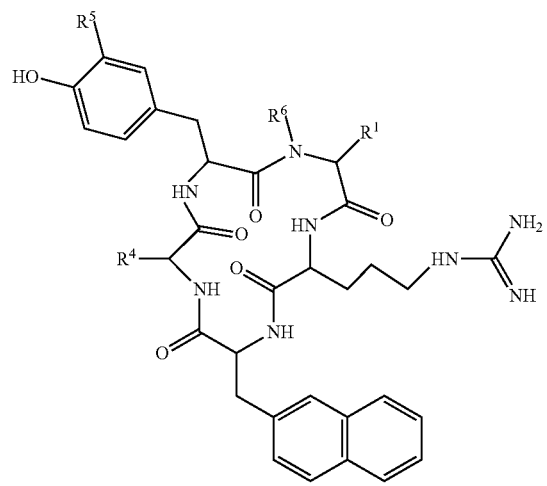

(III)

or a pharmaceutically acceptable salt thereof, wherein $R^1$, $R^4$, $R^5$ and $R^6$ are defined as in any of items 1 to 3 and 9.

11. The compound of item 10, which is a compound of formula (IV):

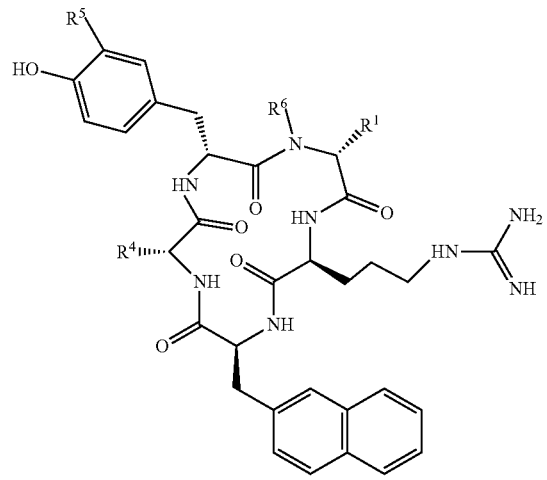

(IV)

or a pharmaceutically acceptable salt thereof, wherein $R^1$, $R^4$, $R^5$ and $R^6$ are defined as in any of items 1 to 3 and 9.

12. The compound or salt of any of items 1 to 11, wherein $R^4$ is H or C1-C6 alkyl substituted with one substituent selected from —SH, —$SR^A$ and —$SR^{11}$, wherein $R^A$ and $R^{11}$ are defined as in item 1.

13. The compound or salt of item 12, wherein $R^4$ is H, —$CH_2$—SH, —$CH_2$—$SR^A$ or —$CH_2$—$SR^{11}$, wherein $R^A$ and $R^{11}$ are defined as in item 1.

14. The compound or salt of any of items 1 to 13, wherein $R^6$ is C1-C8 alkyl substituted with one group selected from —NH—C(=NH)—$NH_2$, —NH—C(=NH)—NH—$R^B$, —NH—C(=NH)—NH—$R^{14}$, and —NH—C(=NH)—NH—C(=O)—$R^{15}$, wherein $R^B$, $R^{14}$ and $R^{15}$ are defined as in item 1.

15. The compound or salt of item 14, wherein $R^6$ is a linear C6 alkyl, substituted at its terminal C-atom with one group selected from —NH—C(=NH)—$NH_2$, —NH—C(=NH)—NH—$R^B$, —NH—C(=NH)—NH—$R^{14}$, and —NH—C(=NH)—NH—C(=O)—$R^{15}$, wherein $R^B$, $R^{14}$ and $R^{15}$ are defined as in item 1.

16. The compound or salt of any of items 1 to 15, which comprises one substituent selected from —$SR^A$ and —NH—C(=NH)—NH—$R^B$ 17. The compound of any of items 1 to 9, which is a compound of formula (Ia):

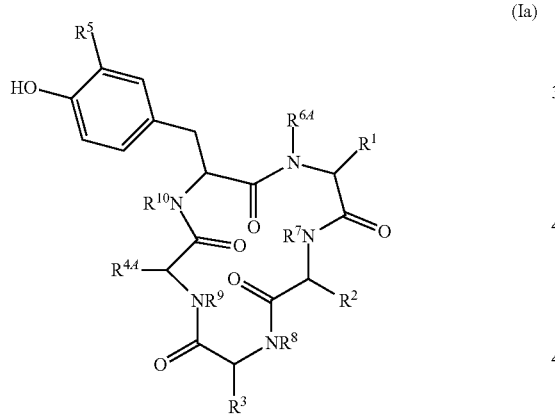

(Ia)

or a pharmaceutically acceptable salt thereof, wherein
$R^1$ to $R^3$, $R^5$ and $R^7$ to $R^{10}$ are defined as in items 1 to 9,
$R^{4A}$ is H or alkyl, which alkyl may be unsubstituted or substituted with one substituent selected from —$NH_2$, —NH—C(=NH)—$NH_2$, —C(O)$NH_2$, —C(O)OH, —OH, —SH, —$SCH_3$, —$SR^{11}$, and a 5 to 10-membered carbocycle or 5 to 10-membered heterocycle containing oxygen, nitrogen or sulfur as heteroatom(s), wherein $R^{11}$ is defined as in item 1, and
$R^{6A}$ is alkyl substituted with one substituent selected from —NH—$R^6$ and —NH—C(=NH)—NH—$R^B$, wherein $R^B$ is defined as in item 1.

18. The compound of item 17, which is a compound of formula (IIIa):

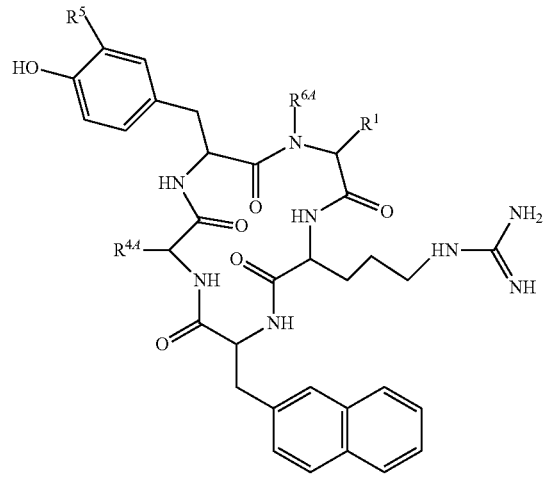

(IIIa)

or a pharmaceutically acceptable salt thereof, wherein $R^1$, $R^{4A}$, $R^{6A}$ and $R^5$ are defined as in item 17.

19. The compound of item 18, which is a compound of formula (IVa):

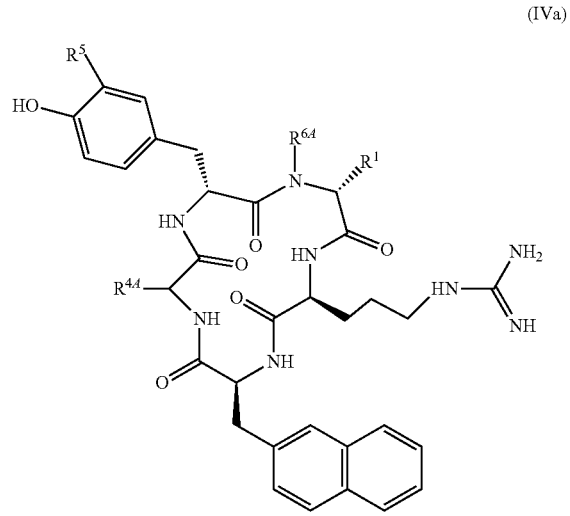

(IVa)

or a pharmaceutically acceptable salt thereof, wherein $R^1$, $R^{4A}$, $R^{6A}$ and $R^5$ are defined as in item 17, 20. The compound or salt of any of items 17 to 19, wherein $R^{4A}$ is selected from H, —$CH_2$—SH, and —$CH_2$—$SR^{11}$, wherein $R^{11}$ is defined as in item 1.

21. The compound or salt of item 20, wherein $R^{4A}$ is H.

22. The compound or salt of any of items 17 to 21, wherein $R^{6A}$ is a linear C2-C6 alkyl, substituted at its terminal C-atom with one group —NH—C(=NH)—NH—$R^B$, wherein $R^B$ is defined as in item 1.

23. The compound or salt of item 22, wherein $R^{6A}$ is -(linear C6 alkyl)-NH—C(=NH)—NH—$R^B$, wherein $R^B$ is defined as in item 1.

24. The compound of any of items 1 to 9, which is a compound of formula (Ib):

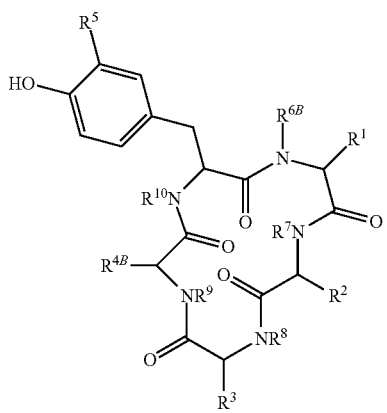
(Ib)

or a pharmaceutically acceptable salt thereof, wherein $R^1$ to $R^3$, $R^5$ and $R^7$ to $R^{10}$ are defined as in items 1 to 9, $R^{4B}$ is alkyl substituted with one substituent —$SR^A$ wherein $R^A$ is as defined in item 1, and $R^{6B}$ is alkyl substituted with one substituent selected from —$NH_2$, —NH—C(=NH)—$NH_2$, —NH—C(=NH)—NH—$R^{14}$, and —NH—C(=NH)—NH—C(=O)—$R^{15}$, wherein $R^{14}$ and $R^{15}$ are defined in item 1.

25. The compound of item 24, which is a compound of formula (IIIb):

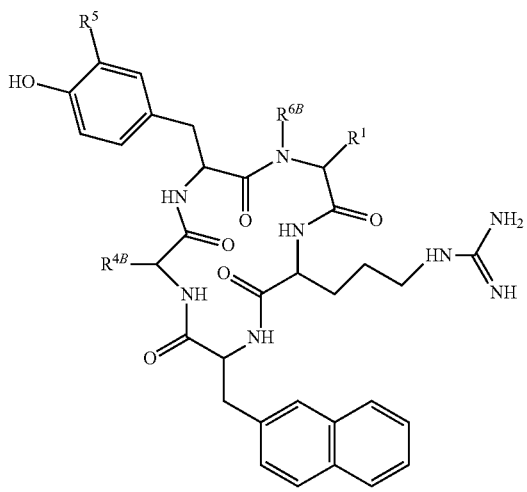
(IIIb)

or a pharmaceutically acceptable salt thereof, wherein $R^1$, $R^{4B}$, $R^{6B}$ and $R^5$ are defined as in item 24.

26. The compound of item 26, which is a compound of formula (IVb):

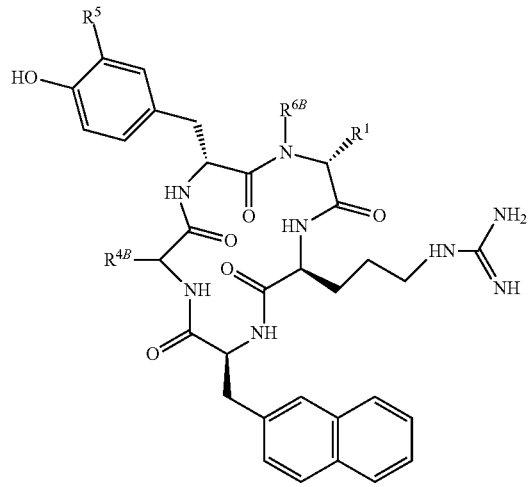
(IVb)

or a pharmaceutically acceptable salt thereof, wherein $R^1$, $R^{4B}$, $R^{6B}$ and $R^5$ are defined as in item 24.

27. The compound or salt of any of items 24 to 26, wherein $R^{4B}$ is C1-C6 alkyl substituted with one substituent —$SR^A$.

28. The compound or salt of item 27, wherein $R^{4B}$ is —$CH_2$—$SR^A$.

29. The compound or salt of any of items 24 to 28, wherein $R^{6B}$ is a linear C2-C6 alkyl substituted with one substituent selected from —$NH_2$, —NH—C(=NH)—$NH_2$, —NH—C(=NH)—NH—$R^{14}$, and —NH—C(=NH)—NH—C(=O)—$R^{15}$, wherein $R^{14}$ and $R^{15}$ are defined as in item 1.

30. The compound or salt of item 29, wherein $R^{6B}$ is -(linear C6 alkyl)-NH—C(=NH)—$NH_2$.

31. The compound or salt of any of items 1 to 23, wherein $R^B$ is a group of the formula -$L^{B1}$-$R^{B1}$, wherein L is a divalent linking group, and $R^{B1}$ is or comprises a group selected from
   (i) a chelating moiety,
   (ii) a chelate formed by a chelating moiety (i) with a chelated radioactive or non-radioactive cation,
   (iii) a moiety carrying a covalently bound radioisotope, or a precursor suitable to be labeled with such a radioisotope,
   (iv) a phosphonate moiety, and
   (v) a fluorescent label, such as a quantum dot or fluorescent dye, and wherein $R^{B1}$ may further comprise a group of formula (II) as defined in item 1.

32. The compound or salt of item 31, wherein -$L^{B1}$-$R^{B1}$ is selected from the groups of formulae (VIa) to (VIf):

—$R^{18}$—NH—$R^{B1}$ (VIa),

—$R^{18}$—NH—(C(=O)—$R^{19}$—NH)$_u$—$R^{B1}$ (VIb),

—$R^{18}$—NH—(C(=O)—$R^{20}$—NH)$_v$—$R^{B1}$ (VIc),

—(C=O)—$R^{21}$—NH—$R^{b1}$ (VId),

—(C=O)—$R^{21}$—NH—(C(=O)—$R^{22}$—NH)$_w$—$R^{b1}$ (VIe),

—(C=O)—$R^{21}$—NH—(C(=O)—$R^{23}$—NH)$_x$—$R^{B1}$ (VIf), wherein:
- $R^{18}$ is C1-C10 alkanediyl, preferably linear alkanediyl, more preferably linear C2-C6 alkanediyl, and most preferably linear C6 alkanediyl,
- $R^{19}$ is C1-C10 alkanediyl, preferably linear alkanediyl, more preferably linear C2-C6 alkanediyl, u is 1, 2 or 3, preferably 1 or 2,
- $R^{20}$ is an oligoether moiety, preferably a linear oligoether moiety, more preferably a linear oligoether moiety having 5 to 10 carbon atoms and 2 or 3 oxygen atoms providing the ether bonds, v is 1, 2 or 3, preferably 1 or 2,
- $R^{21}$ is C1-C10 alkanediyl, preferably linear alkanediyl, more preferably linear C2-C6 alkanediyl, and most preferably linear C6 alkanediyl,
- $R^{22}$ is C1-C10 alkanediyl, preferably linear alkanediyl, more preferably linear C2-C6 alkanediyl, w is 1, 2 or 3, preferably 1 or 2,
- $R^{23}$ is an oligoether moiety, preferably a linear oligoether moiety, more preferably a linear oligoether moiety having 5 to 10 carbon atoms and 2 or 3 oxygen atoms providing the ether bonds, x is 1, 2 or 3, preferably 1 or 2,
- and $R^{B1}$ is as defined in item 31.

33. The compound or salt of any of items 1 to 23, wherein $R^B$ comprises (i) a chelating moiety or (ii) a chelate formed by a chelating moiety (i) with a chelated radioactive or non-radioactive cation.

34. The compound or salt of item 31 or 32, wherein $R^{B1}$ comprises (i) a chelating moiety or (ii) a chelate formed by a chelating moiety (i) with a chelated radioactive or non-radioactive cation, or wherein $R^{B1}$ is (i) a chelating moiety or (ii) a chelate formed by a chelating moiety (i) with a chelated radioactive or non-radioactive cation.

35. The compound or salt of item 33 or 34, wherein the chelating moiety comprises at least one of
- a macrocyclic ring structure with 8 to 20 ring atoms of which 2 or more, preferably 3 or more, are selected from oxygen atoms and nitrogen atoms; and
- an acyclic, open chain chelating structure with 8 to 20 main chain atoms of which 2 or more, preferably 3 or more are heteroatoms selected from oxygen atoms, sulfur atoms and nitrogen atoms.

36. The compound or salt of any of items 33 to 35, wherein the chelating moiety is a residue derived from a chelating agent selected from bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicyclo[6.6.2]hexadecane (DO2A), 1,4,7,10-tetraazacyclododecane-N,N',N'',N'''-tetraacetic acid (DOTA), α-(2-carboxyethyl)-1,4,7,10-tetraazacyclododecane-1,4,7,10-tetraacetic acid or 2-[1,4,7,10-tetraazacyclododecane-4,7,10-triacetic acid]-pentanedioic acid (DOTAGA), N,N'-dipyridoxylethylendiamine-N,N'-diacetate-5,5'-bis(phosphate) (DPDP), diethylenetriaminepentaacetic acid (DTPA), ethylenediamine-N,N'-tetraacetic acid (EDTA), ethyleneglycol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecane-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2]hexadecane (TE2A), 1,4,8,11-tetraazacyclododecane-1,4,8,11-tetraacetic acid (TETA), terpyridin-bis(methyleneamintetraacetic acid (TMT), 1,4,7,10-tetraazacyclotridecan-N,N',N'',N'''-tetraacetic acid (TRITA), triethylenetetraaminehexaacetic acid (TTHA), N,N'-bis[(6-carboxy-2-pyridyl)methyl]-4,13-diaza-18-crown-6 ($H_2$macropa), and 4-amino-4-{2-[(3-hydroxy-1,6-dimethyl-4-oxo-1,4-dihydro-pyridin-2-yl-methyl)-carbamoyl]-ethyl} heptanedioic acid bis-[(3-hydroxy-1,6-dimethyl-4-oxo-1,4-dihydro-pyridin-2-ylmethyl)-amide] (THP), which residue is obtainable by covalently binding a carboxyl group contained in the chelating agent to the remainder of the compound via an ester or an amide bond.

37. The compound or salt of item 36, wherein the chelating agent is selected from DOTA and DOTAGA.

38. The compound or salt of item 36, wherein $R^B$ is a group of the formula -$L^{B1}$-$R^{B1}$, -L-$R^{B1}$ is as defined in item 32, and $R^{B1}$ is a chelating moiety derived from the chelating agent DOTA or DOTAGA by forming an amide bond between a carboxyl group of the chelating agent and the nitrogen atom to which $R^{B1}$ is attached in the group of any of formulae (VIa) to (VIf).

39. The compound or salt of any of items 33 to 38, wherein $R^B$ comprises a chelate formed by a chelating moiety with a chelated radioactive cation, or wherein $R^{B1}$ is or comprises a chelate formed by a chelating moiety with a chelated radioactive cation, and wherein the chelated radioactive cation is selected from a cation of $^{44}$Sc, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{89}$Zr, $^{90}$Y, $^{89}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At, $^{212}$Bi, $^{213}$Bi, $^{223}$Ra, $^{225}$AC, and $^{227}$Th, or a cationic molecule comprising $^{18}$F, such as $^{18}$F—[AlF]$^{2+}$.

40. The compound or salt of item 39, wherein the radioactive cation is selected from a cation of $^{99m}$Tc, $^{186}$Re, $^{188}$Re, $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, and $^{227}$Th or a cationic molecule comprising $^{18}$F.

41. The compound or salt of any of items 1 to 16 and 24 to 30, wherein $R^4$ is a group of the formula -$L^{41}$-$R^{41}$, wherein $L^{41}$ is a divalent linking group and $R^{41}$ is or comprises a group selected from:

(i) a chelating moiety, (ii) a chelate formed by a chelating moiety (i) with a chelated radioactive or non-radioactive cation, (iii) a moiety carrying a covalently bound radioisotope, or a precursor suitable to be labeled with such a radioisotope, (iv) a phosphonate moiety, and (v) a fluorescent label, such as a quantum dot or fluorescent dye.

42. The compound or salt of item 41, wherein -$L^{41}$-$R^{41}$ is selected from the groups of formulae (IVa) and (IVb):

—(CH$_2$)—C(=O)—NH—R$^{24}$—NH—R$^{41}$ (IVa),

—(CH$_2$)—C(=O)—NH—(CH$_2$)$_y$—R$^{25}$—(CH$_2$)$_z$—NH—R$^{41}$ (IVb), wherein $R^{24}$ is a C2-C10 alkanediyl group, preferably a C3-C6 alkanediyl group, which alkanediyl group is preferably linear and may be substituted by a group —C(=O)—NH$_2$, $R^{25}$ is a phenylene group, preferably a 1,3-phenylene group, and y and z are independently integers selected from 0, 1 or 2, and are preferably both 1, and $R^{41}$ is as defined in item 41.

43. The compound or salt of item 42, wherein -$L^{41}$-$R^{41}$ is a group of formula (IVb).

44. The compound or salt of any of items 1 to 16 and 24 to 30, wherein $R^4$ comprises (i) a chelating moiety or (ii) a chelate formed by a chelating moiety (i) with a chelated radioactive or non-radioactive cation, 45. The compound or salt of any of items 41 to 43, wherein $R^{41}$ comprises (i) a chelating moiety or (ii) a chelate formed by a chelating moiety (i) with a chelated radioactive or non-radioactive cation, or wherein $R^{41}$ is (i) a chelating moiety or (ii) a chelate formed by a chelating moiety (i) with a chelated radioactive or non-radioactive cation.

46. The compound or salt of any of items 44 or 45, wherein wherein the chelating moiety comprises at least one of a macrocyclic ring structure with 8 to 20 ring atoms of which 2 or more, preferably 3 or more, are selected from oxygen atoms and nitrogen atoms; and an acyclic, open chain chelating structure with 8 to 20 main chain atoms of which 2 or more, preferably 3 or more are heteroatoms selected from oxygen atoms and nitrogen atoms.

47. The compound or salt of any of items 44 to 46, wherein the chelating moiety is chelating agent such as bis(carboxymethyl)-1,4,8,11-tetraazabicyclo[6.6.2] hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl (hydroxy)amino]pentyl]-N-[5-[[4-[5-aminopentyl-(hydroxy)amino]-4-oxobutanoyl]amino]pentyl]-N-hydroxybutandiamide (DFO), 4,11-bis (carboxymethyl)-1,4,8,11-tetraazabicyclo[6.6.2] hexadecane (DO2A), 1,4,7,10-tetraazacyclododecane-N,N',N'',N'''-tetraacetic acid (DOTA), α-(2-carboxyethyl)-1,4,7,10-tetraazacyclododecane-1,4,7,10-tetraacetic acid or 2-[1,4,7,10-tetraazacyclododecane-4,7,10-triacetic acid]-pentanedioic acid (DOTAGA), N,N'-dipyridoxylethylendiamine-N,N'-diacetate-5,5'-bis (phosphate) (DPDP), diethylenetriaminepentaacetic acid (DTPA), ethylenediamine-N,N'-tetraacetic acid (EDTA), ethyleneglycol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecane-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis (carboxymethyl)-1,4,8,11-tetraazabicyclo[6.6.2] hexadecane (TE2A), 1,4,8,11-tetraazacyclododecane-1,4,8,11-tetraacetic acid (TETA), terpyridin-bis (methyleneamintetraacetic acid (TMT), 1,4,7,10-tetraazacyclotridecan-N,N',N'',N'''-tetraacetic acid (TRITA), triethylenetetraaminehexaacetic acid (TTHA), N,N'-bis[(6-carboxy-2-pyridyl)methyl]-4,13-diaza-18-crown-6 (H$_2$macropa), and 4-amino-4-{2-[(3-hydroxy-1,6-dimethyl-4-oxo-1,4-dihydro-pyridin-2-yl-methyl)-carbamoyl]-ethyl} heptanedioic acid bis-[(3-hydroxy-1,6-dimethyl-4-oxo-1,4-dihydro-pyridin-2-ylmethyl)-amide] (THP), which residue is obtainable by covalently binding a carboxyl group contained in the chelating agent to the remainder of the compound via an ester or an amide bond.

48. The compound or salt of item 47, wherein the chelating agent is selected from DOTA and DOTAGA.

49. The compound or salt of item 47, wherein $R^4$ is a group of the formula -$L^{41}$-$R^{41}$, -$L^{41}$-$R^{41}$ is a group of formula (IVb), and $R^{41}$ is a chelating moiety derived from the chelating agent DOTA or DOTAGA by forming an amide bond between a carboxyl group of the chelating agent and the nitrogen atom to which $R^{41}$ is attached in the group of formula (IVb).

50. The compound or salt of any of items 44 to 49, wherein $R^4$ comprises a chelate formed by a chelating moiety with a chelated radioactive cation, or wherein $R^{41}$ is or comprises a chelate formed by a chelating moiety with a chelated radioactive cation, and wherein the chelated radioactive cation is selected from a cation of $^{44}$Sc, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{89}$Zr, $^{90}$Y, $^{89}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At, $^{212}$Bi, $^{213}$Bi, $^{223}$Ra, $^{225}$AC, and $^{227}$Th, or a cationic molecule comprising $^{18}$F, such as $^{18}$F—[AlF]$^{2+}$.

51. The compound or salt of item 50, wherein the radioactive cation is selected from a cation of $^{99m}$Tc, $^{186}$Re, $^{188}$Re, $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, and $^{227}$Th or a cationic molecule comprising $^{18}$F.

52. A pharmaceutical composition comprising or consisting of a compound or salt of any one of items 1 to 51.

53. A diagnostic composition comprising or consisting of a compound or salt of any one of items 1 to 51.

54. A compound or salt of any one of items 1 to 51 for use in medicine, preferably in nuclear medicine, for nuclear molecular imaging, or optical imaging, or targeted endoradiotherapy.

55. A compound or salt of any one of items 1 to 51 for use in a method of treating or preventing cancer, cardiovascular diseases, AIDS or inflammatory disorders.

56. A compound or salt of any one of items 1 to 51 for use in a method of diagnosing and/or staging cancer.

EXAMPLE 1

Chemicals and Instrumentation

Figure 1:
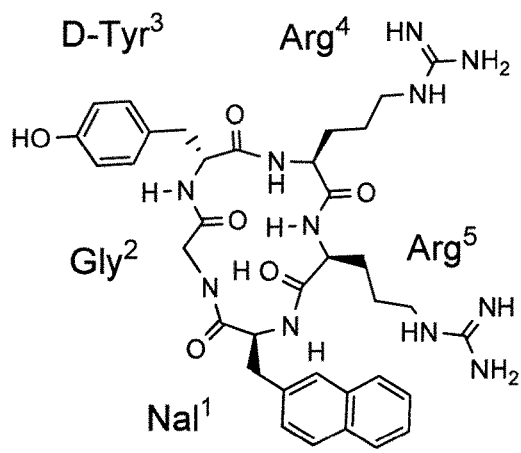
FIG. 1: Structures of cyclic CXCR4-binding molecules.
Figure 1:
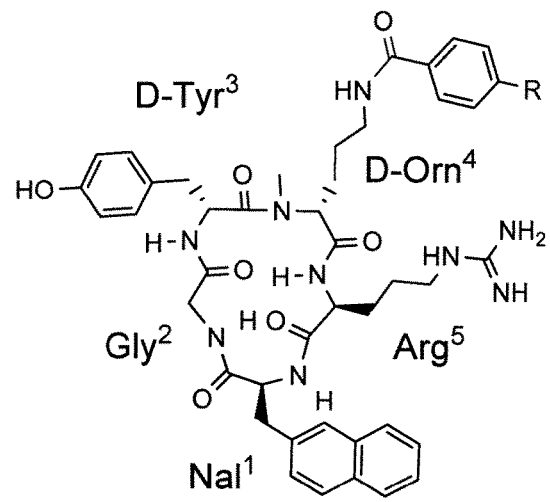
Figure 1:
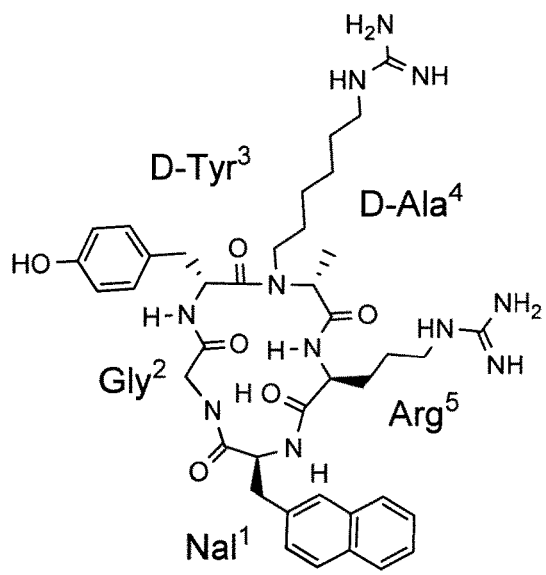
Figure 1:
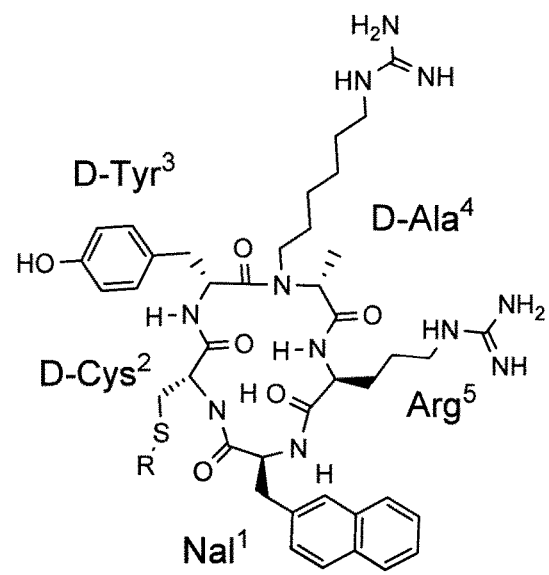

Solvents were purchased from Aldrich, Fluka, Merck and Prolabo, reagents from Aldrich, Fluka, Sigma, Merck, Acros and Lancaster in the quality "for synthesis", "per analysis" or "HPLC grade" and used without purification. Amino acids, derivatives for protecting groups as well as coupling reagents were purchased from Iris Biotech (Marktredwitz, Germany), Bachem (Bubendorf, Switzerland) or Carbolution (Saarbrücken, Germany). All reaction sensitive to oxygen or water were carried out in an argon atmosphere.

Solid phase peptide synthesis was carried out in plastic syringes (VWR) which were equipped with a filter. Reaction and wash solutions were sucked in the syringe, for mixing, the syringes were shaken manually or using an Intelli-Mixer syringe shaker (Neolab, Heidelberg, Germany). For loading of the first amino acid, the required equivalents (eq.) were calculated based on the theoretical loading capacity provided by the supplier.

Thin layer chromatography (TLC) for reaction control and the determination of $R_f$-values was done on aluminium foils coated with Silica 60, F254 (Merck). Peak detection was done under UV-light (254 nm) or after staining with Mostain-solution, respectively.

Preparative flash chromatogaphy was performed with 50- to 100-fold mass excess Silica 60 (particle size 0.040-0.063 mm, Merck) applying 1-1.5 bar overpressure.

Analytical and semipreparative reversed phase high performance liquid chromatography (HPLC) was performed using the following devices:

a) Amersham Pharmacia Biotech: Äkta Basic, 10 F, Autosampler A 900, Pumping system P-900, Detector UV-900, Software Unicorn Vers. 3.00. Column: YMC-ODS-A C18 (120 Å, 5 µm, 250 mm×4.6 mm), analytical.

b) Amersham Pharmacia Biotech: Äkta Basic, 100 F, Pumping system P-900, Detector UV-900, Software Unicorn Vers. 3.00. Column: YMC-ODS-A C18 (120 Å, 10 µm, 250 mm×20 mm), semipreparative.

c) Beckman: High pressure pumping module 125, UV-Detector 166. Software System Gold; Column: YMC-ODS-A C18 (120 Å, 5 µm, 250 mm×20 mm), semipreparative.

d) Sykam; gradient HPLC System (Sykam GmbH, Eresing, Germany), 206 PHD UV-Vis detector (Linear™ Instruments Corporation, Reno, USA), Winnie 32 software. Columns: a) Nucleosil 100 C18 (5 µm, 125×4.0 mm) (CS Chromatographie Services GmbH, Langerwehe, Germany), analytical, and b) Multospher 100 RP 18-5 (250×20 mm) (CS), semipreparative. For radioactivity detection, the outlet of the UV-photometer was connected to a NaI(TI) well-type scintillation counter from EG&G Ortec (München, Germany).

e) Shimadzu: Prominence Gradient HPLC System (Shimadzu, Duisburg, Germany).

As eluents, mixtures of $H_2O$ (solvent A) and acetonitrile (solvent B) containing 0.1 vol-% TFA were used. Different, linear gradient profiles in 15-30 min (analytical) and 15-30 min (semipreparative) were applied. Flow rates were 1 mL/min (analytical) and 8-9 mL/min (semipreparative), respectively. UV-detection was carried out at 220 and 254 nm.

Electrospray ionization mass spectrometry, ESI-MS was performed using
  a) a device from Finnigan (Typ LCQ in combination with the HPLC-system Hewlett Packard HP 1100). Columns: a) YMC Hydrosphere C18 (120 Å, 3 μm, 125 mm×2.1 mm), flow rate: 0.55 mL/min; b) YMC-UltraHT-Hydrosphere C18 (120 Å, 2 μm, 50 mm×2.0 mm), flow rate: 0.75 mL/min; c) YMC Octyl C8 (120 Å, 5 μm, 250 mm×2.1 mm), flow rate: 0.35 mL/min. As eluents, mixtures of $H_2O$ and acetonitrile containing 0.1 vol-% formic acid were used for different linear gradients (7 min, 15 min, 40 min).
  or b) a Varian 500-MS IT mass spectrometer (Agilent Technologies, Santa Clara, USA).

Nuclear magnetic resonance (NMR) experiments were performed using the devices AV250, AV360 and DMX500 (Bruker) at 300 K. Chemical shifts (δ) are depicted in parts per million (ppm), as internal reference for $^1H$- and $^{13}C$-shifts, the residual signal of the solvent were used ($CHCl_3$ for $^1H$ (δ=7.26 ppm) and $CDCl_3$ for $^{13}C$ (δ=77.16 ppm); DMSO-$d_5$ for $^1H$ (δ=2.50 ppm) and DMSO-$d_6$ for $^{13}C$ (δ=39.52 ppm). $^{13}C$-NMR-spectra were recorded with $^1H$-broadband decoupling. Datat was processed with the programs MestreC and MestreNova, respectively.

Fluorescence Microscopy experiments were carried out using a BioRevo BZ9000 Fluorescence Microscope (Keyence, Osaka, Japan).

EXAMPLE 2

Synthesis

1. General Procedures

GP1. Loading of Tritylchloridpolystyrene (TCP) Resin

Peptide synthesis was carried out using TCP-resin (0.9 mmol/g) following standard Fmoc-strategy. Fmoc-Xaa-OH (1.2 eq.) were attached to the TCP resin with DIEA (2.5 eq.) in anhydrous DCM (0.8 mL/g resin) at room temperature for 1 h. The remaining trityl chloride groups were capped by addition of 1 mL/g(resin) of a solution of MeOH, DIEA (5:1; vzv) for 15 min. The resin was filtered and washed 5 times with DCM and 3 times with MeOH. The loading capacity was determined by weight after drying the resin under vacuum and ranged from 0.4-0.9 mmol/g.

GP2. Fmoc Deprotection

The resin-bound Fmoc peptide was treated with 20% piperidine in NMP (v/v) for 10 minutes and a second time for 5 minutes. The resin was washed 5 times with NMP.

GP3. N-Methylation Under Mitsunobu Conditions

A solution of triphenylphosphine (5 eq.), DIAD (5 eq.) and MeOH (10 eq.) in dry THF (I mL/g resin) was added to the resin bound Ns protected peptides and shaken at room temperature for 10 minutes. The resin was filtered off, and washed 3 times with dry THF and 3 times with NMP.

GP4. HATU/HOAt Coupling

A solution of Fmoc-Xaa-OH, HATU (2 eq.), HOAt (2 eq.), DIPEA (4 eq.) in NMP (1 mL/g resin) was added to the resin bound peptides and shaken for 3 hours at room temperature and washed 5 times with NMP.

GP5. On-Resin Ns Deprotection

For Ns deprotection, the resin-bound Ns-peptides were stirred in a solution of inercaptoethanol (10 eq.) and DBU (5 eq.) in NMP (I mL/g resin) for 5 minutes. The deprotection procedure was repeated one more time and the resin was washed 5 times with NMP.

GP6. Peptide Cleavage from Resin

For complete cleavage from the resin the peptides were treated three times with a mixture of acetic acid/2,2,2-trifluoroethanol/DCM (3/I/6, v/v/v) at room temperature for half an hour and the solvents were evaporated under reduced pressure.

GP7. Peptide Backbone Cyclization

To a solution of peptide in DMF (I mM peptide concentration) and $NaHCO_3$ (5 eq.), DPPA (3 eq.) was added at RT and stirred over night or until no linear peptide could be observed by ESI-MS. The solvent was evaporated to a small volume under reduced pressure and the peptides precipitated in saturated NaCl solution and washed two times in HPLC grade water.

GP8. Removal of Dde Protecting Group

Dde-protection was carried out using 2% hydrazine in DMF at room temperature. After 30 min, deprotected peptides were precipitated using water (Pbf/tBu/Boc-protected peptides) or diethyl ether (deprotected peptides) and dried in a desiccator before further functionalization.

GP9. Removal of Acid Labile Side Chain Protecting Groups

Cyclized peptides were stirred in a solution of TFA, water and TIPS (95:2.5:2.5; v:v:v) at room temperature for one hour or until no more protected peptide could be observed by ESI-MS and subsequently precipitated in diethyl ether, washed twice with diethyl ether and dried.

GP10. N-Alkylation with Dde-6-Aminohexanol

A solution in NMP containing 2-Nitrobenzenesulfonyl-chloride (o-Ns-Cl, 4 eq.) und sym-Collidine (10 eq.) is added to the resin-bound Peptide and stirred for 15 min. The resin is subsequently washed with NMP (3×) and THF abs. (3×). Afterwards, a solution in THF abs containing $PPh_3$ (5 eq.) and Dde-6-aminohexanol is sucked in the syringe and a solution of DIAD (5 eq.) in a small amount of THF abs. is slowly added. After the resin is incubated for 30 min at RT with this solution, the mixture is removed and the reaction step repeated once again, and washed with THF (3×) und NMP (5×). The o-Ns-protecting group is removed by addition of a solution of Mercaptoethanol (10 eq.) and 1,8-diazabicyclo[5.4.0]undec-7-en (DBU, 5 eq.) in NMP for 5 min (2×). Finally, the resin is washed with NMP (5×).

GP11. Alkyl/Acyl-Quanidinylation in Solution

The orthogonally deprotected peptide P0 is dissolved in DMF and the precursor (A6-A11, B4-B7) (1.5 eq.) and DIPEA (5 eq.) is added subsequently. The solution is stirred at RT for 4 h or until no more starting material is detectable (monitoring by ESI-MS). The peptide is then precipitated in a sat. NaCl-solution (brine) and washed with water (2×).

GP12. Dde-Protection of Linear Aminoalcohols

DdeOH (1.05 eq.) is added to a solution of the linear aminoalcohol (1.0 eq.) in DCM and stirred over night. The solution is washed with 1M aq. HCl (3×) and the combined organic layers dried over $Na_2SO_4$. After evaporation of the solvent in vacuo, the Dde-protected aminoalcohol is obtained as yellow solid.

GP13. Alkylation of N,N'-Di-Boc-1H-pyrazole-1-carboxamidine

N,N'-Di-Boc-1H-pyrazole-1-carboxamidine (1.0 g, 3.2 mmol, 1.0 eq.), $PPh_3$ (0.99 g, 3.8 mmol, 1.2 eq.) und the corresponding alcohol (1.2 eq.) are dissolved in 10 ml THF abs. DIAD (747 µl, 3.8 mmol, 1.2 eq.) is added dropwise to the vigorously stirred solution (at RT) afterwards stirred for 2 h at RT. After the evaporation of the solvent in vacuo, the crude product is purified by flash chromatography.

GP14. Conjugation of Free Amino Function with Unprotected DOTA

DOTA (4 eq.), NHS (5 eq.) and EDCl (5 eq.) are dissolved in water, and DIPEA (8 eq.) are added. After 15 min, the respective peptide (1 eq.) is added in an equal volume of water. Progress of the coupling reaction is monitored using RP-HPLC. Upon completion of the reaction, the solvents are evaporated in vacuo. The residue is resuspended in methanol, the suspension is centrifuged, and the product dissolved in the methanolic supernatant is precipitated using diethyl ether, dried and purified using preparative RP-HPLC.

GP15. Preparation of $^{nat}$Ga-, $^{nat}$Cu-, $^{nat}$Lu- and $^{nat}$Y-DOTA Reference Compounds For the preparation of the $^{nat}$Ga- and $^{nat}$Cu-complexes, equal volumes of a 2 mM solution of $Ga(NO_3)_3$ or $Cu(NO_3)_2$ in 1 M NaOAc buffer and a 2 mM aqueous solution of the respective peptide are mixed and heated to 95° C. for 30 min. The corresponding $^{nat}$Lu and $^{nat}$Y complexes are prepared by adding a 2.5-molar excess of the respective metal chloride dissolved in water to the peptide. Upon heating to 95° C. for 30 min, formation of the respective metal complexes is confirmed using RP-HPLC and ESI-MS.

GP16. Conjugation of Free Amino Function with Cy5-Dyes

To a solution of amine functionalized peptide (1.1 eq) and the respective Cy5 dye analog (1 eq) in DMF, HATU (3 eq) and DIPEA (5 eq) are successively added. Progress of the coupling reaction is monitored using RP-HPLC. Upon completion of the reaction (usually within 30-60 min at RT), the crude product is immediately isolated from the reaction mixture using preparative RP-HPLC.

GP17. Solution Phase Alkylation of Cys Sidechain

The thiol functionalized peptide Pc0 (1 eq) and the respective 2-chloroacetyl functionalized linker unit (C1-C4) or Boc-6-aminohexylbromide (3 eq), respectively, are dissolved in acetonitrile/water (9/1; v/v), and DIPEA (4 eq) is added. The resulting suspension is allowed to stir for 12-18 h at RT. Upon completion of the alkylation reaction, the crude product is precipitated in water, washed and dried in vacuo.

2. Synthesis of Cyclic Pentapeptide Analogs R and R1

CPCR4.3 (R)

CPCR4.3 (c(y-(A/HexGua)a-R-Nal-G), R) was prepared as described previously[52].

c(y-(NHexGua)a-R-Nal-G) (R)

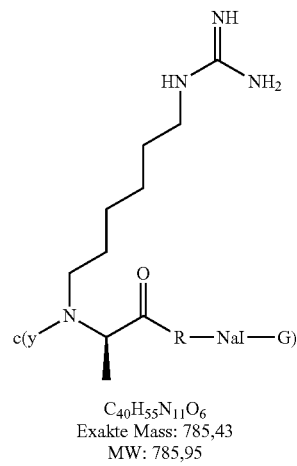

$C_{40}H_{55}N_{11}O_6$
Exakte Mass: 785,43
MW: 785,95

HPLC (15-45% 15 min): $t_R$=8.94 min. MS (ESI): m/z=899.9 $[M+TFA+H]^+$, 786.6 $[M+Na]^+$, 394.1 $[M/2+H]^+$.

Iodo-CPCR4.3(R1)

Synthesis of the unlabeled reference compound iodo-CPCR4.3 was carried out using N-iodosuccinimide (NIS) in acetonitrile/water[53]. Briefly, CPCR4.3 was dissolved in a 1:1 (v/v) mixture of acetonitrile and water to yield a 9 mM solution, and 0.6 eq NIS were added. Upon completion of the reaction (5-10 min at RT), iodo-CPCR4.3 was isolated using semipreparative RP-HPLC.

c(3-iodo-y-(A/HexGua)a-R-Nal-G) (R1)

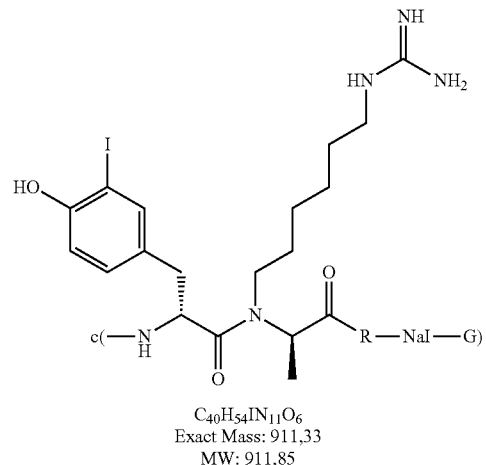

$C_{40}H_{54}IN_{11}O_6$
Exact Mass: 911,33
MW: 911,85

HPLC (15-45% Bin 15 min): $t_R$=11.03 min; MS (ESI); 913.1 $[M+H]^+$, 924.5$[M+Na]^+$, 457.0$[M+2H]^{2+}$ 3. Synthesis of Precursors for Alkylation of the Hexylguanidino-Sidechain in R 2-(1-((2-hydroxyethyl)amino)ethylidene)-5,5-dimethylcyclohexane-1,3-dione (A1)

A1 (1.3 g, 5.8 mmol, 83%) was prepared according to GP12 and obtained as yellow solid.

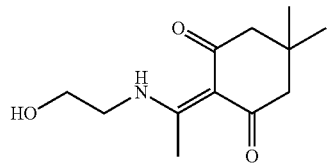

C$_{12}$H$_{19}$NO$_3$
Exact Mass: 225,14
MW: 225,29

$^1$H-NMR (360 MHz, DMSO): δ=13.26 (bs, 1H), 5.00 (bs, 1H), 3.58 (t, J=5.2 Hz, 2H), 3.51-3.46 (m, 2H), 2.48 (s, 3H), 2.26 (s, 4H), 0.94 (s, 6H). $^{13}$C-NMR (90 MHz, DMSO): δ=196.3, 172.9, 106.9, 59.1, 52.4, 45.4, 29.8, 27.9, 17.6. HPLC (10-90%, 15 min): t$_R$=4.40 min, MS (ESI): m/z=226.1 [M+H]$^+$.

2-(1-((2-hydroxypropyl)amino)ethylidene)-5,5-dimethylcyclohexane-1,3-dione (A2)

A2 (1.5 g, 6.3 mmol, 90%) was prepared according to GP12 and obtained as yellow solid.

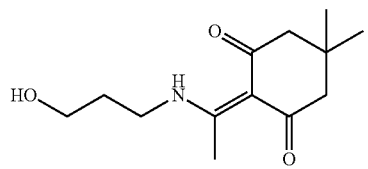

C$_{13}$H$_{21}$NO$_3$
Exact Mass: 239,15
MW: 239,32

$^1$H-NMR (360 MHz, DMSO): δ=13.25 (bs, 1H), 4.30 (bs, 1H), 3.51-3.45 (m, 4H), 2.48 (s, 3H), 2.26 (s, 4H), 1.71 (q, J=5.2 Hz, 2H), 0.94 (s, 6H). $^{13}$C-NMR (90 MHz, DMSO): δ=196.4, 172.9, 106.9, 57.7, 52.3, 31.7, 29.7, 27.9, 17.3. HPLC (10-90%, 15 min): t$_R$=4.73 min, MS (ESI): m/z=240.1 [M+H]$^+$.

2-(1-((2-hydroxybutyl)amino)ethylidene)-5,5-dimethylcyclohexane-1,3-dione (A3)

A3 (1.5 g, 5.9 mmol, 84%) was prepared according to GP12 and obtained as yellow solid.

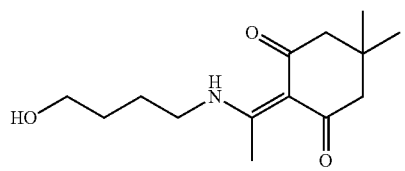

C$_{14}$H$_{23}$NO$_3$
Exact Mass: 253,17
MW: 253,34

$^1$H-NMR ((360 MHz, DMSO): δ=13.27 (bs, 1H), 4.49 (t, J=5.2 Hz, 1H), 3.46-3.40 (m, 4H), 2.48 (s, 3H), 2.27 (s, 4H), 1.63-1.45 (m, 4H), 0.94 (s, 6H). $^{13}$C-NMR (90 MHz, DMSO): δ=196.4, 172.8, 106.9, 52.3, 42.6, 29.8, 29.6, 27.9, 25.3, 17.4. HPLC (10-90%, 15 min): t$_R$=5.01 min, MS (ESI): m/z=254.1 [M+H]$^+$.

2-(1-((2-hydroxypentyl)amino)ethylidene)-5,5-dimethylcyclohexane-1,3-dione (A4)

A4 (1.7 g, 6.4 mmol, 91%) was prepared according to GP12 and obtained as yellow solid.

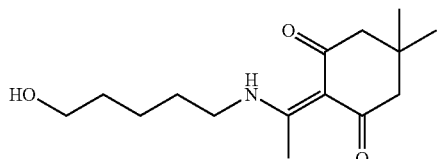

C$_{15}$H$_{25}$NO$_3$
Exact Mass: 267,18
MW: 267,37

$^1$H-NMR ((360 MHz, DMSO): δ=13.26 (bs, 1H), 3.44-3.37 (m, 4H), 2.48 (s, 3H), 2.27 (s, 4H), 1.58 (q, J=5.2 Hz, 2H), 1.47-1.33 (m, 4H), 0.94 (s, 6H). $^{13}$C-NMR (90 MHz, DMSO): δ=196.4, 172.8, 106.9, 60.5, 52.3, 42.7, 32.0, 29.8, 28.4, 27.9, 22.9, 17.4. HPLC (10-90%, 15 min): t$_R$=5.43 min, MS (ESI): m/z=268.2 [M+H]$^+$.

2-(1-((2-hydroxyhexyl)amino)ethylidene)-5,5-dimethylcyclohexane-1,3-dione (A5)

A5 (2.5 g, 8.9 mmol, 85%) was prepared according to GP12 and obtained as yellow solid.

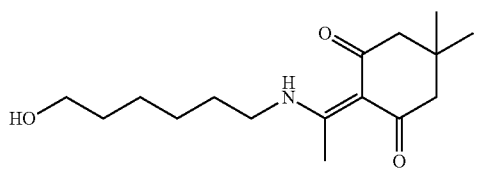

C$_{16}$H$_{27}$NO$_3$
Exact Mass: 281,20
MW: 281,40

$^1$H-NMR ((360 MHz, DMSO): δ=13.26 (bs, 1H), 4.36 (bs, 1H), 3.44-3.36 (m, 4H), 2.47 (s, 3H), 2.26 (s, 4H), 1.57 (q, J=6.2 Hz, 2H), 1.42 (t, J=6.2 Hz, 2H), 1.35-1.29 (m, 4H), 0.94 (s, 6H). $^{13}$C-NMR (90 MHz, DMSO): δ=196.4, 172.8, 106.9, 60.6, 52.3, 42.6, 32.4, 29.8, 28.5, 27.9, 26.2, 25.1, 17.4. HPLC (10-90%, 15 min): t$_R$=6.47 min, MS (ESI): m/z=282.2 [M+H]$^+$.

tert-butyl-(((tert-butoxycarbonyl)imino)(1H-pyrazol-1-yl)methyl)(2-((1-(4,4-dimethyl-2,6-dioxocyclo-hexy-lidene)ethyl)amino)ethyl)carbamate (A6)

Reaction of N,N'-Di-Boc-1H-pyrazole-1-carboxamidine and A1 according to GP13 and subsequent purification by flash chromatography (DCM/EtOAc 2:1) yielded A6 as yellow, viscous oil (0.75 g, 1.45 mmol, 45%).

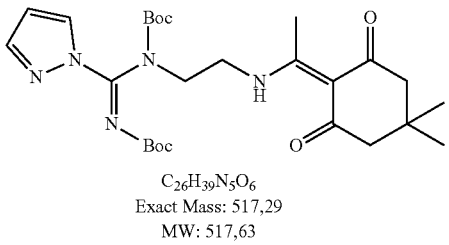 [SMILES: CC(NCCN(C(=O)OC(C)(C)C)/C(=N\C(=O)OC(C)(C)C)n1cccn1)=C1C(=O)CC(C)(C)CC1=O]

C₂₆H₃₉N₅O₆
Exact Mass: 517,29
MW: 517,63

¹H-NMR (360 MHz, DMSO): δ=13.25 (bs, 1H), 8.15 (bs, 1H), 7.87 (d, J=1.5 Hz, 1H), 6.59 (dd, J=2.8 Hz, 1.5 Hz, 1H), 3.85-3.72 (m, 4H), 2.49 (s, 3H), 2.25 (s, 4H), 1.42 (s, 9H), 1.21 (s, 9H), 0.93 (s, 6H). Rf=0.25 (DCM/EtOAc 2:1). HPLC (10-90%, 7 min): t$_R$=4.27 min, MS (ESI): m/z=541.1 [M+Na]⁺, 518.0 [M+H]⁺, 418.0 [M-Boc+H]⁺, 318.1 [M-2Boc+H]⁺.

tert-butyl-(((tert-butoxycarbonyl)imino)(1H-pyrazol-1-yl)methyl)(2-((1-(4,4-dimethyl-2,6-dioxocyclo-hexy-lidene)ethyl)amino)propyl)carbamate (A7)

Reaction of N,N'-Di-Boc-1H-pyrazole-1-carboxamidine and A2 according to GP13 and subsequent purification by flash chromatography (DCM/EtOAc 2:1) yielded A7 as yellow, viscous oil (0.87 g, 1.64 mmol, 51%).

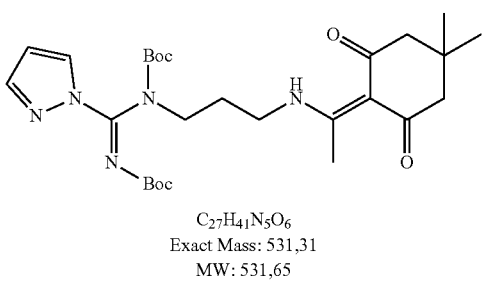 [SMILES: CC(NCCCN(C(=O)OC(C)(C)C)/C(=N\C(=O)OC(C)(C)C)n1cccn1)=C1C(=O)CC(C)(C)CC1=O]

C₂₇H₄₁N₅O₆
Exact Mass: 531,31
MW: 531,65

¹H-NMR (360 MHz, DMSO): δ=13.29 (bs, 1H), 8.22 (bs, 1H), 7.87 (d, J=1.5 Hz, 1H), 6.60 (dd, J=2.8 Hz, 1.5 Hz, 1H), 3.70-3.64 (m, 2H), 3.57-3.50 (m, 2H), 2.46 (s, 3H), 2.26 (s, 4H), 1.98-1.89 (m, 2H), 1.41 (s, 9H), 1.22 (s, 9H), 0.94 (s, 6H). ¹³C-NMR (90 MHz, DMSO): δ=196.2, 173.8, 155.9, 151.8, 143.6, 130.5, 109.5, 106.8, 82.2, 81.7, 52.0, 42.4, 32.9, 29.7, 27.8, 27.8, 27.3, 17.2. Rf=0.42 (DCM/EtOAc 2:1), HPLC (10-90%, 7 min): t$_R$=4.41 min, MS (ESI): m/z=554.1 [M+Na]⁺, 532.1 [M+H]⁺, 432.0 [M-Boc+H]⁺, 332.0 [M-2Boc+H]⁺.

tert-butyl-(((tert-butoxycarbonyl)imino)(1H-pyrazol-1-yl)methyl)(2-((1-(4,4-dimethyl-2,6-dioxocyclo-hexy-lidene)ethyl)amino)butyl)carbamate (A8)

Reaction of N,N'-Di-Boc-1H-pyrazole-1-carboxamidine and A3 according to GP13 and subsequent purification by flash chromatography (DCM/EtOAc 2:1) yielded A8 as yellow, viscous oil (1.29 g, 2.37 mmol, 74%).

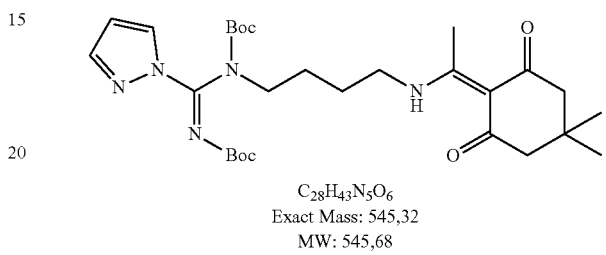

C₂₈H₄₃N₅O₆
Exact Mass: 545,32
MW: 545,68

¹H-NMR (360 MHz, DMSO): δ=13.26 (bs, 1H), 8.18 (bs, 1H), 7.84 (d, J=1.5 Hz, 1H), 6.59 (dd, J=2.8 Hz, 1.5 Hz, 1H), 3.63-3.59 (m, 2H), 3.47-3.40 (m, 2H), 2.46 (s, 3H), 2.26 (s, 4H), 1.73-1.58 (m, 4H), 1.41 (s, 9H), 1.21 (s, 9H), 0.94 (s, 6H). ¹³C-NMR (90 MHz, DMSO): δ=196.3, 172.8, 156.6, 155.9, 151.7, 143.6, 130.4, 109.6, 106.8, 81.9, 81.5, 52.1, 47.7, 42.1, 29.7, 27.8, 27.5, 27.3, 21.7, 17.2. Rf=0.50 (DCM/EtOAc 2:1), HPLC (10-90%, 7 min): t$_R$=4.50 min, MS (ESI): m/z=568.1 [M+Na]⁺, 546.1 [M+H]⁺, 445.9 [M-Boc+H]⁺.

tert-butyl-(((tert-butoxycarbonyl)imino)(1H-pyrazol-1-yl)methyl)(2-((1-(4,4-dimethyl-2,6-dioxocyclo-hexy-lidene)ethyl)amino)pentyl)carbamate (A9)

Reaction of N,N'-Di-Boc-1H-pyrazole-1-carboxamidine and A4 according to GP13 and subsequent purification by flash chromatography (DCM/EtOAc 2:1) yielded A9 as yellow, viscous oil (1.41 g, 2.52 mmol, 79%).

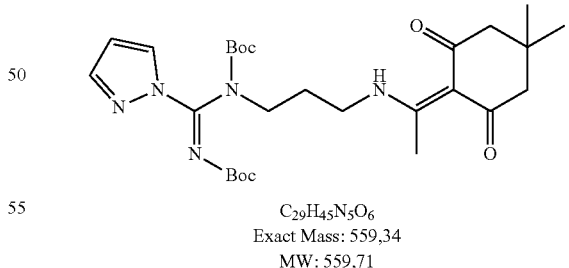

C₂₉H₄₅N₅O₆
Exact Mass: 559,34
MW: 559,71

¹H-NMR (360 MHz, DMSO): δ=13.27 (bs, 1H), 8.17 (bs, 1H), 7.84 (d, J=1.5 Hz, 1H), 6.59 (dd, J=2.8 Hz, 1.5 Hz, 1H), 3.60-3.55 (m, 2H), 3.43-3.37 (m, 2H), 2.46 (s, 3H), 2.26 (s, 4H), 1.68-1.54 (m, 4H), 1.42 (s, 9H), 1.42-1.35 (m, 2H), 1.20 (s, 9H), 0.94 (s, 6H). ¹³C-NMR (90 MHz, DMSO): δ=196.3, 172.8, 156.6, 155.9, 151.7, 143.6, 130.4, 109.6, 106.8, 81.9, 81.5, 52.1, 47.7, 42.1, 29.7, 27.8, 27.5, 27.3, 21.7, 17.2. Rf=0.53 (DCM/EtOAc 2:1), HPLC (10-90%, 7 min): $t_R$=4.61 min, MS (ESI): m/z=582.1 [M+Na]$^+$, 560.1 [M+H]$^+$, 460.1 [M-Boc+H]$^+$, 360.1 [M-2Boc+H]$^+$.

tert-butyl-(((tert-butoxycarbonyl)imino)(1H-pyrazol-1-yl)methyl)(2-((1-(4,4-dimethyl-2,6-dioxocyclohexylidene)ethyl)amino)hexyl)carbamate (A10)

Reaction of N,N'-Di-Boc-1H-pyrazole-1-carboxamidine and A5 according to GP13 and subsequent purification by flash chromatography (DCM/EtOAc 2:1) yielded A10 as yellow, viscous oil (1.41 g, 2.46 mmol, 88%).

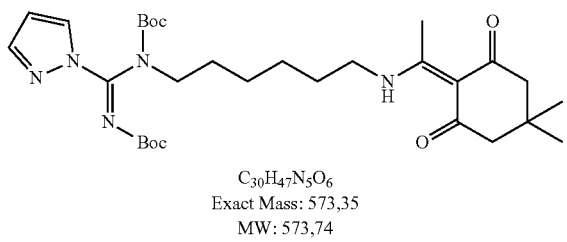 [SMILES: CC(NCCCCCCN(C(=O)OC(C)(C)C)/C(=N\C(=O)OC(C)(C)C)n1cccn1)=C1C(=O)CC(C)(C)CC1=O]

$C_{30}H_{47}N_5O_6$
Exact Mass: 573,35
MW: 573,74

$^1$H-NMR (360 MHz, DMSO): δ=13.26 (t, 1H), 8.18 (bs, 1H), 7.85 (d, 1H), 6.59 (dd, 1H), 3.56 (t, 2H), 3.39 (dt, 2H), 2.46 (s, 3H), 2.26 (s, 4H), 1.65-1.60 (m, 2H), 1.57-1.53 (m, 2H), 1.41 (s, 9H), 1.36-1.31 (m, 2H), 1.20 (s, 9H), 0.94 (s, 6H). $^{13}$C-NMR (90 MHz, DMSO): δ=196.2, 172.6, 156.6, 151.9, 143.5, 130.3, 109.5, 106.8, 82.0, 81.6, 52.3, 48.1, 42.5, 29.7, 28.2, 27.8, 27.5, 27.3, 25.7, 25.5, 17.3. Rf=0.66 (DCM/EtOAc 2:1), HPLC (10-90%, 15 min): $t_R$=10.36 min, MS (ESI): m/z=574.1, [M+H]$^+$, 474.1 [M-Boc+H]$^+$, 374.2 [M-2Boc+H]$^+$.

tert-butyl-(((tert-butoxycarbonyl)imino)(1H-pyrazol-1-yl)methyl)(hex-5-yn-1-yl)carbamate (A11)

Reaction of N,N'-Di-Boc-1H-pyrazole-1-carboxamidine and 5-Hexin-1-ol according to GP13 and subsequent purification by flash chromatography (DCM/EtOAc 2:1) yielded A11 as yellow, viscous oil (0.94 g, 2.40 mmol, 75%).

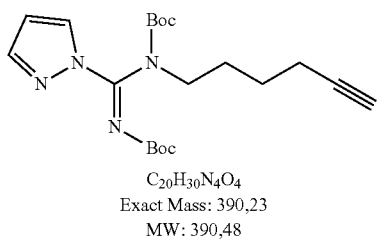 [SMILES: C#CCCCCN(C(=O)OC(C)(C)C)/C(=N\C(=O)OC(C)(C)C)n1cccn1]

$C_{20}H_{30}N_4O_4$
Exact Mass: 390,23
MW: 390,48

Rf=0.53 (DCM/EtOAc 2:1), HPLC (10-90%, 7 min): $t_R$=4.73 min, MS (ESI): m/z=413.1 [M+Na]$^+$, 391.1 [M+H]$^+$, 291.0 [M-Boc+H]$^+$, 189.9 [M-2Boc+H]$^+$.

4. Synthesis of Cyclic Pentapeptide Analogs with Alkylated Hexylguanidino-Residue (P1-P6)

Peptide Intermediate c(y(OtBu)-(NHex-NH$_2$)a-R(Pbf)-Nal-G) (P0)

TCP-resin is loaded with Fmoc-Gly-OH according to GP1 and the linear peptide H-d-Ala-R(Pbf)-Nal-G is synthesized according to standard Fmoc-procedure (GP2 and GP4, respectively). The peptide is subsequently alkylated with Dde-aminohexanol according to GP10 and Fmoc-d-Tyr(OtBu)-OH (GP4) is coupled to the Ns-deprotected peptide. After deprotection (GP2), cleavage from the resin (GP6) and backbone cyclization (GP7) are carried out. Removal of the Dde-protecting group (GP8) is followed by precipitation of the crude peptide in sat. aq. NaCl-solution and lyophilization from a ACN/H$_2$O-solution. P0 (132 mg, 126 μM, 31%) is obtained as yellowish powder (purity>90%).

c(y(OtBu)-(NHex-NH$_2$)a-R(Pbf)-Nal-G) (P0)

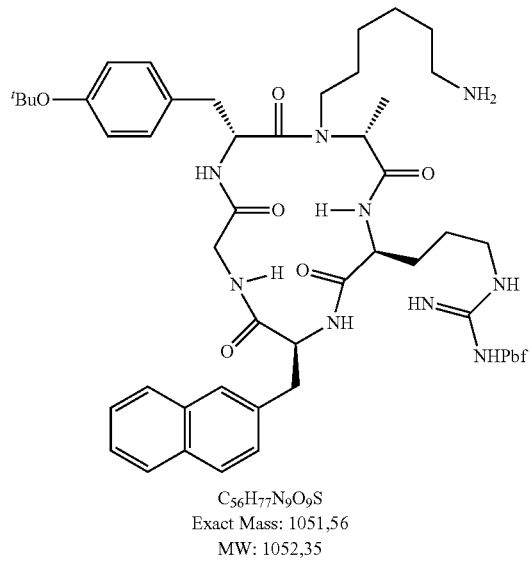

$C_{56}H_{77}N_9O_9S$
Exact Mass: 1051,56
MW: 1052,35

HPLC (10-90% 15 min): $t_R$=7.09 min. MS (ESI): m/z=1074.6 [M+Na]$^+$, 1052.7 [M+H]$^+$.

Acetylated Alkylguanidine Derivatives (P1-P6)

Guanidinylation of P0 with the precursors A6-A10 was carried out according to GP11. After completion of the guanidinylation reaction, the compounds were treated in situ with hydrazine (final concentration 2% v/v) for 5 min. Subsequently, an excess of Ac$_2$O (20 eq.) was added and the mixture stirred for 30 min. Subsequently, the peptides were precipitated in sat. aq. NaCl-solution. Acid labile side chain protecting groups were removed according to GP9, and the crude peptides were purified by semipreparative HPLC to yield compounds P1-P5. P6 was obtained by reacting P0 and A11 according to GP11, precipitation of the crude peptide from water and subsequent side chain deprotection (GP9) and semipreparative purification by HPLC.

c(y-(NHex-Gua-Et-Ac)a-R-Nal-G) (P1)

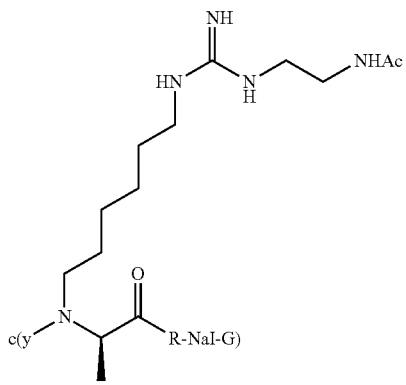

C$_{44}$H$_{62}$N$_{12}$O$_{7}$
Exakte Masse: 870,49
MW: 871,06

HPLC (10-90% 15 min): t$_R$=5.67 min. MS (ESI): m/z=893.6 [M+Na]$^+$. 871.4 [M+H]$^+$.

c(y-(NHex-Gua-But-Ac)a-R-Nal-G) (P3)

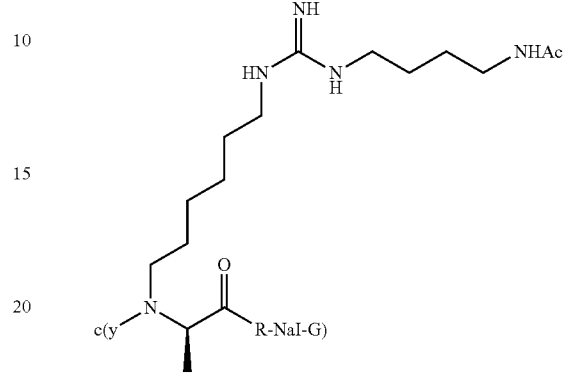

C$_{46}$H$_{66}$N$_{12}$O$_{7}$
Exakte Masse: 898,52
MW: 899,11

HPLC (10-90% 15 min): t$_R$=6.06 min. MS (ESI): m/z=1013.5 [M+TFA+H]$^+$, 899.5 [M+H]$^+$.

c(y-(NHex-Gua-Prop-Ac)a-R-Nal-G) (P2)

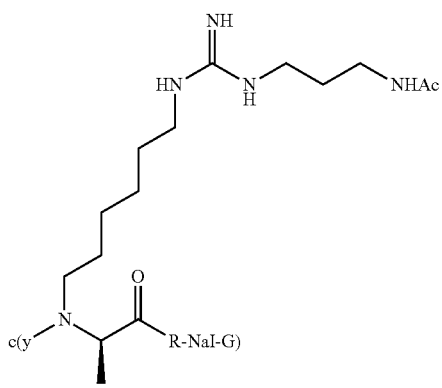

C$_{45}$H$_{64}$N$_{12}$O$_{7}$
Exakte Masse: 884,50
MW: 885,08

HPLC (10-90% 15 min): t$_R$=5.89 min. MS (ESI): m/z=885.6 [M+H]$^+$, 443.3 [M/2+H]$^+$.

c(y-(NHex-Gua-Pent-Ac)a-R-Nal-G) (P4)

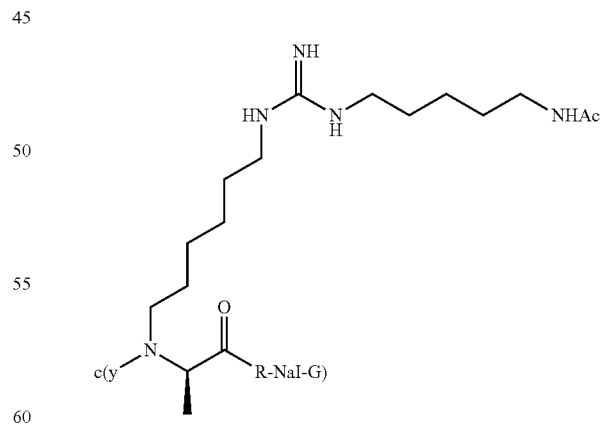

C$_{47}$H$_{68}$N$_{12}$O$_{7}$
Exakte Masse: 912,53
MW: 913,14

HPLC (10-90% 15 min): t$_R$=6.30 min. MS (ESI): m/z=913.6 [M+H]$^+$, 457.3 [M+H]$^+$.

c(y-(NHex-Gua-Hex-Ac)a-R-Nal-G) (P5)

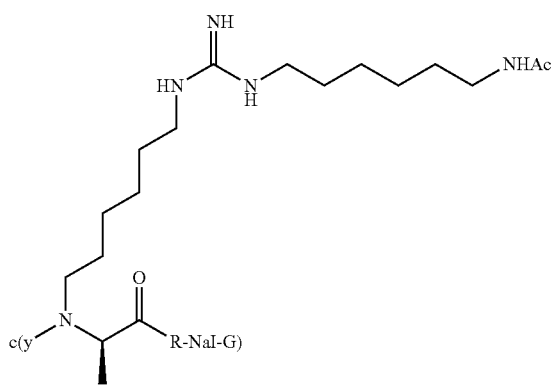

C₄₈H₇₀N₁₂O₇
Exakte Masse: 926,55
MW: 927,17

HPLC (10-90% 15 min): $t_R$=6.69 min. MS (ESI): m/z=1041.5 [M+TFA+H]⁺, 927.6 [M+H]⁺, 464.3 [M/2+H]1.

c(y-(NHex-Gua-Hexin)a-R-Nal-G) (P6)

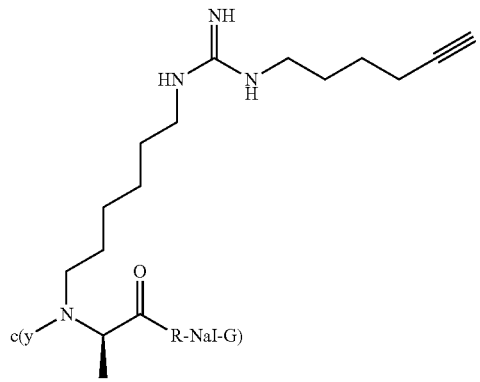

C₄₆H₆₃N₁₁O₆
Exakte Masse: 865,50
MW: 866,08

HPLC (10-90% 15 min): $t_R$=7.08 min. MS (ESI): m/z=866.4 [M+H]⁺, 433.8 [M/2+H]⁺.

5. Synthesis of Functionalized P5 Analogs

Cel-S-Hex-CPCR4.3 (P5a)

To a solution of H₂N-Hex-CPCR4.3 (1 eq.) and Cel(7Ac)-merc-OPfp[54] (1.5 eq) in DMF, DIPEA (3 eq.) were added, and the solution was stirred for 30 min at RT. The crude product was then precipitated using diethyl ether and redissolved in MeOH. For deacetylation, a catalytic amount of KCN was added, and the methanolic peptide solution was stirred overnight at RT. As soon as RP-HPLC-monitoring revealed complete removal of all acetyl protecting groups, the peptide was the precipitated using diethyl ether, washed, dried and purified via preparative RP-HPLC.

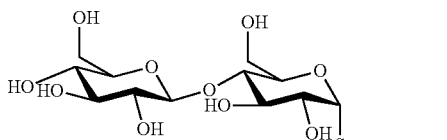

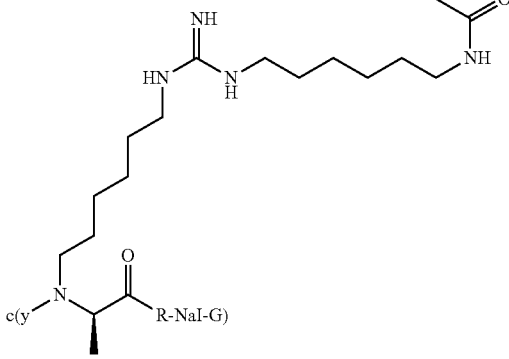

C₆₁H₉₂N₁₂O₁₇S
Exact Mass: 1296,64
MW: 1297,53

HPLC (30-60% in 15 min): $t_R$=7.08 min. MS (ESI): m/z=649.6 [M+2H]²⁺

DOTA-Hex-CPCR4.3 (P5b) (and Ga/Lu Reference Compounds (P5c and P5d)

P0 was fully deprotected according to GP9, and solution phase coupling with DOTA was performed according to GP14.

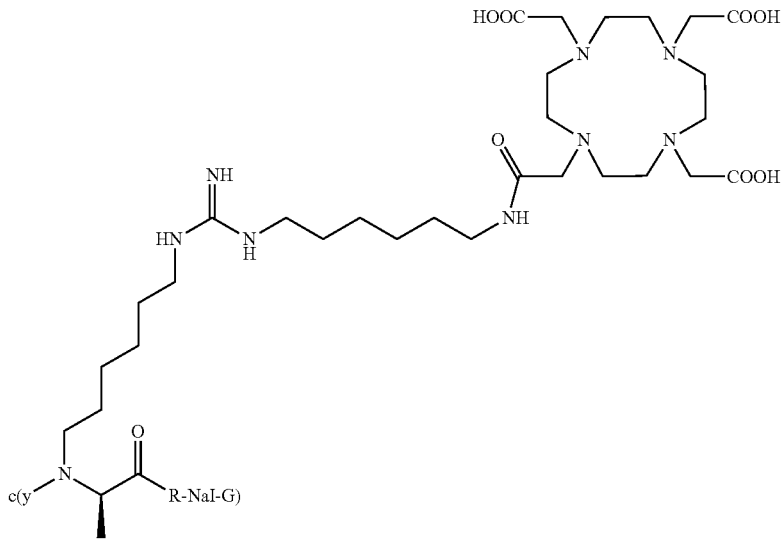

$C_{62}H_{94}N_{16}O_{13}$
Exact Mass: 1270,72
MW: 1271,53

HPLC (15-45% in 15 min): $t_R$=9.3 min. MS (ESI): m/z=1272.2 [M+H]$^+$, 1294.1 [M+Na]$^+$, 636.9 [M+2H]$^{2+}$ The respective $^{nat}$Ga-DOTA- (P5c) and $^{nat}$Lu-DOTA- (P5d) reference compounds were prepared according to GP15.

$^{nat}$Ga-P5b=P5c: MS (ESI): m/z=1339.7 [M+H]$^+$, 670.6 [M+2H]$^{2+}$ $^{nat}$Lu-P5b=P5d: MS (ESI): m/z=1443.8 [M+H]$^+$, 722.7 [M+2H]$^{2+}$ Sulfo$_2$-Cy5-Hex-CPCR4.3 (P5e)

P0 was fully deprotected according to GP9, and solution phase coupling with Sulfo$_2$-Cy5 (free acid) was performed according to GP16.

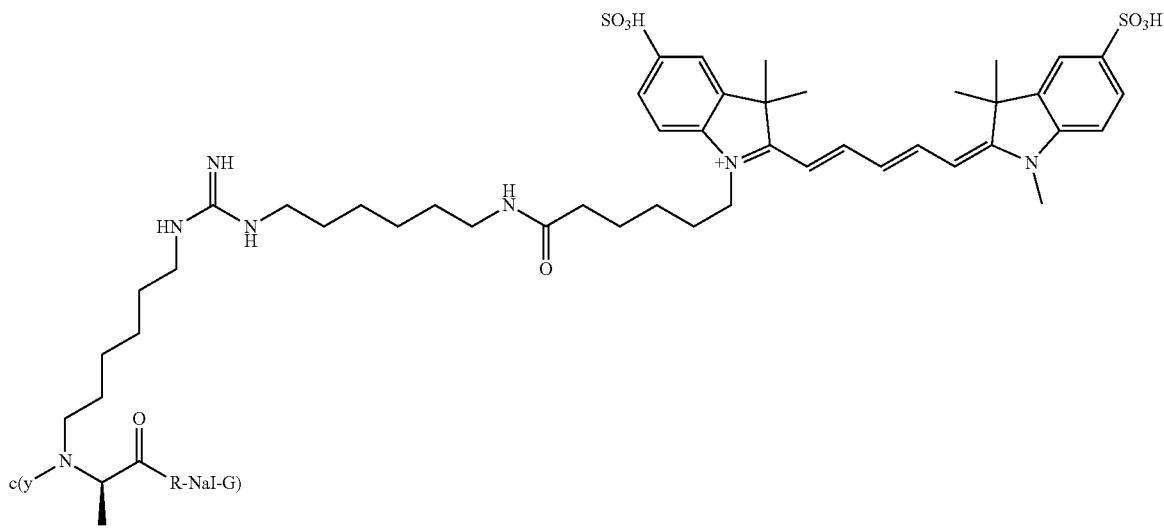

$C_{78}H_{105}N_{14}O_{13}S_2$
Exact Mass: 1509,74
MW: 1510,90

HPLC (15-45% in 15 min): $t_R$=13.2 min. MS (ESI): m/z=1511.0 [M+H]$^+$, 756.3 [M+2H]$^{2+}$.

Sulfo$_2$-Cy5(Hex-CPCR4.3)$_2$ (P5f)

P0 was fully deprotected according to GP9, and solution phase coupling with Sulfo$_2$-Cy5 (symmetric di-acid) was performed according to GP16 using 2.5 eq of P0 and 1 eq of Sulfo$_2$-Cy5 (symmetric di-acid).

Sulfo$_2$-Cy5-PEG$_4$-Hex-CPCR4.3 (P5g)

Upon removal of acid labile side chain protecting groups of P0 according to GP9, the peptide was dissolved in DMF and coupled with Fmoc-NH-PEG$_4$-COOH (1.5 eq) using HOBt (1.5 eq) and TBTU (1.5 eq) as coupling reagents and DIPEA (4.5 eq) as a base. Upon completion of the coupling reaction, the crude peptide was precipitated from diethyl ether and immediately redissolved in piperidine/DMF (20:80, v/v) to remove the Fmoc-protecting group. After 10 min at RT, the deprotected PEG$_4$-conjugate was precipitated using diethyl ether and washed with ether. Coupling with Sulfo$_2$-Cy5 (free acid) was performed according to GP16.

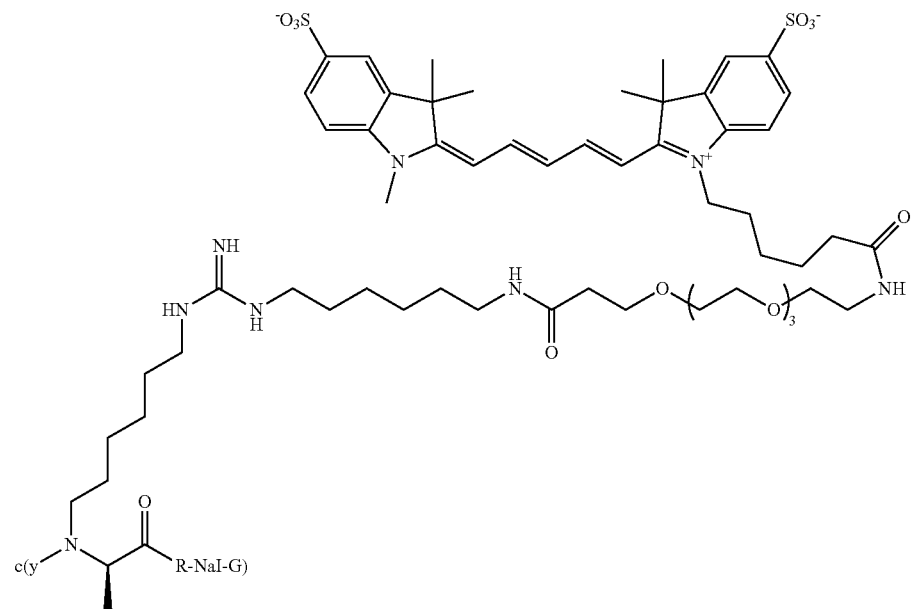

$C_{89}H_{124}N_{15}O_{18}S_2$
Exact Mass: 1754,87
MW: 1756,18

HPLC (20-70% in 15 min): $t_R$=7.15 min.
MS (ESI): m/z=1758.2 [M+H]$^+$, 879.5 [M+2H]$^{2+}$, 890.8 [M+H+Na]$^{2+}$.

Cel-Sulfo$_2$-Cy5-PEG$_4$-Hex-CPCR4.3 (P5h)

Upon removal of acid labile side chain protecting groups of P0 according to GP9, the peptide was dissolved in DMF and coupled with Fmoc-NH-PEG$_4$-COOH (1.5 eq) using HOBt (1.5 eq) and TBTU (1.5 eq) as coupling reagents and DIPEA (4.5 eq) as a base. Upon completion of the coupling reaction, the crude peptide was precipitated from diethyl ether and immediately redissolved in piperidine/DMF (20:80, v/v) to remove the Fmoc-protecting group. After 10 min at RT, the deprotected PEG$_4$-conjugate was precipitated using diethyl ether and washed with ether. Coupling with Cellobiosyl-ethyl-Sulfo$_2$-Cy5 (free acid) was performed according to GP16.

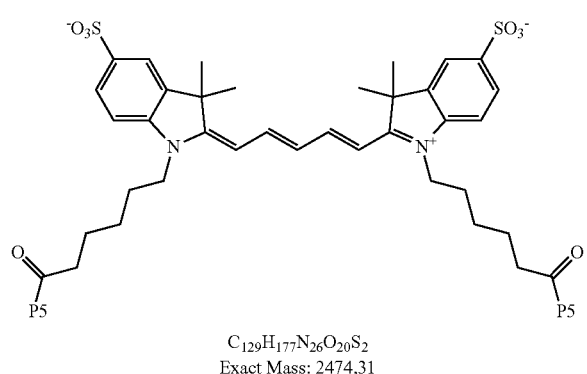

$C_{129}H_{177}N_{26}O_{20}S_2$
Exact Mass: 2474,31
MW: 2476,12

HPLC (25-45% in 15 min): $t_R$=11.5 min. MS (ESI): m/z=1239.3 [M+2H]$^{2+}$, 826.9 [M+3H]$^{3+}$

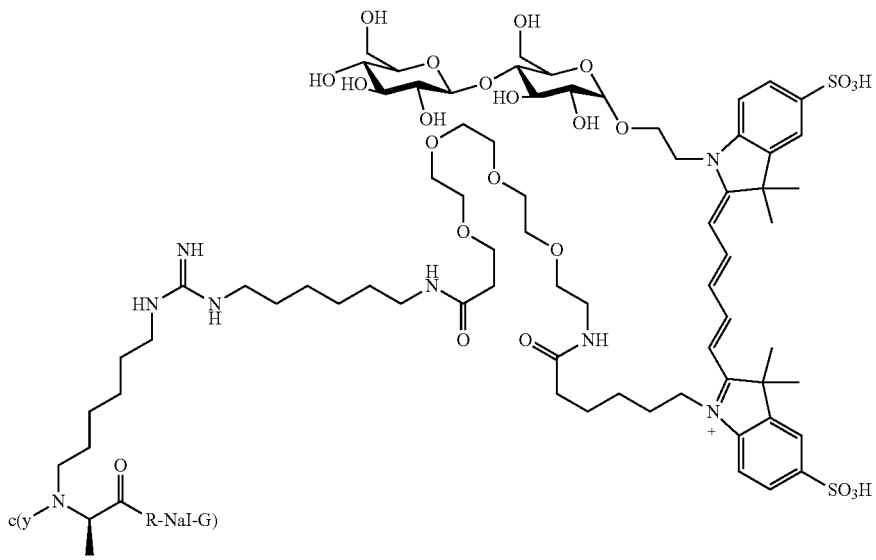

C₁₀₂H₁₄₈N₁₅O₂₉S₂
Exact Mass: 2111,00
MW: 2112,50

HPLC (10-45% in 15 min): $t_R$=11.3 min. MS (ESI): m/z=1057.0 [M+2H]²⁺.

Cel-Sulfo₂-Cy5-arg-Hex-CPCR4.3 (P5i)

Upon removal of acid labile side chain protecting groups of P0 according to GP9, the peptide was dissolved in DMF and coupled with Fmoc-D-Arg(Pbf)-OH (1.5 eq) using HOBt (1.5 eq) and TBTU (1.5 eq) as coupling reagents and DIPEA (4.5 eq) as a base. Upon completion of the coupling reaction, the crude peptide was precipitated from diethyl ether and immediately redissolved in piperidine/DMF (20:80, v/v) to remove the Fmoc-protecting group. After 10 min at RT, the deprotected arg-conjugate was precipitated using diethyl ether and washed with ether. Coupling with Cellobiosyl-ethyl-Sulfo₂-Cy5 (free acid) was performed according to GP16.

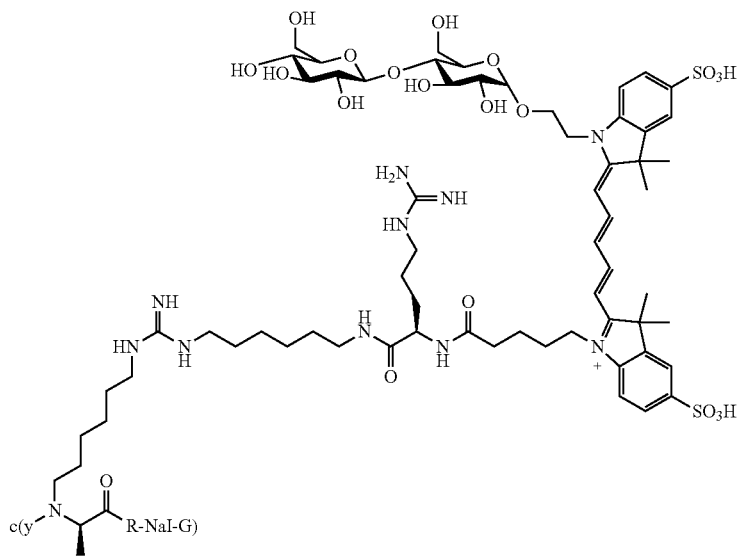

C₉₇H₁₃₉N₁₈O₂₅S₂
Exact Mass: 2019,96
MW: 2021,40

HPLC (10-45% in 15 min): $t_R$=11.1 min. MS (ESI): m/z=1011.8 $[M+2H]^{2+}$.

6-(6-(3-(Bis(benzyloxy)phosphoryl)propanamido)hexanamido)hexanoic acid (D1)

TCP resin was loaded with Fmoc-6-aminohexanoic acid (Fmoc-Ahx-OH) according to GP1. Successive Fmoc-deprotection, coupling with Fmoc-Ahx-OH, Fmoc-deprotection and coupling with Dibenzylphos-phonopropionic acid were carried out according to GP2 and GP4, respectively. After cleavage from the resin (GP6) and lyophilization, D1 was obtained as a white solid (110 mg, 196 μmol, 25%).

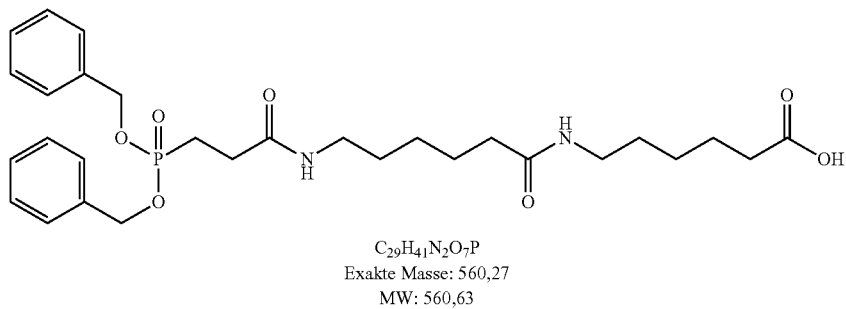 [SMILES: O=C(O)CCCCCNC(=O)CCCCCNC(=O)CCP(=O)(OCc1ccccc1)OCc1ccccc1]

$C_{29}H_{41}N_2O_7P$
Exakte Masse: 560,27
MW: 560,63

HPLC (10-90%, 15 min): $t_R$=6.83 min, MS (ESI): m/z=1120.9 $[2M+H]^+$, 561.2 $[M+H]^+$ Phosphonate-Ahx$_2$-Hex-CPCR4.3 (P5k)

P0 (11.3 mg, 1.0 eq.) was coupled with D1 (5.9 mg, 1.3 eq.) using HOBt (1.5 eq) and TBTU (1.5 eq) as coupling reagents and DIPEA (4.5 eq) as a base. The fully protected peptide was purified by preparative RP-HPLC. The purified peptide was then deprotected according to GP9 and lyophilized to yield P5k as a while solid (3.7 mg, 37%).

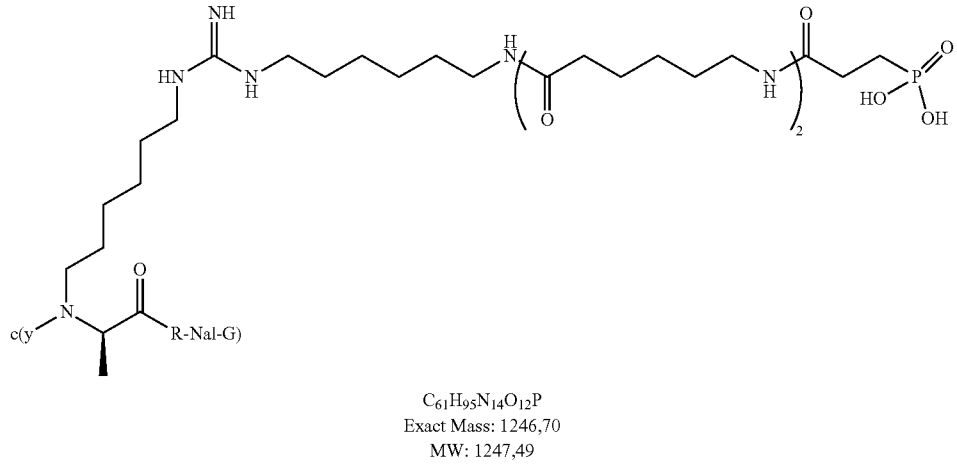

$C_{61}H_{95}N_{14}O_{12}P$
Exact Mass: 1246,70
MW: 1247,49

HPLC (10-90% in 15 min): $t_R$=4.30 min, MS (ESI): m/z=1247.7 $[M+H]^+$, 624.7 $[M+2H]^{2+}$.

21-(Bis(benzyloxy)phosphoryl)-10,19-dioxo-3,6,12, 15-tetraoxa-9,18-diaza-heneicosanoic acid (D2)

TCP resin was loaded with Fmoc-3,6-dioxooctanoic acid (Fmoc-O2Oc-OH) according to GP1. Successive Fmoc-deprotection, coupling with Fmoc-O2Oc-OH, Fmoc-deprotection and coupling with Dibenzylphos-phonopropionic acid were carried out according to GP2 and GP4, respectively. After cleavage from the resin (GP6) and lyophilization, D1 was obtained as a white solid (87 mg, 18%).

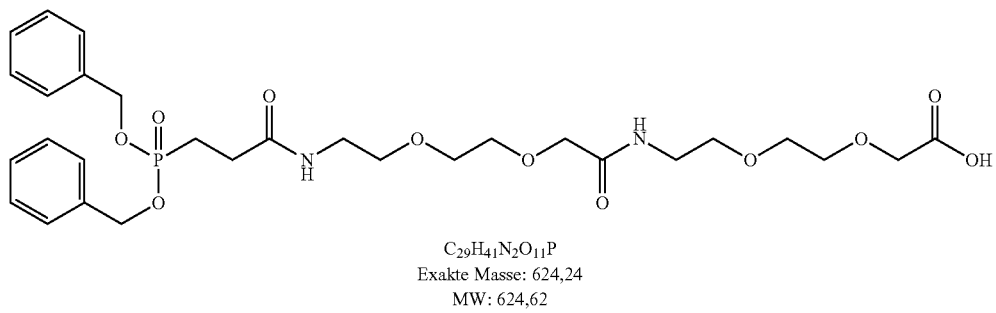 [SMILES: O=C(O)COCCOCCNC(=O)COCCOCCNC(=O)CCP(=O)(OCc1ccccc1)OCc1ccccc1]

C$_{29}$H$_{41}$N$_2$O$_{11}$P
Exakte Masse: 624,24
MW: 624,62

HPLC (10-90% in 15 min): $t_R$=6.26 min. MS (ESI): m/z=625.2 [M+H]$^+$.

Phosphonate-(O2Oc)$_2$Hex-CPCR4.3 (P5m)

P0 (10.5 mg, 1.0 eq.) was coupled with D2 (6.1 mg, 1.3 eq.) using HOBt (1.5 eq) and TBTU (1.5 eq) as coupling reagents and DIPEA (4.5 eq) as a base. The fully protected peptide was purified by preparative RP-HPLC. The purified peptide was then deprotected according to GP9 and lyophilized to yield P5m as a while solid (2.4 mg, 24%).

655 ITK™ Carboxyl Quantum Dots) (0.8 nmol in 100 µl 50 mM borate buffer (pH=8.3)) were diluted with 10 mM borate buffer (pH=7.4) to a total volume of 920 µl. Then, 1-Ethyl-3-(3-dimethylamino-propyl)carbodiimide (800 eq, 640 nmol) in 12.2 µl 10 mM borate buffer and deprotected P0 (40 eq, 32 nmol) dissolved in 64 µl 10 mM borate buffer were added. Consumption of unreacted peptide from the reaction mixture was monitored via RP-HPLC. Upon completion of the coupling reaction (30-60 min at RT), excess coupling reagent was removed from the P5-QD suspension by repeated buffer exchanges using 50 mM borate buffer (pH=8.3) and Amicon Ultra-4 ultrafiltration units with 100 kDa cutoff (4 mL, Millipore). Final reconstitution with 50 mM borate buffer yielded the peptide coated quantum dots P5-QD as a 4 µM suspension. According to the chosen stoichiometry, coating efficiency of the quantum dots was calculated to be app. 40% of reactive carboxylates.

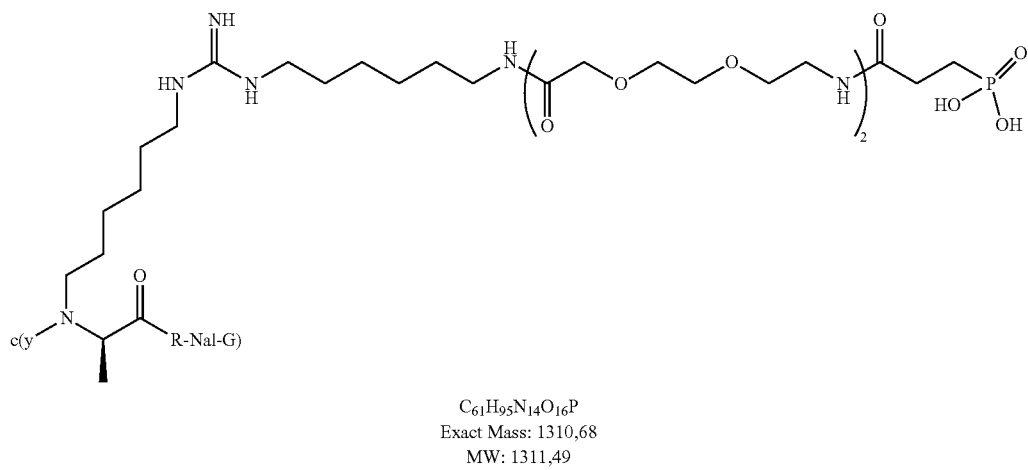

C$_{61}$H$_{95}$N$_{14}$O$_{16}$P
Exact Mass: 1310,68
MW: 1311,49

HPLC (10-90% in 15 min): $t_R$=5.05 min. MS (ESI): m/z=1311.7 [M+H]$^+$, 656.7 [M+2H]$^{2+}$.

Coating of Carboxyl-QDs with P5 (P5-QD)

P0 was deprotected according to GP9, dried and lyophilized. Carboxyl quantum dots (Life technologies, Qdot®

6. Synthesis of Precursors for Acylation of the Hexylguanidino-Sidechain in R

N-(tert-butoxycarbonyl)-S-methylisothiourea (B1)

S-Methylisothiourea-hemisulfate (1.4 g, 10 mmol, 1.0 eq.) and bis-(tert-butyl)-dicarbonate (2.2 g, 10 mmol, 1.0 eq.) are dissolved in a vigorously stirred biphasic solution of DCM and sat. aq. NaHCO₃ for 1 d at RT. After the separation of the two phases, the organic layer is collected and the water phase extracted with DCM (3×). The organic layers are combined and dried over Na₂SO₄ and the solvent removed in vacuo. After purification by flash chromatography (hexane/EtOAc 4:1) yields B1 (1.1 g, 5.8 mmol, 58%) as colorless, viscous solid.

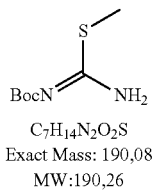

C₇H₁₄N₂O₂S
Exact Mass: 190,08
MW:190,26

¹H-NMR (360 MHz, DMSO): δ=2.30 (s, 3H), 1.39 (s, 9H). ¹³C-NMR (90 MHz, DMSO): δ=165.6, 154.1, 78.3, 28.4, 13.3. R_f=0.30 (Hexan/EtOAc 3:1), HPLC (10-90%, 15 min): t_R=1.31 min, MS (ESI): m/z=190.8 [M+H]⁺.

N-Acetyl Glycine (B2)

Glycine (1.0 g, 13.3 mmol, 1.0 eq.) is dissolved in 30 ml of DMF and subsequently, 4.5 ml DIPEA (26.6 mmol, 2.0 eq.) are added and the solution cooled to 0° C. Afterwards, Ac₂O (3.8 ml, 39.9 mmol, 3.0 eq.) is added dropwise and the solution stirred for 2 h at RT. After addition of 20 ml MeOH the mixture is stirred for 30 min and the solvent removed in vacuo. The crude product is taken up in 20 ml EtOAc and washed with an equal volumina of 1M HCl. The organic layer is dried over Na₂SO₄ and the solvent removed in vacuo. B2 is obtained as white solid (1.2 g, 10.3 mmol, 77%).

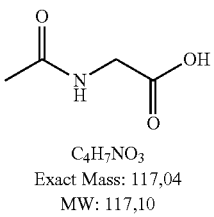

C₄H₇NO₃
Exact Mass: 117,04
MW: 117,10

¹H-NMR (360 MHz, DMSO): δ=12.48 (s, 3H), 8.14 (t, J=5.9 Hz, 1H), 3.71 (d, J=5.9, 2H), 1.84 (s, 3H). ¹³C-NMR (90 MHz, DMSO): δ=171.61, 169.9, 40.8, 22.4. MS (ESI): m/z=140.0 [M+Na]⁺, 117.9 [M+H]⁺.

N-acetyl-6-aminohexanoic Acid (B3)

6-aminohexanoic acid (2.0 g, 15.3 mmol, 1.0 eq.) is dissolved in 50 ml of DMF and 5.2 ml DIPEA (30.6 mmol, 2.0 eq.) are subsequently added and the solution cooled to 0° C. Afterwards, Ac₂O (4.3 ml, 45.9 mmol, 3.0 eq.) is added dropwise and the solution stirred for at RT. After addition of 20 ml MeOH the mixture is stirred for 30 min and the solvent removed in vacuo. The crude product is taken up in 30 ml EtOAc and washed with an equal volumina of 1M HCl. The organic layer is dried over Na₂SO₄ and the solvent removed in vacuo. B3 is obtained as white solid (2.1 g, 12.1 mmol, 79%).

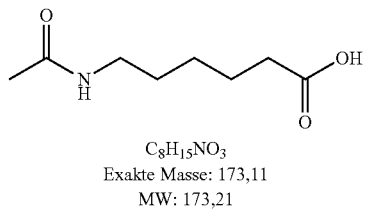

C₈H₁₅NO₃
Exakte Masse: 173,11
MW: 173,21

¹H-NMR (360 MHz, DMSO): δ=11.93 (bs, 1H), 7.79 (bs, 1H), 3.0 (dt, J=6.9 Hz, 5.5 Hz, 2H), 2.19 (t, J=7.2 Hz, 2H), 1.78 (s, 3H), 1.54-1.42 (m, 2H), 1.40-1.33 (m, 2H), 1.29-1.22 (m, 2H). ¹³C-NMR (90 MHz, DMSO): δ=174.4, 168.94, 38.4, 33.6, 28.9, 26.0, 24.3, 22.6. HPLC (10-90%, 7 min): t_R=0.70 min, MS (ESI): m/z=196.0 [M+Na]⁺, 173.9 [M+H]⁺, 347.0 [2M+H]⁺, 369.0 [2M+Na]⁺, 385.1 [2M+K]⁺.

tert-butyl-(acetamido(methylthio)methylene)carbamate (B4)

B1 (250 mg, 1.3 mmol, 1.0 eq.) is dissolved in DMF and DIPEA (440 µl, 2.6 mmol, 2.0 eq.) is added to the stirred solution. Following a dropwise addition of Ac₂O (245 µl, 5.2 mmol, 4.0 eq.) the mixture is stirred for 1 h at RT and taken up in MeOH (2 ml) and stirred for 15 min. The solvent is removed in vacuo and the crude product purified by flash chromatography (hexane/EtOAc 3:1). B4 is obtained as a white solid (241 mg, 1.05 mmol, 80%).

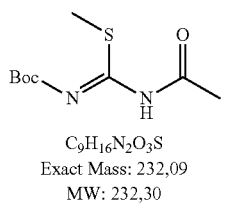

C₉H₁₆N₂O₃S
Exact Mass: 232,09
MW: 232,30

¹H-NMR (360 MHz, DMSO): δ=2.27 (s, 3H), 2.05 (s, 3H), 1.42 (s, 9H). ¹³C-NMR (90 MHz, DMSO): δ=168.44, 161.51, 157.84, 27.77, 23.72, 13.92. R_f=0.62 (Hexane/EtOAc 3:1). HPLC (10-90%, 15 min): t_R=7.13 min, MS (ESI): m/z=232.7 [M+H]⁺, 176.8 [M−tBu+H]⁺.

tert-butyl-((2-acetamidoacetamido)(methylthio)methylene)carbamate (B5)

B1 (130 mg, 0.68 mmol, 1.0 eq.) is dissolved in 4 ml of DMF and a solution containing B2 (95 mg, 0.82 mmol, 1.2 eq.), HATU (312 mg, 0.82 mmol, 1.2 eq.) and DIPEA (230 µl, 1.36 mmol, 2.0 eq.) in 1 ml DMF was added and stirred for 1 h at RT. After evaporation of the solvent, the compound is purified by flash chromatography (EtOAc/MeOH 50:1). B5 (153 mg, 0.44 mmol, 78%) is obtained as white solid.

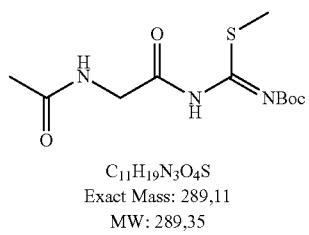

C₁₁H₁₉N₃O₄S
Exact Mass: 289,11
MW: 289,35

Rf=0.28 (EtOAc/MeOH 50:1). HPLC (10-90%, 15 min): $t_R$=5.84 min. MS (ESI): m/z=289.8 [M+H]$^+$, 233.8 [M–tBu+H]$^+$, 189.9 [M–Boc+H]$^+$.

tert-butyl-((6-acetamidohexanamido)(methylthio)methylene)carbamate (B6)

B1 (150 mg, 0.8 mmol, 1.0 eq.) is dissolved in 4 ml of DMF and a solution containing B3 (166 mg, 0.96 mmol, 1.2 eq.), HATU (365 mg, 0.96 mmol, 1.2 eq.) and DIPEA (270 µl, 1.6 mmol, 2.0 eq.) in 1 ml DMF was added and stirred for 1 h at RT. After evaporation of the solvent, the compound is purified by flash chromatography (EtOAc/MeOH 50:1). B6 (210 mg, 0.56 mmol, 76%) is obtained as white solid.

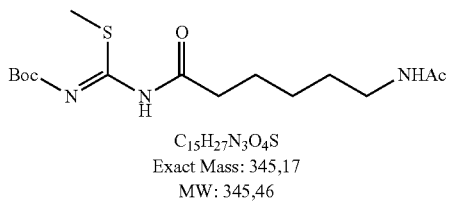 [SMILES: CS/C(=N\C(=O)OC(C)(C)C)NC(=O)CCCCCNC(C)=O]

$C_{15}H_{27}N_3O_4S$
Exact Mass: 345,17
MW: 345,46

$^1$H-NMR (360 MHz, DMSO): δ=7.77 (t, 1H), 2.99 (dt, 2H), 2.33 (t, 2H), 2.28 (s, 3H), 1.77 (s, 3H), 1.54-1.48 (m, 2H), 1.42 (s, 9H), 1.37-1.34 (m, 2H), 1.27-1.21 (m, 2H). $^{13}$C-NMR (90 MHz, DMSO): δ=175.8, 169.4, 161.6, 157.7, 80.4, 38.5, 33.4, 28.9, 27.9, 24.8, 24.2, 22.7, 14.0. $R_f$=0.40 (EtOAc/MeOH 50:1). HPLC (10-90%, 15 min): $t_R$=7.00 min, MS (ESI): m/z=368.0 [M+Na]$^+$, 346.0 [M+H]$^+$, 246.1 [M–Boc+H]$^+$.

tert-butyl-((methylthio)(pent-4-ynamido)methylene)carbamate (B7)

B1 (100 mg, 0.52 mmol, 1.0 eq.) is dissolved in 4 ml of DMF and a solution containing 4-pentinoic acid (61 mg, 0.62 mmol, 1.2 eq.), HATU (230 mg, 0.6 mmol, 1.2 eq.) and DIPEA (170 µl, 1.0 mmol, 2.0 eq.) in 1 ml DMF was added and stirred for 1 h at RT. After evaporation of the solvent, the compound is purified by flash chromatography (DCM/EtOAc 2:1). B7 (111 mg, 0.41 mmol, 79%) is obtained as white solid.

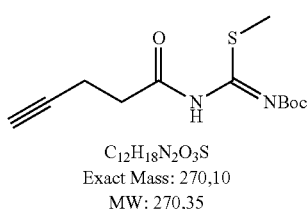

$C_{12}H_{18}N_2O_3S$
Exact Mass: 270,10
MW: 270,35

$^1$H-NMR (360 MHz, DMSO): δ=11.17 (bs, 1H), 2.79-2.77 (m, 1H), 2.57 (t, J=7.1 Hz, 2H), 2.41-2.35 (m, 2H), 2.28 (s, 3H), 1.43 (s, 9H). $^{13}$C-NMR (90 MHz, DMSO): δ=170.0, 161.7, 158.3, 83.4, 80.6, 72.1, 35.3, 28.2, 14.4, 13.7. Rf=0.87 (DCM/EtOAc 2:1). HPLC (10-90%, 15 min): $t_R$=9.24 min, MS (ESI): m/z=271.1 [M+H]$^+$, 171.0 [M–Boc+H]$^+$.

7. Synthesis of Cyclic Pentapeptide Analogs with Acylated Hexylguanidino-Residue (P7-P10)

Guanidinylation of P0 with the acylated precursors (B4-B7, 1.3 eq.) was carried out according to GP11. Upon completion of the reaction the peptides were precipitated in sat. aq. NaCl-solution, treated with a solution containing 90% TFA, 5% DCM, 2.5% H$_2$O and 2.5% TIPS to remove the remaining acid labile side chain protecting groups. Subsequent purification by semipreparative HPLC yielded compounds P7-P10.

c(y-(NHex-Gua-Ac)a-R-Nal-G) (P7)

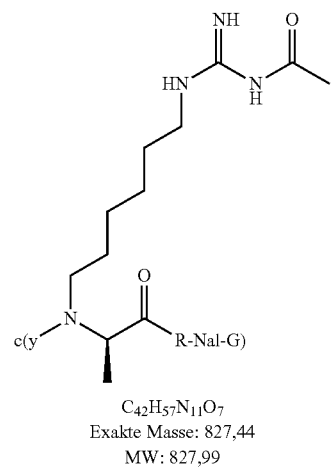

$C_{42}H_{57}N_{11}O_7$
Exakte Masse: 827,44
MW: 827,99

HPLC (5-50% 15 min): $t_R$=9.79 min. MS (ESI): m/z=849.2 [M+Na]$^+$, 414.3 [M+H]$^+$.

c(y-(NHex-Gua-Gly-Ac)a-R-Nal-G) (P8)

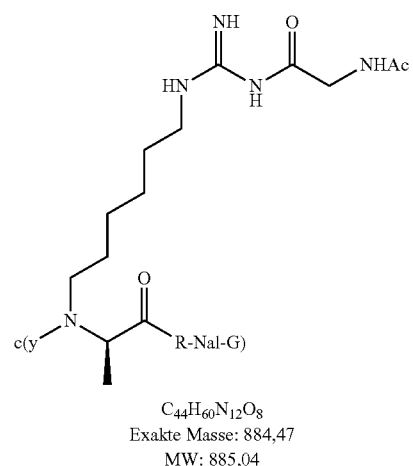

$C_{44}H_{60}N_{12}O_8$
Exakte Masse: 884,47
MW: 885,04

HPLC (10-90% 15 min): $t_R$=5.46 min. MS (ESI): m/z=907.5 [M+Na]$^+$, 885.6 [M+H]$^+$, 443.3 [M/2+H]$^+$.

c(y-(NHex-Gua-Ahx-Ac)a-R-Nal-G) (P9)

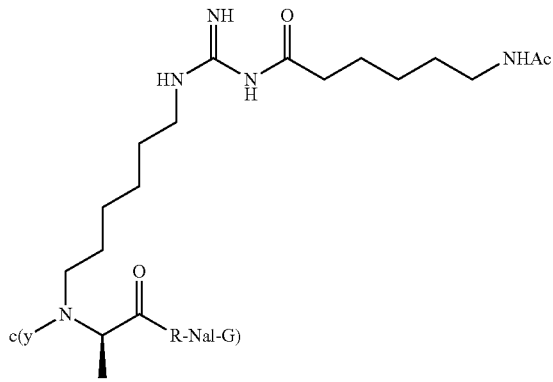

C$_{48}$H$_{68}$N$_{12}$O$_8$
Exakte Masse: 940,53
MW: 941,15

HPLC (10-90% 15 min): t$_R$=5.73 min. MS (ESI): m/z=963.5 [M+Na]$^+$, 471.2 [M/2+H]$^+$.

c(y-(NHex-Gua-Pentinoic acid)a-R-Nal-G) (P10)

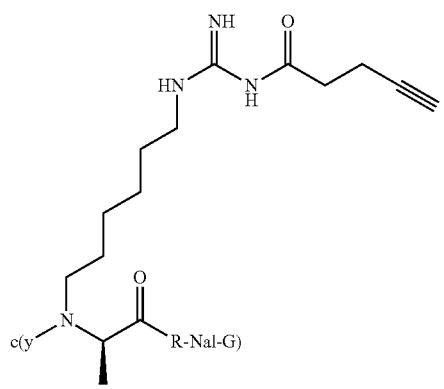

C$_{45}$H$_{59}$N$_{11}$O$_7$
Exakte Masse: 865,46
MW: 866,04

HPLC (10-90% 15 min): t$_R$=3.96 min. MS (ESI): m/z=866.3 [M+H]1, 434.0 [M/2+H]$^+$.

8. Synthesis of the D-Cys-for-Gly Substituted Peptide Scaffold Pc0

Cyclo(ya'(hexylguanidino)Rnalc) (Pc0) was prepared in analogy to the synthesis of peptide R as described previously 55. After assembly of the pentapeptide on H-D-Cys-(2-Cl) Trt resin using solid phase peptide synthesis, including N-alkylation of the D-ala residue, the fully protected peptide was cleaved from the resin and cyclized using diphenylphosphoryl azide. Upon selective removal of the Dde protecting group on the hexylamino sidechain according to GP8, solution phase guanidinylation was performed using 1-H-Pyrazol-1-carboxamidine (10 eq) in DMF and DIPEA (20 eq). Subsequently, the peptide was treated with trifluoroacetic acid, Triisopropylsilane (TIPS) and water (95, 2.5, 2.5; v/v/v) for 40 min and precipitated in diethyl ether to yield crude Pc0 as yellowish powder in sufficient purity for further functionalization.

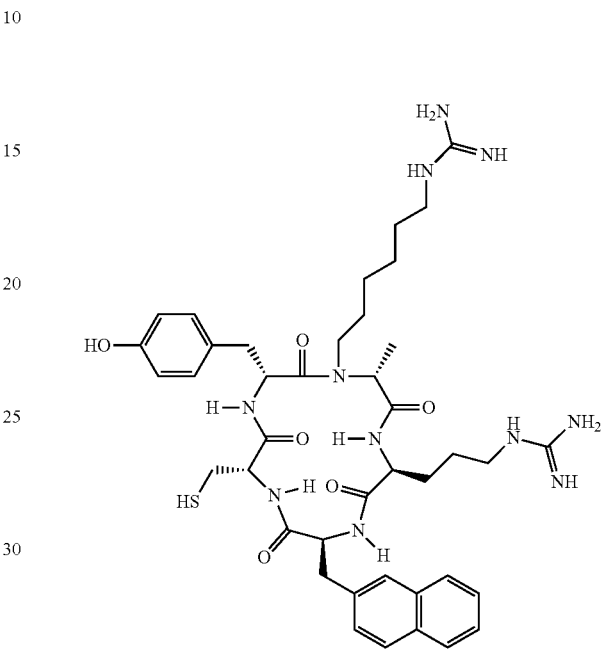

Chemical Formula: C$_{41}$H$_{57}$N$_{11}$O$_6$S
Exact Mass: 831,42
Molecular Weight: 832,04

HPLC (10-90% B in 15 min): t$_R$=11 min. MS (ESI): m/z=832.7 [M+H]$^+$, 854.6 [M+Na]$^+$, 416.9 [M+2H]$^{2+}$

9. Synthesis of Linker Moieties for D-Cys-Functionalization 1-(Fmoc),4-(2-chloroacetyl)-phenylene dimethanamine (C1)

1,4-(Boc)-phenylene dimethanamine (460 mg, 1 eq) was dissolved in 2 mL of tetrahydrofurane (THF), and 5 mL 10% Na$_2$CO$_3$ were added. The resulting suspension was added stepwise to a solution of Fmoc-Cl (500 mg, 1 eq) in THF (2 mL) at 0° C. Upon completion of the reaction, the reaction mixture was diluted with water and THF. The organic solvent was then evaporated in vacuo, leading to the precipitation of the product, which was isolated via centrifugation, washed with water and dried in vacuo. For removal of the Boc protecting group, the dry product was redissolved in TFA/CH$_2$Cl$_2$. After 10 min at RT, the solvents were evaporated in vacuo, affording 1-(Fmoc),4-phenylene dimethanamine as a yellow oil. The crude product was then dissolved in anhydrous CH$_2$Cl$_2$, and DIPEA (2.5 eq) and 2-chloro acetylchloride (1 eq) were added. After 30 min at RT, the solvent was evaporated in vacuo, and the product was recrystallized from ethyl acetate, yielding the product as a white solid.

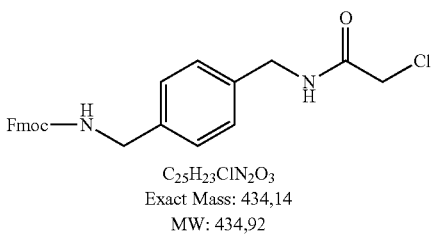

C₂₅H₂₃ClN₂O₃
Exact Mass: 434,14
MW: 434,92

HPLC (40-100% in 15 min): $t_R$=12.26 min. MS (ESI): m/z=457.1 [M+Na]⁺.

1-(Fmoc)-3-(2-chloroacetyl)-phenylene dimethanamine (C2)

The synthesis of C2 was essentially performed as described for C1. The purification of the final product, however, was carried out using SiO₂ column chromatography and a 1:1 mixture (v/v) of ethyl acetate/petroleum ether as eluent.

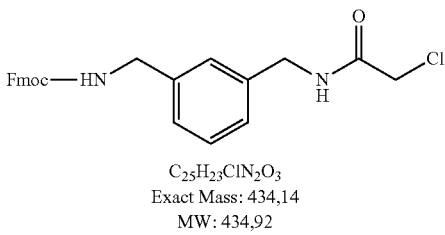

C₂₅H₂₃ClN₂O₃
Exact Mass: 434,14
MW: 434,92

HPLC (40-100% in 15 min): $t_R$=12.42 min. MS (ESI): m/z=457.1 [M+Na]⁺.

Fmoc-(2-chloroacetyl)Lys-CO—NH₂ (C3)

Fmoc-Lys-CO—NH₂ (125 mg, 1 eq) was dissolved in CH₂Cl₂, and DIPEA (2.5 eq) and 2-chloro acetylchloride (1 eq) were added. After 30 min at RT, the product precipitated from the reaction mixture. After filtration, the crude product was recrystallized from ethyl acetate and lyophilized.

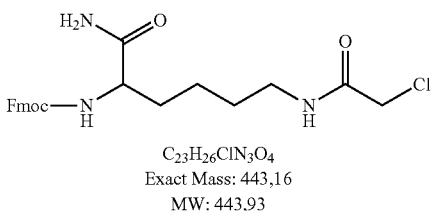

C₂₃H₂₆ClN₃O₄
Exact Mass: 443,16
MW: 443,93

HPLC (40-100% in 15 min): $t_R$=9.68 min. MS (ESI): m/z=443.9 [M+H]⁺, 466.1 [M+Na]⁺.

1-Fmoc-6-(2-chloroacetyl)-hexanediamine (C4)

Fmoc-1,6-hexandiamine (200 mg, 1 eq) was dissolved in acetonitrile/methanol, and DIPEA (2.5 eq) and 2-chloro acetylchloride (1.7 eq) were added. After 60 min at RT and cooling to −20° C. for several hours, the crude product precipitated from the reaction mixture. After filtration, the white crystals were dried and used as such without further purification.

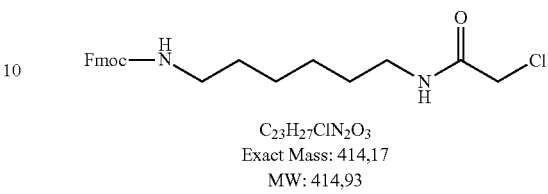

C₂₃H₂₇ClN₂O₃
Exact Mass: 414,17
MW: 414,93

HPLC (40-100 in % 15 min): $t_R$=10.02 min. MS (ESI): m/z=437.2 [M/2+H]⁺.

10. Synthesis of Acetylated D-Cys-for-Gly Substituted Peptides Pc1-Pc5 cyclo[ya'(hexylquanidino)RNalc(CH₂—CO—NH—(CH)₄—CH(CO—NH₂)—NH—Ac)] (Pc1)

Alkylation of Pc0 with C3 was carried out according to GP17. The crude product was then redissolved in piperidine/DMF (80/20, v/v) to remove the Fmoc protecting group on the linker unit. After 10 min at RT, the deprotected peptide was precipitated in water, washed and dried. Acetylation of the free amino function was achieved by dissolving the peptide in a solution of acetic anhydride, DIPEA and DMF (10:5:85; v/v/v) and stirring for 1 h at RT. After workup by precipitation in water, Pc1 was purified using preparative HPLC.

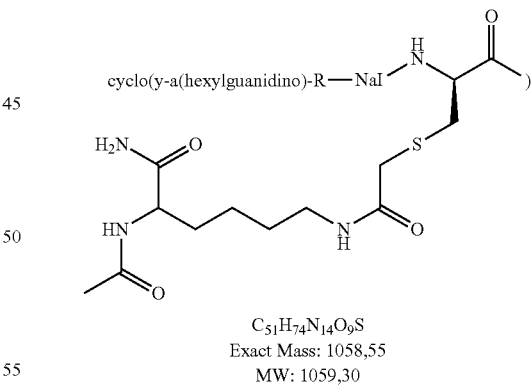

C₅₁H₇₄N₁₄O₉S
Exact Mass: 1058,55
MW: 1059,30

HPLC (15-45% in 15 min): $t_R$=6.8 min. MS (ESI): m/z=1059.8 [M+H]⁺, 1081.8 [M+Na]⁺, 1097.6 [M+K]⁺ cyclo[ya'(hexylquanidino)RNalc(CH₂—CO—NH—(CH₂)₆—NH—Ac)] (Pc2)

Alkylation of Pc0 with C4 was carried out according to GP17. Subsequent Fmoc-deprotection and N-acetylation were carried out as described for Pc1.

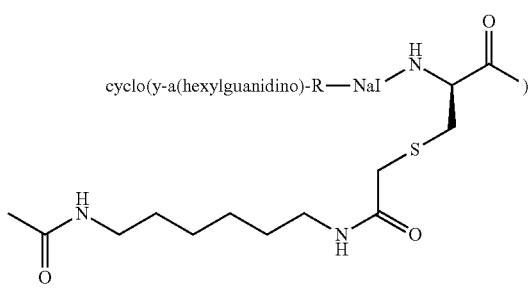

C₅₁H₇₅N₁₃O₈S
Exact Mass: 1029,56
MW: 1030,30

HPLC (15-45% in 15 min): $t_R$=9 min. MS (ESI): m/z=1030.7 [M+H]⁺, 1052.6 [M+Na]⁺.

cyclo[ya'(hexylquanidino)RNalc(—(CH₂)₆—NH—Ac)] (Pc3)

Alkylation of Pc0 with Boc-6-aminohexylbromide was carried out according to GP17. Subsequent Boc-deprotection was carried out according to GP9, and N-acetylation was carried out as described for Pc1.

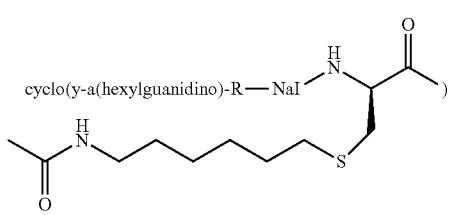

C₄₉H₇₂N₁₂O₇S
Exact Mass: 972,54
MW: 973,25

HPLC (15-45% in 15 min): $t_R$=10 min. MS (ESI): m/z=973.6 [M+H]⁺, 995.5 [M+Na]⁺ cyclo[ya'(hexylquanidino)RNalc(—CH₂—CO—NH—CH₂-(p-aryl)-CH₂—NH—Ac)] (Pc4)

Alkylation of Pc0 with C1 was carried out according to GP17. Subsequent Fmoc-deprotection and N-acetylation were carried out as described for Pc1.

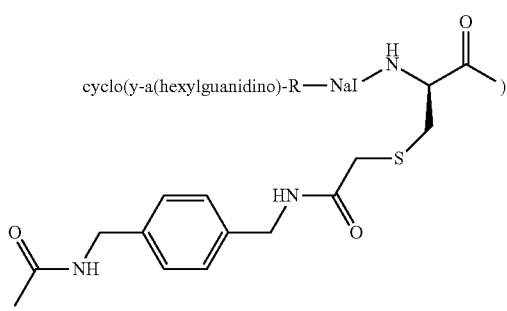

C₅₃H₇₁N₁₃O₈S
Exact Mass: 1049,53
MW: 1050,29

HPLC (15-45% in 15 min): $t_R$=8.7 min. MS (ESI): m/z=1050.6 [M+H]⁺, 1072.6 [M+Na]⁺, 525.8 [M+2H]²⁺.

cyclo[ya'(hexylquanidino)RNalc(—CH₂—CO—NH—CH₂-(m-aryl)-CH₂—NH—Ac)] (Pc5)

Alkylation of Pc0 with C2 was carried out according to GP17. Subsequent Fmoc-deprotection and N-acetylation were carried out as described for Pc1.

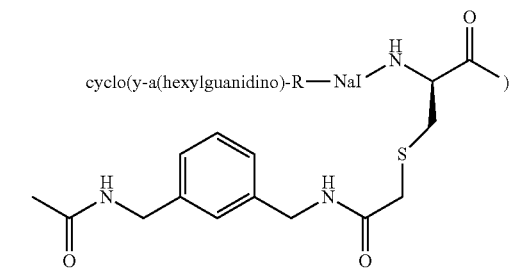

C₅₃H₇₁N₁₃O₈S
Exact Mass: 1049,53
MW: 1050,29

HPLC (15-45% in 15 min): $t_R$=8.8 min. MS (ESI): m/z=1050.8 [M+H]⁺, 1072.7 [M+Na]⁺, 525.9 [M+2H]²⁺.

cyclo[ya'(hexylquanidino)RNalc(—CH₂—CO—NH—CH₂-(m-aryl)-CH₂—NH-DOTA)] (Pc5a)

Alkylation of Pc0 with C2 was carried out according to GP17. The crude product was then redissolved in piperidine/DMF (80/20, v/v) to remove the Fmoc protecting group on the linker unit. After 10 min at RT, the deprotected peptide was precipitated in water, washed and dried. Coupling of DOTA to the free amino function was carried out according to GP14.

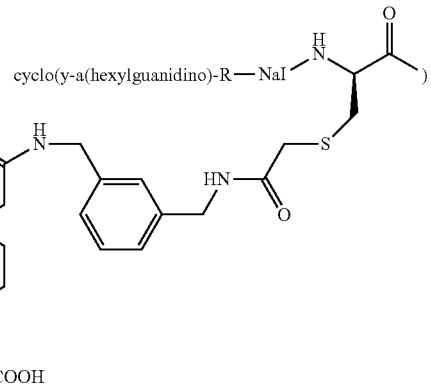

C₆₇H₉₅N₁₇O₁₄S
Exact Mass: 1393,70
MW: 1394,66

HPLC (15-35% in 15 min): $t_R$=11.9 min. MS (ESI): m/z=1396.1 [M+H]⁺, 698.4 [M+2H]2+.

cyclo[ya'(hexylguanidino)RNalc(—CH$_2$—CO—
NH—CH$_2$-(m-aryl)-CH$_2$—NH-$^{nat}$Ga-DOTA)]
(Pc5b)

The $^{nat}$Ga-complex of Pc5a was prepared according to GP15.

HPLC (15-35% in 15 min): $t_R$=12.5 min. MS (ESI): m/z=1463.0 [M+H]$^+$, 732.1 [M+2H]$^{2+}$.

cyclo[ya'(hexylguanidino)RNalc(—CH$_2$—CO—
NH—CH$_2$-(m-aryl)-CH$_2$—NH-$^{nat}$Lu-DOTA)]
(Pc5c)

The $^{nat}$Lu-complex of Pc5a was prepared according to GP15.

HPLC (15-35% in 15 min): $t_R$=11.7 min. MS (ESI): m/z=1567.0 [M+H]$^+$, 784.5 [M+2H]$^{2+}$.

cyclo[ya'(hexylguanidino)RNalc(—CH$_2$—CO—
NH—CH$_2$-(m-aryl)-CH$_2$—NH-$^{nat}$Cu-DOTA)]
(Pc5d)

The $^{nat}$Cu-complex of Pc5a was prepared according to GP15.

HPLC (15-35% in 15 min): $t_R$=12.9 min. MS (ESI): m/z=1456.1 [M+H]$^+$, 729.1 [M+2H]$^{2+}$.

Coating of Carboxyl-QDs with Pc5 (Pc5-QD)

Alkylation of Pc0 with C2 was carried out according to GP17. The crude product was then redissolved in piperidine/DMF (80/20, v/v) to remove the Fmoc protecting group on the linker unit. After 10 min at RT, the deprotected peptide was precipitated in water, washed, dried and lyophilized. Carboxyl quantum dots (Life technologies, Qdot® 655 ITK™ Carboxyl Quantum Dots) (0.8 nmol in 100 µl 50 mM borate buffer (pH=8.3)) were diluted with 10 mM borate buffer (pH=7.4) to a total volume of 920 µl. Then, 1-Ethyl-3-(3-dimethylamino-propyl)carbodiimide (800 eq, 640 nmol) in 12.2 µl 10 mM borate buffer and deprotected peptide (40 eq, 32 nmol) dissolved in 64 µl 10 mM borate buffer were added. Consumption of unreacted peptide from the reaction mixture was monitored via RP-HPLC. Upon completion of the coupling reaction (30-60 min at RT), excess coupling reagent was removed from the Pc5-QD suspension by repeated buffer exchanges using 50 mM borate buffer (pH=8.3) and Amicon Ultra-4 ultrafiltration units with 100 kDa cutoff (4 mL, Millipore). Final reconstitution with 50 mM borate buffer yielded the peptide coated quantum dots Pc5-QD as a 4 µM suspension. According to the chosen stoichiometry, coating efficiency of the quantum dots was calculated to be app. 40% of reactive carboxylates.

EXAMPLE 3

Further Materials and Methods

1. Radiolabeling 1.1. Radioiodination

All peptides were radioiodinated using the IodoGen® method. Briefly, 100-200 µg of peptide were dissolved in 5-10 µL of DMSO. This solution was diluted with 0.5 mL TRIS iodination buffer (25 mM Tris-HCl, 0.4 M NaCl, pH 7.5) and transferred to an Eppendorf reaction tube coated with 150 µg of IodoGen®. Upon addition of [$^{125}$I]NaI (18-20 MBq, Hartmann Analytic, Braunschweig, Germany) or [$^{123}$I]NaI (220 MBq, GE Healthcare, Braunschweig, Germany), the reaction vessel was briefly vortexed and the labeling reaction was allowed to proceed for 15 min at RT. The peptide solution was then removed from the insoluble oxidizing agent. Separation of the labeled products from unlabeled precursor was achieved using gradient RP-HPLC. For in vitro binding studies, the HPLC product fraction was used as such and diluted to the required concentration using the respective assay medium. For biodistribution experiments, the respective product fraction was diluted with water and passed onto a SepPak Plus C-18 cartridge (Waters, Eschborn, Germany). The cartridge was washed with water, and the immobilized radiopeptide was then eluted using 1 ml of acetonitrile. The solvent was removed by bubbling an argon stream through the radioligand solution at 90° C. for 20 min. The radioiodinated peptides were then reconstituted to an activity concentration of app. 1 MBq/100 µL using PBS and were used as such for the in vivo animal study.

1.2. $^{68}$Ga-Labeling $^{68}$Ga was obtained by elution of a $^{68}$Ge/$^{68}$Ga generator with SnO$_2$ matrix (iTHEMBA LABS, South Africa) with 1 M HCl (5.5 mL) and immobilized on a strong cationic exchanger cartridge (SCX—Chromafix, size M, Macherey-Nagel, Duren, Germany).

For animal studies, $^{68}$Ga-pentixafor was prepared on a Gallelut$^+$ system in analogy to a previously published $^{68}$Ga labeling procedure[56] (SCINTOMICS GmbH, Germany). Briefly, $^{68}$Ga-generator eluate fractions (1.25 mL, 600-800 MBq, buffered to pH 3.3 with 900 µL of a solution of 14.4 g HEPES in 12 mL water) were reacted with 3.5 nmol of the respective DOTA-peptide (P5b, Pc5a) for 5 min. The radiochemical purity was always >99% as confirmed by thin layer chromatography (TLC) and high performance liquid chromatography (HPLC). Addition of 1 mL PBS and concentration in vacuo to 1 mL total volume yielded solvent-free formulations with specific activities ranging from 100-150 MBq/nmol.

1.3. $^{177}$Lu-Labeling

For $^{177}$Lu-labeling, the respective DOTA peptides (P5b, Pc5a) were dissolved in water to yield a 1 mM solution. Of this solution, the required volume was added to $^{177}$LuCl$_3$ in 0.04 M HCl (itg Isotope Technologies Garching, Garching, Germany; activity concentration: 370 MBq/500 µl) to achieve a peptide-to-$^{177}$Lu-activity ratio of 1 nmol peptide per 225 MBq $^{177}$LuCl$_3$. To this mixture, 1 M NH$_4$OAc was added (calculated to be 10% of total reaction volume), and the mixture was heated to 95° C. for 20 min. Upon cooling, the radiochemical purity was determined using thin layer chromatography (TLC) (usually >98%). For in vitro and in vivo studies, the reaction mixture was diluted with PBS to the desired activity concentration and used as such for the experiments.

2. Determination of Lipophilicity

To a solution of app. 2 kBq of radiolabeled peptide in 500 µL of PBS (pH 7.4), 500 µL of octanol were added (n=6). Vials were vortexed vigorously for 3 min. To achieve quantitative phase separation, the vials were centrifuged at 14,600×g for 6 min in a Biofuge 15 (Heraeus Sepatech, Osterode, Germany). The activity concentrations in 100

µL-samples of both the aqeuous and the organic phase were measured in a γ-counter. Both the partition coefficient $P_{OW}$, which is defined as the molar concentration ratio of a single species A between octanol and an aqueous phase at equilibrium, and log $P_{OW}$, which is an important parameter used to characterize lipophilicity of a compound, were calculated.

3. In Vitro Evaluation

3.1. Cell Culture

Jurkat human T lymphocyte cells were maintained in RPMI 1640 medium supplemented with 10% fetal calf serum (FCS). Daudi cells (human Burkitt's B-cell lymphoma) were grown in RPMI-1640 medium supplemented with 10% FCS, 2 mM L-glutamine, 1% non-essential amino acids (NEA), 50 µM β-mercaptoethanol and 100 units/mL of penicillin/streptomycin. Chem-1 cells stably transfected with hCXCR4 (HTS004C ChemiScreen™ cells, Merck Millipore, Darmstadt, Germany) were cultured in DMEM medium supplemented with 10% FCS, 1% NEA and 1% HEPES (1M). Ep-Myc1080 mouse B-cell lymphoma cells 57 were grown in RPMI 1640 medium supplemented with 20% FCS, 1% NEA, 1% 100 U/ml penicillin and 100 mg/ml streptomycin and 0.1% 2-Mercaptoethanol. C6 rat glioma cells (kindly supplied by Prof. Rolf Mentlein, Anatomical Institute, University Kiel, Germany) were grown in DMEM medium containing 10% FCS, 2 mM L-glutamine and 100 units/mL of penicillin/streptomycin.

All cell lines were cultured at 37° C. in a humidified 5% $CO_2$ atmosphere. Media and supplements were obtained from Biochrom (Berlin, Germany) or Gibco (life technologies, Darmstadt, Germany). In the assay medium used for internalization studies, FCS was replaced by 5% bovine serum albumin (BSA; Sigma, St. Louis, USA). For cell counting, a Countesse automated cell counter (Invitrogen, Carlsbad, USA) was used.

3.2. Determination of $IC_{50}$

For the determination of hCXCR4-affinity, competition binding experiments were performed using Jurkat cells and [$^{125}$I]FC131 or [$^{125}$I]R1 as radioligand. Affinity to mCXCR4 and rCXCR4 was determined using Ep-Myc1080 mouse B-cell lyphoma cells[5] or C6 rat glioma cells, respectively, and [$^{125}$I]R1 as the radioligand.

For $IC_{50}$ determination using Jurkat or Ep-Myc1080 cells, samples containing $2 \times 10^5$ cells (or $4 \times 10^5$ cells; exact cell number used in the respective evaluations is given in the results section) in Hank's balanced salt solution (HBSS)/1% Bovine Serum Albumin (BSA) were incubated with 100.000 cpm of the respective radioligand (approx. 0.1 nM) in the presence of increasing concentrations ($10^{-11}$ to $10^{-5}$ M) of the respective peptide of interest (n=3 per concentration). The total sample volume was 250 µL. After incubation at room temperature (RT) for 120 min with gentle agitation (200 mot/min), the tubes were centrifuged (5 min, 450 g, Megafuge 1.0, Heraeus Thermo Scientific) and the supernatant was carefully removed. After washing twice with 400 µL of cold HBSS, the amount of cell-bound radioligand was quantified using a γ-counter.

In the case of the adherent C6 glioma cells, cells were harvested using Trypsin/EDTA (0.05% and 0.02%) in PBS one day prior to the experiment, centrifuged and resuspended with culture medium to a concentration of app. 150.000 cells/mL. The suspension was transferred into PLL-coated twenty-four-well plates (1 mL/well, Greiner, Solingen. Germany) and placed in the incubator overnight. On the day of the experiment, the culture medium was removed and the cells were washed with 250 µL of HBSS before being left to equilibrate in 200 µL of HBSS (1% BSA) at 37° C. for a minimum of 15 min before the experiment. Then, cells were incubated with 100.000 cpm of the respective radioligand (approx. 0.1 nM) in the presence of increasing concentrations ($10^{-11}$ to $10^{-5}$ M) of the respective compound of interest (n=3 per concentration). The total sample volume was 250 µL. After incubation at room temperature (RT) for 120 min, the supernatant was removed and cells were washed twice with 200 µL of cold HBSS. Then, cells were lysed using 250 µL of 1 N NaOH, the lysate was transferred to vials and combined with 250 µL of HBSS used for rinsing the wells. Quantification of the amount of free and bound activity was performed in a γ-counter.

$IC_{50}$ values were calculated using PRISM 6 software (Graph Pad Software, San Diego, CA) using a three-parameter sigmoidal dose response curve fit.

3.3. Internalization Studies in hCXCR4-Expressing Chem-1 Cells

On the day of the experiment, the culture medium was removed, and the cells were washed with 250 µL of HBSS (1% BSA) before being left to equilibrate in 200 µL of assay medium (RPMI+5% BSA) at 37° C. for a minimum of 15 min before the experiment. Then, 25 µL/well of either assay medium (Control) or of a 1 mM solution of AMD3100 in HBSS (determination of non-specific binding) were added (n=3, respectively, for each time point), followed by the addition of 25 µL of the radioligand of interest in assay medium. The final radioligand concentration was 0.2-1 nM in all internalization assays.

Upon incubation at 37° for different time points up to 60 min, the incubation medium was removed, and cells were rinsed twice with 250 µL of HBSS. The wash medium was combined with the supernatant of the previous step. This fraction represents the amount of free radioligand. To remove surface bound (acid releasable) radioactivity, the cells were then incubated with 250 µL of ice cold acid wash buffer (0.02 M NaOAc buffered with AcOH to pH=5). After removal of the acid wash buffer, the cells were thoroughly rinsed with another 250 µL of ice cold acid wash buffer. Both acid wash fractions were combined. The internalized activity was released by incubation with 250 µL of 1 N NaOH, transferred to vials and combined with 250 µL of PBS used for rinsing the wells. Quantification of the amount of free, acid-releasable and internalized activity was performed in a γ-counter.

3.4. Cell Binding and Internalization Studies Using Fluorescent Ligands and Coated QD's Chem-1 cells (125.000/well) were seeded on glass cover slips in well plates 24 h prior to the experiments. Then, the culture medium was removed and the cells were washed with 250 µL of HBSS (1% BSA) before being left to equilibrate in 200 µL of assay medium (DMEM/Ham's F12+5% BSA) at 4° or 37° C. for a minimum of 15 min before the experiment. In the case of Daudi or Ep-Myc 1080 cells, a suspension of the respective cells in assay medium (DMEM/Ham's F12+5% BSA, 100.000 cells/200 µl) was prepared. Then, the cells were either incubated with the respective fluorescent ligand alone or coincubated with fluorescent ligand (final ligand concentration is specified in the figure captions), 2 µg/ml Hoechst (1 mg/ml, 0.5 µl) and 2 μM Lysotracker Green (1 mM, 0.5 μl) for 1 h at 4° C., RT or 37° C., respectively. Non-specific binding was determined in the presence of 100 μM AMD3100. After incubation, cells were washed twice with ice cold PBS, and fluorescence microscopy images were taken immediately thereafter.

4. In Vivo Evaluation

To determine general tracer pharmacokinetics, in vivo biodistribution studies were alternatively performed in Black Six or CD-1 normal mice. For the most promising compounds, additional biodistribution studies were performed in Daudi (human B-cell lymphoma) xenograft bearing CB-17-SCID mice.

Generally, mice were intravenously (i.v.) injected with the respective radioligands (0.4-3.7 MBq in 100 μL of PBS (pH 7.4)) under isoflurane anesthesia. The animals were sacrificed 60 min postinjection (p.i.) (n=3-5), and the organs of interest were dissected. The radioactivity was measured in weighted tissue samples using a γ-counter. Data are expressed in % ID/g tissue (mean±SD).

To determine CXCR4-specificity of tracer accumulation, a competition study was performed in parallel. The species independent CXCR4 antagonist AMD-3100 (50 μg per mouse, dissolved in 10 μL PBS) was coinjected with the radioligand. The animals (n=3-4) were sacrificed 60 min p.i., and subsequent determination of the activity accumulation in the organs of interest was performed as described above.

EXAMPLE 4

Results

1. Lipophilicities

TABLE 1

Lipophilicities (log $P_{O/PBS}$) of the novel radiolabeled CXCR4 ligands

| Peptide | log $P_{O/PBS}$ |
|---|---|
| [$^{125}$I]R1 | 0.51 |
| [$^{125}$I]P5a | −1.13 |
| [$^{68}$Ga]P5c | −2.64 |
| [$^{111}$In]P5d | −2.82 |
| [$^{68}$Ga]Pc5b | −2.80 |

2. Determination of CXCR4 Affinities

TABLE 2a

Binding affinities (IC$_{50}$ in nM) of novel CXCR4 ligands to human CXCR4 (hCXCR4). Affinities were determined using Jurkat human T-cell leukemia cells (200.000 cells/sample) and [$^{125}$I]FC-131 as the radioligand. Each experiment was performed in triplicate, and results are means ± SD from three separate experiments.

| | compound | IC$_{50}$ [nM] to hCXCR4 |
|---|---|---|
| c(y(NHex-R$^1$)aRNaIG) R$^1$ = Alkylguanidino analogs | | |
| [guanidine structure, NH$_2$] | R | 0.8 ± 0.1 |
| [guanidine-ethyl-NHAc] | P1 | 3.1 ± 1.7 |
| [guanidine-propyl-NHAc] | P2 | 1.7 ± 0.4 |
| [guanidine-butyl-NHAc] | P3 | 2.1 ± 0.5 |
| [guanidine-pentyl-NHAc] | P4 | 32.1 ± 15.5 |
| [guanidine-hexyl-NHAc] | P5 | 9.8 ± 2.3 |

TABLE 2a-continued

Binding affinities (IC$_{50}$ in nM) of novel CXCR4 ligands to human CXCR4 (hCXCR4). Affinities were determined using Jurkat human T-cell leukemia cells (200.000 cells/sample) and [$^{125}$I]FC-131 as the radioligand. Each experiment was performed in triplicate, and results are means ± SD from three separate experiments.

| compound | IC$_{50}$ [nM] to hCXCR4 |
|---|---|
| P6 | 3.2 ± 1.6 |

Acylguanidino analogs

| compound | IC$_{50}$ [nM] to hCXCR4 |
|---|---|
| P7 | 2.5 ± 0.4 |
| P8 | 13.2 ± 3.8 |
| P9 | 78.7 ± 26.2 |
| P10 | 2.0 ± 0.2 |

Functionalized P5 analogs
c(y(NHex-Gua-Hex-R$^2$)aRNaIG)
R$^2$ =

| compound | IC$_{50}$ [nM] to hCXCR4 |
|---|---|
| P5g | 40 ± 5 |
| P5k | 90 ± 29 |
| P5m | 52 ± 20 |
| P5-QD | 7.7 ± 2.7 |

TABLE 2b

Binding affinities (IC$_{50}$ in nM) of novel CXCR4 ligands to human CXCR4 (hCXCR4). Affinities were determined using Jurkat human T-cell leukemia cells (400.000 cells/sample) and [$^{125}$I]FC-131 as the radioligand. Each experiment was performed in triplicate, and results are means ± SD from three separate experiments.

| c(y-(N-hexylguanidino)a-R-Nal-c(R$^3$)) R$^3$ = | compound | IC$_{50}$ [nM] to hCXCR4 |
|---|---|---|
| HS---- | Pc0 | 35 ± 2 |
| (structure with H$_2$N, acetamido-lysine-like with S----) | Pc1 | 61 ± 8 |
| (acetamido-hexyl-amido-S----) | Pc2 | 57 ± 14 |
| (acetamido-hexyl-S----) | Pc3 | >400 |
| (acetamido-methyl-phenyl-methyl-amido-S----, para) | Pc4 | 53 ± 16 |
| (acetamido-methyl-phenyl-methyl-amido-S----, meta) | Pc5 | 14 ± 2 | functionalized Pc5 analogs

| | | |
|---|---|---|
| (DOTA-conjugated Pc5 analog) | Pc5a | 78 ± 4 |

TABLE 2b-continued

Binding affinities (IC$_{50}$ in nM) of novel CXCR4 ligands to human CXCR4 (hCXCR4). Affinities were determined using Jurkat human T-cell leukemia cells (400.000 cells/sample) and [$^{125}$I]FC-131 as the radioligand. Each experiment was performed in triplicate, and results are means ± SD from three separate experiments.

| c(y-(N-hexylguanidino)a-R-Nal-c(R$^3$))  R$^3$ = | compound | IC$_{50}$ [nM] to hCXCR4 |
|---|---|---|
| *(structure with Ga-cyclen tetracarboxylate linked via amide-benzene-amide to S)* | Pc5b | 31 ± 3 |
| *(structure with Lu-cyclen tetracarboxylate linked via amide-benzene-amide to S)* | Pc5c | 51 ± 4 |
| *(structure with Cu-cyclen tetracarboxylate linked via amide-benzene-amide to S)* | Pc5d | 78 ± 5 |
| | Pc5-QD | 6.1 ± 0.3 |

TABLE 3

Binding affinities (IC$_{50}$ in nM) of novel CXCR4 ligands to human, mouse and rat CXCR4 (hCXCR4, mCXCR4 and rCSCR4). Affinities were determined using Jurkat human T-cell-leukemia (hCXCR4), Eµ-Myc1080 mouse B-cell lymphoma and C6 rat glioblastoma cells, respectively (200.000 cells/sample), and [$^{125}$I]R1 as the radioligand. Each experiment was performed in triplicate, and results are means ± SD from three separate experiments.

| | compound | IC$_{50}$ [nM] to hCXCR4 | IC$_{50}$ [nM] to mCXCR4 | IC$_{50}$ [nM] to rCXCR4 |
|---|---|---|---|---|
| Alkylguanidino analogs | | | | |
| c(y(NHex-R$^1$)aRNaIG) R$^1$ = | | | | |
| 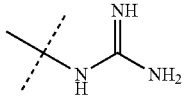 | R | 2.8 ± 1.1 | 0.8 ± 0.1 | 115 ± 24 |
| c(3-iodo-y(NHex-R$^1$)aRNaIG) | | | | |
| 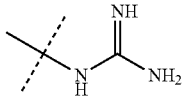 | R1 | 5.4 ± 1.5 | 4.9 ± 1.7 | |
| 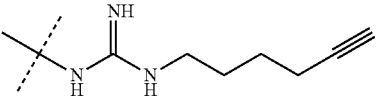 | P6 | | 6.2 ± 2.8 | |
| Acylguanidino analogs | | | | |
| 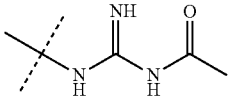 | P7 | | 1.6 (n = 1) | |
| 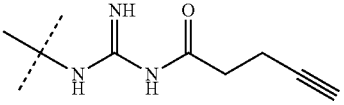 | P10 | | 5.5 ± 2.5 | |
| Functionalized P5 analogs | | | | |
| c(y(NHex-Gua-Hex-R$^2$)aRNaIG) R$^2$ = | | | | |
| 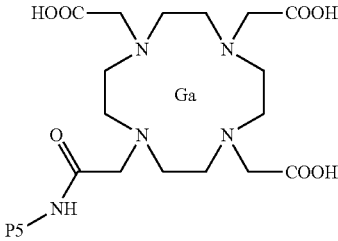 | P5c | 13.0 ± 2.0 | 12.7 ± 4.6 | |
| 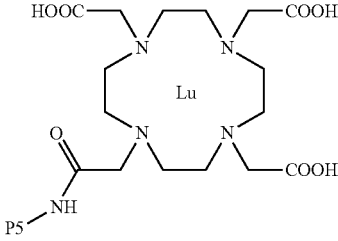 | P5d | 12.9 ± 2.3 | 17.0 ± 3.3 | |

TABLE 3-continued

Binding affinities (IC$_{50}$ in nM) of novel CXCR4 ligands to human, mouse and rat CXCR4 (hCXCR4, mCXCR4 and rCSCR4). Affinities were determined using Jurkat human T-cell-leukemia (hCXCR4), Eμ-Myc1080 mouse B-cell lymphoma and C6 rat glioblastoma cells, respectively (200.000 cells/sample), and [$^{125}$I]R1 as the radioligand. Each experiment was performed in triplicate, and results are means ± SD from three separate experiments.

| compound | IC$_{50}$ [nM] to hCXCR4 | IC$_{50}$ [nM] to mCXCR4 | IC$_{50}$ [nM] to rCXCR4 |
| --- | --- | --- | --- |
| P5e | 156 ± 11 | 156 ± 7 | |

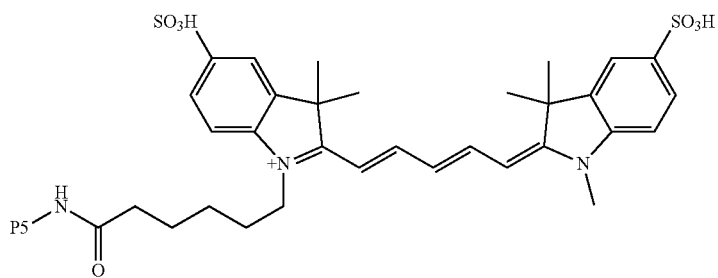

| | | | |
| --- | --- | --- | --- |
| P5f | 115 ± 39 | 136 ± 26 | |

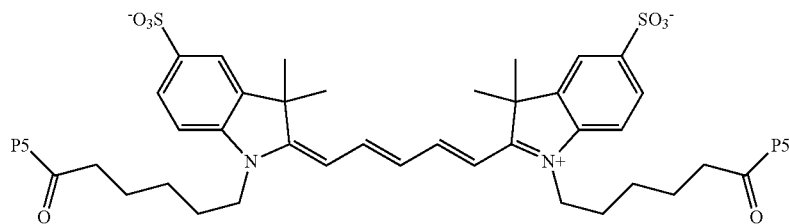

| | | | |
| --- | --- | --- | --- |
| P5g | 91 ± 49 | 63 ± 23 | |

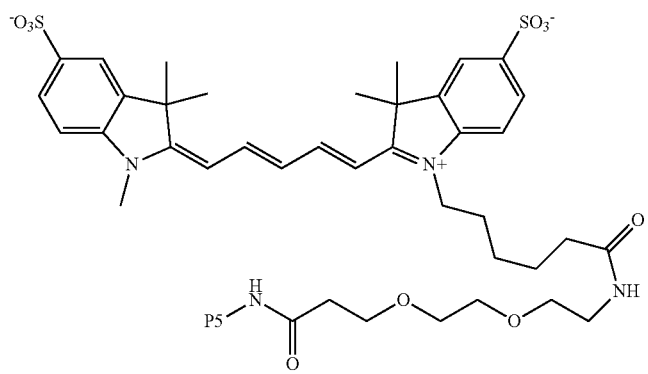

TABLE 3-continued

Binding affinities (IC$_{50}$ in nM) of novel CXCR4 ligands to human, mouse and rat CXCR4 (hCXCR4, mCXCR4 and rCSCR4). Affinities were determined using Jurkat human T-cell-leukemia (hCXCR4), Eμ-Myc1080 mouse B-cell lymphoma and C6 rat glioblastoma cells, respectively (200.000 cells/sample), and [$^{125}$I]R1 as the radioligand. Each experiment was performed in triplicate, and results are means ± SD from three separate experiments.

| compound | IC$_{50}$ [nM] to hCXCR4 | IC$_{50}$ [nM] to mCXCR4 | IC$_{50}$ [nM] to rCXCR4 |
|---|---|---|---|
| 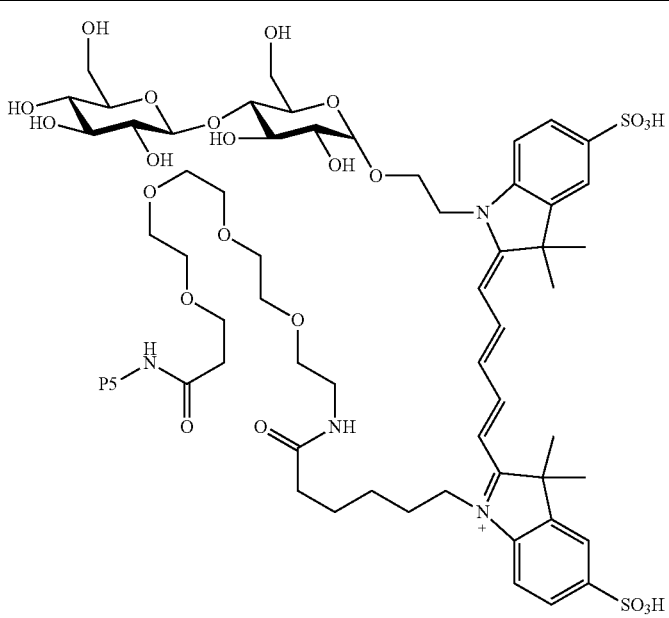 P5h | 129 ± 27 | 156 ± 37 | |
| 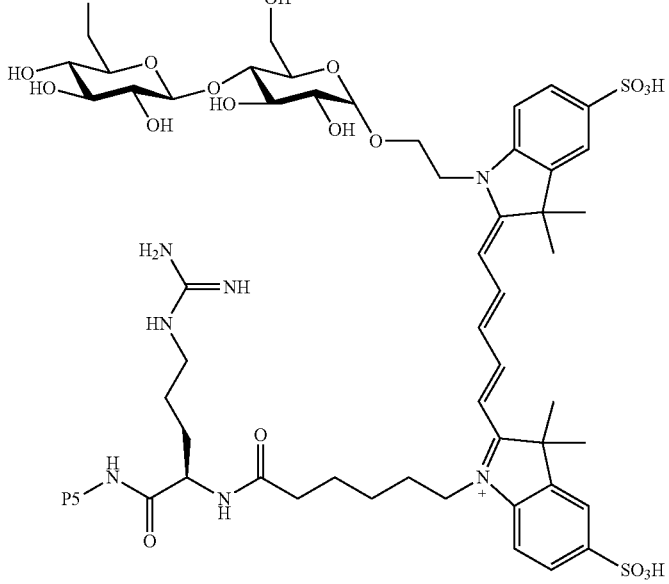 P5i | 147 ± 73 | 92 ± 30 | |
| P5-QD | 4.8 ± 2.2 | 4.9 ± 1.8 | |

TABLE 3-continued

Binding affinities (IC$_{50}$ in nM) of novel CXCR4 ligands to human, mouse and rat CXCR4 (hCXCR4, mCXCR4 and rCSCR4). Affinities were determined using Jurkat human T-cell-leukemia (hCXCR4), Eµ-Myc1080 mouse B-cell lymphoma and C6 rat glioblastoma cells, respectively (200.000 cells/sample), and [$^{125}$I]R1 as the radioligand. Each experiment was performed in triplicate, and results are means ± SD from three separate experiments.

| compound | IC$_{50}$ [nM] to hCXCR4 | IC$_{50}$ [nM] to mCXCR4 | IC$_{50}$ [nM] to rCXCR4 |
|---|---|---|---|
| c(γ-(N-hexylguanidino)a-R-Nal-c(m-aryl-R$^4$)) R$^4$ = | | | |
| Pc5b | 64 ± 29 | | 63 ± 19 |
| Pc5-QD | 8.3 ± 4.3 | | 3.3 ± 0.7 |

3. Fluorescence Microscopy

Figure 2:
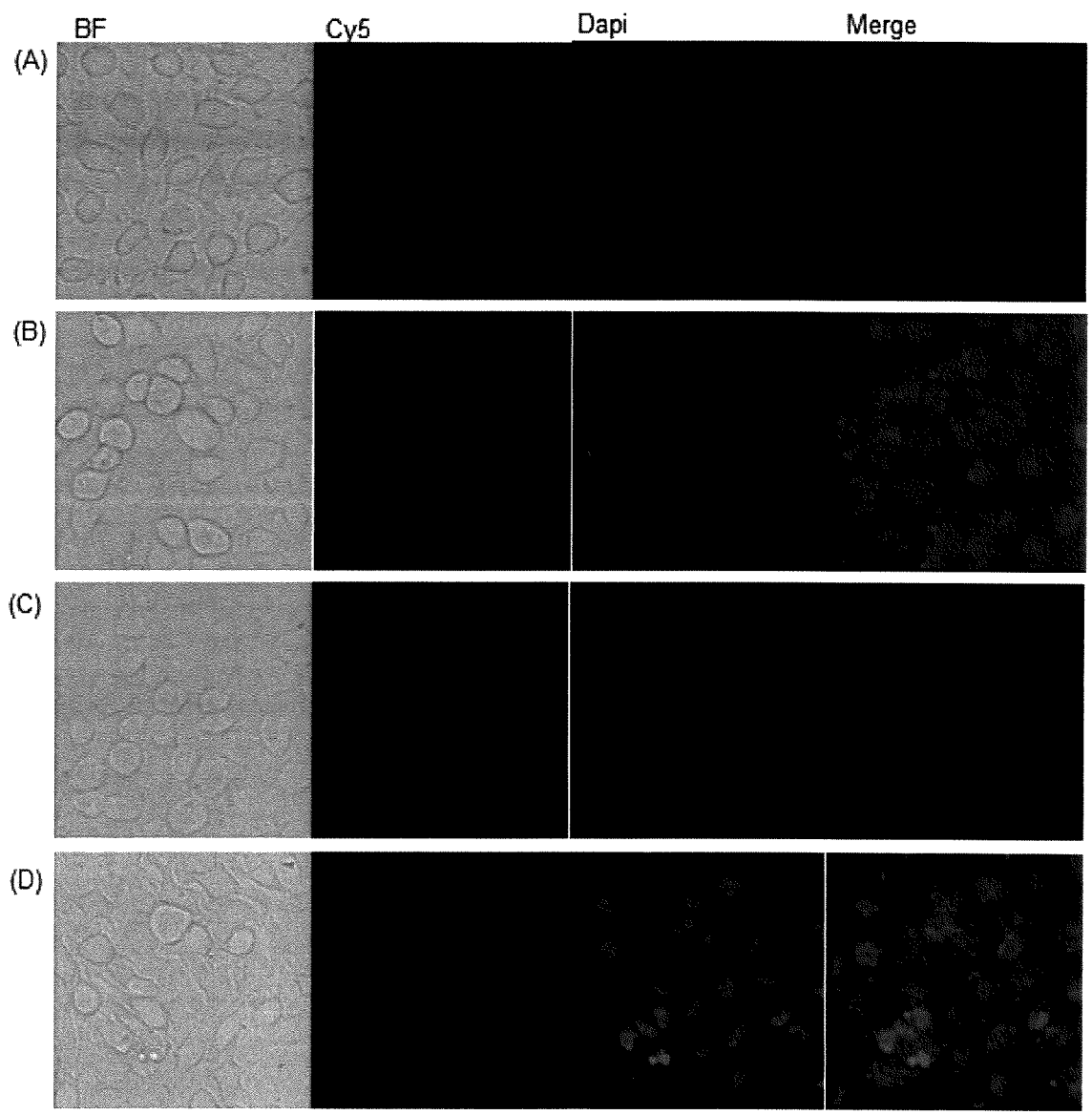
FIG. 2: Fluorescence microscopy of P5h and P5f binding to CXCR4 expressing Chem-1 cells. (A) P5h, 100 nM, 4° C. (B) P5h, 100 nM, 37° C. (C) P5f, 100 nM, 4° C. (D) P5f, 100 nM, 37° C. Cells were also stained with Hoechst [2 µg/ml] (cell nuclei, blue) and Lysotracker Green [2 µM] (lysosomes, green) for visual aid. Cy5 images were taken with an excitation time of 8 s. Original magnification ×20.
Figure 3:
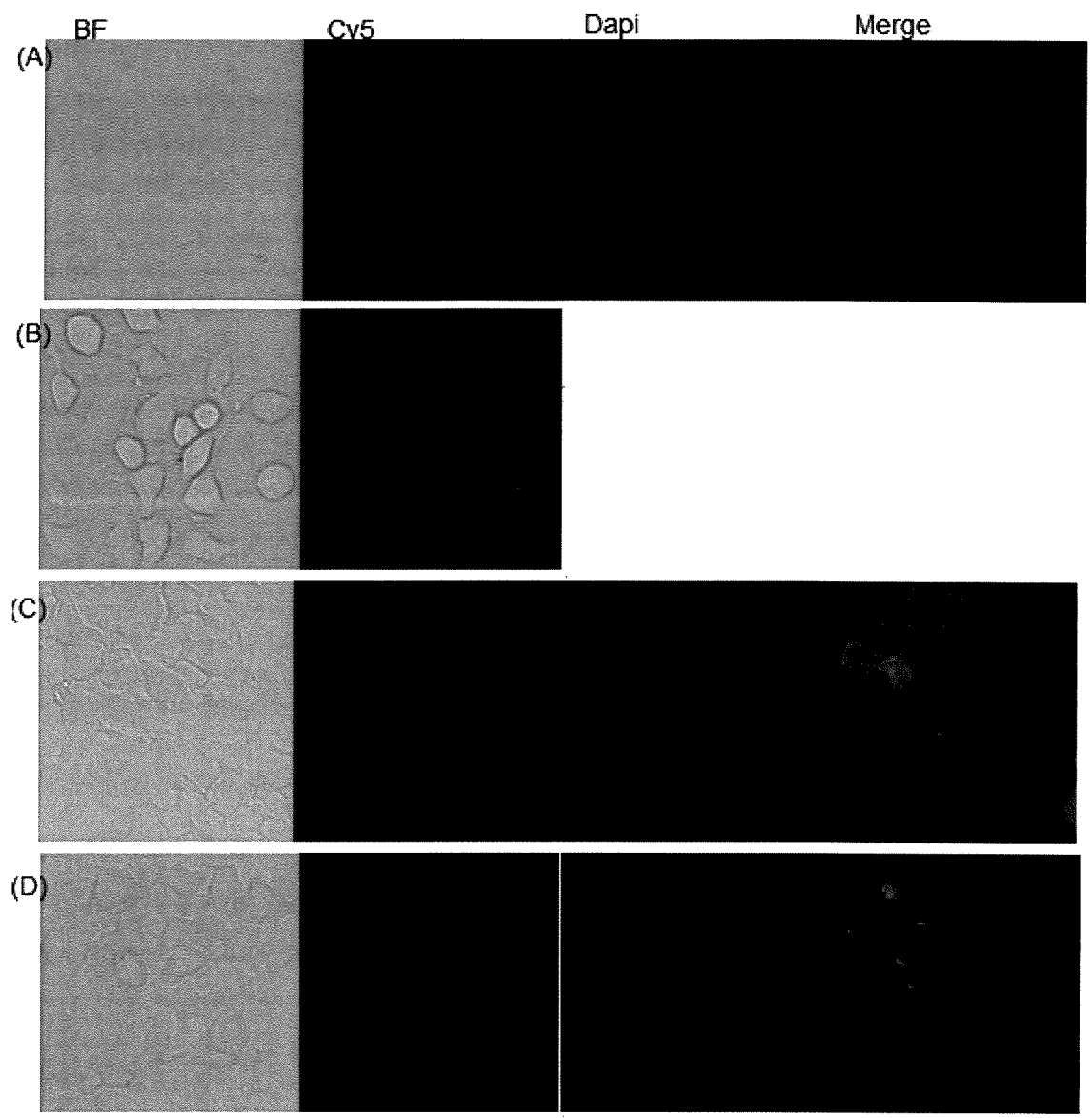
FIG. 3: Fluorescence microscopy of P5g binding to CXCR4 expressing Chem-1 cells. (A) P5g, 500 nM, 4° C. (B) P5g, 500 nM, 4° C. in the presence of 100 µM AMD3100 (C) P5g, 500 nM, 37° C. (D) P5g, 500 nM, 37° C. in the presence of 100 µM AMD3100. Cells were also stained with Hoechst [2 µg/ml] (cell nuclei, blue) and Lysotracker Green [2 µM](lysosomes, green) for visual aid. Cy5 images were taken with an excitation time of 8 s. Original magnification ×20.
Figure 4:
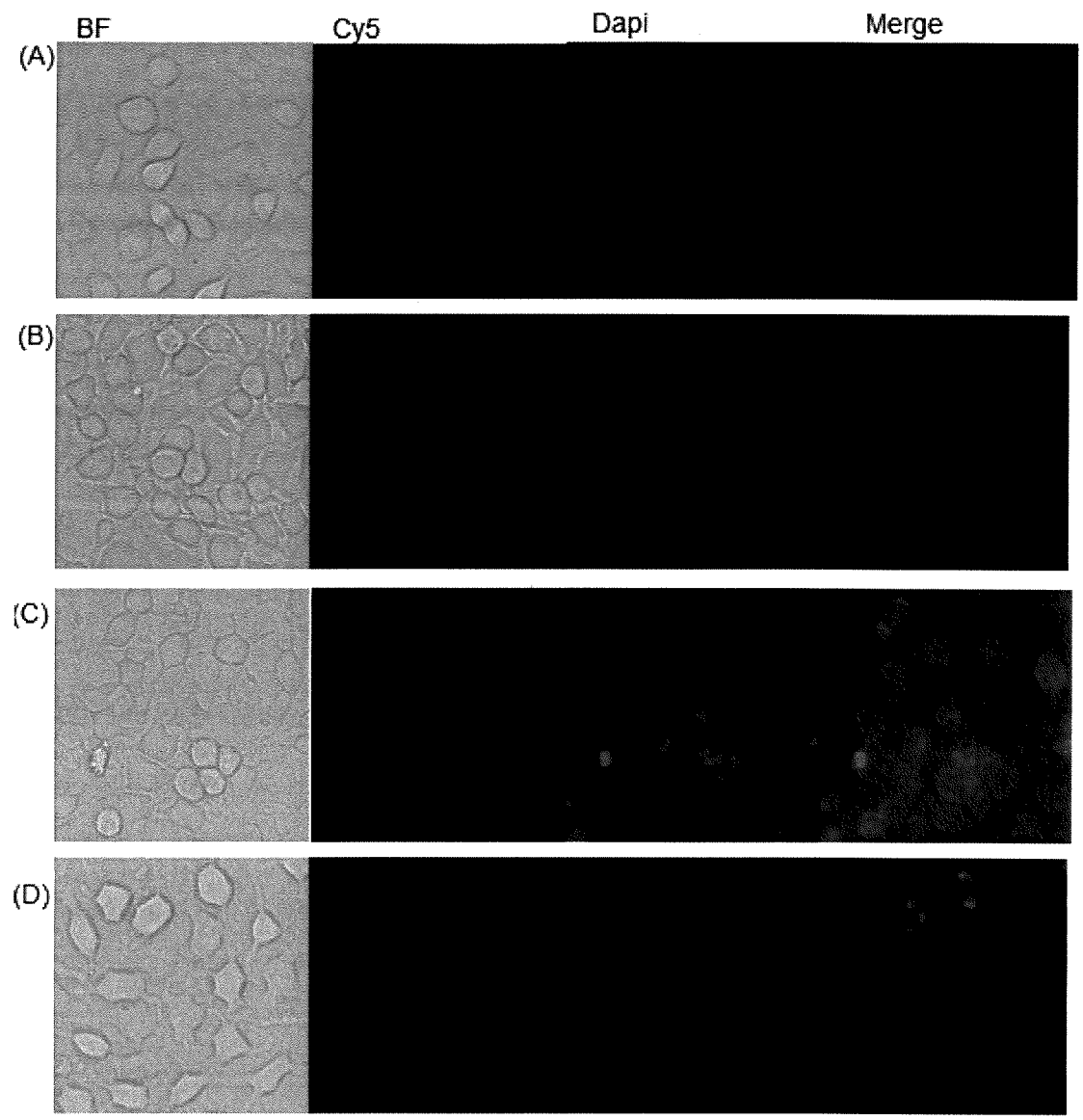
FIG. 4: Fluorescence microscopy of P5h binding to CXCR4 expressing Chem-1 cells. (A) P5h, 500 nM, 4° C. (B) P5h, 500 nM, 4° C. in the presence of 100 µM AMD3100 (C) P5h, 500 nM, 37° C. (D) P5h, 500 nM, 37° C. in the presence of 100 µM AMD3100. Cells were also stained with Hoechst [2 µg/ml] (cell nuclei, blue) and Lysotracker Green [2 µM](lysosomes, green) for visual aid. Cy5 images were taken with an excitation time of 8 s. Original magnification ×20.
Figure 5:
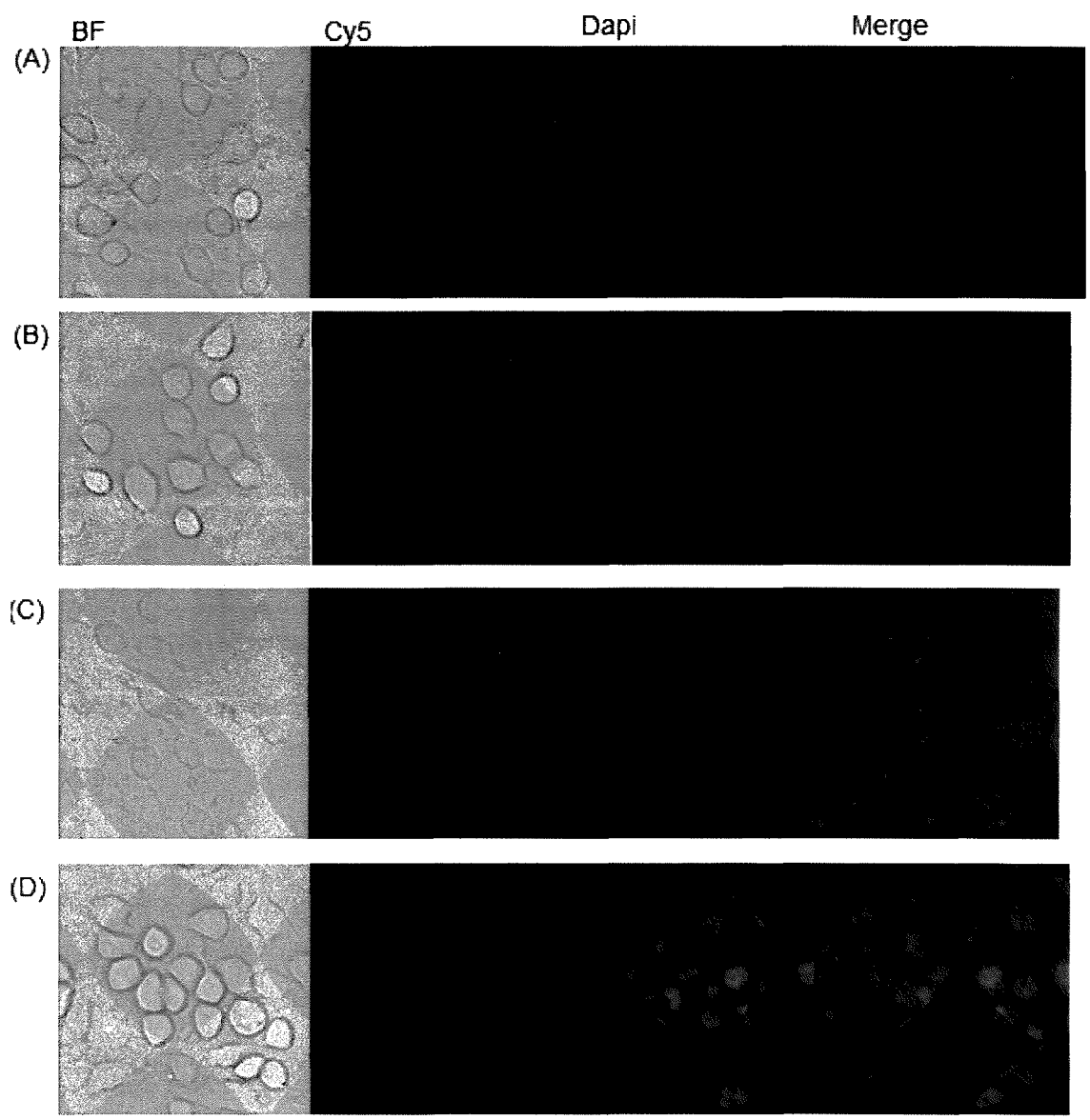
FIG. 5: Fluorescence microscopy of P5i binding to CXCR4 expressing Chem-1 cells. (A) P5i, 500 nM, 4° C. (B) P5i, 500 nM, 4° C. in the presence of 100 µM AMD3100 (C) P5i, 500 nM, 37° C. (D) P5i, 500 nM, 37° C. in the presence of 100 µM AMD3100. Cells were also stained with Hoechst [2 µg/ml] (cell nuclei, blue) and Lysotracker Green [2 µM] (lysosomes, green) for visual aid. Cy5 images were taken with an excitation time of 8 s. Original magnification ×20.
Figure 6:
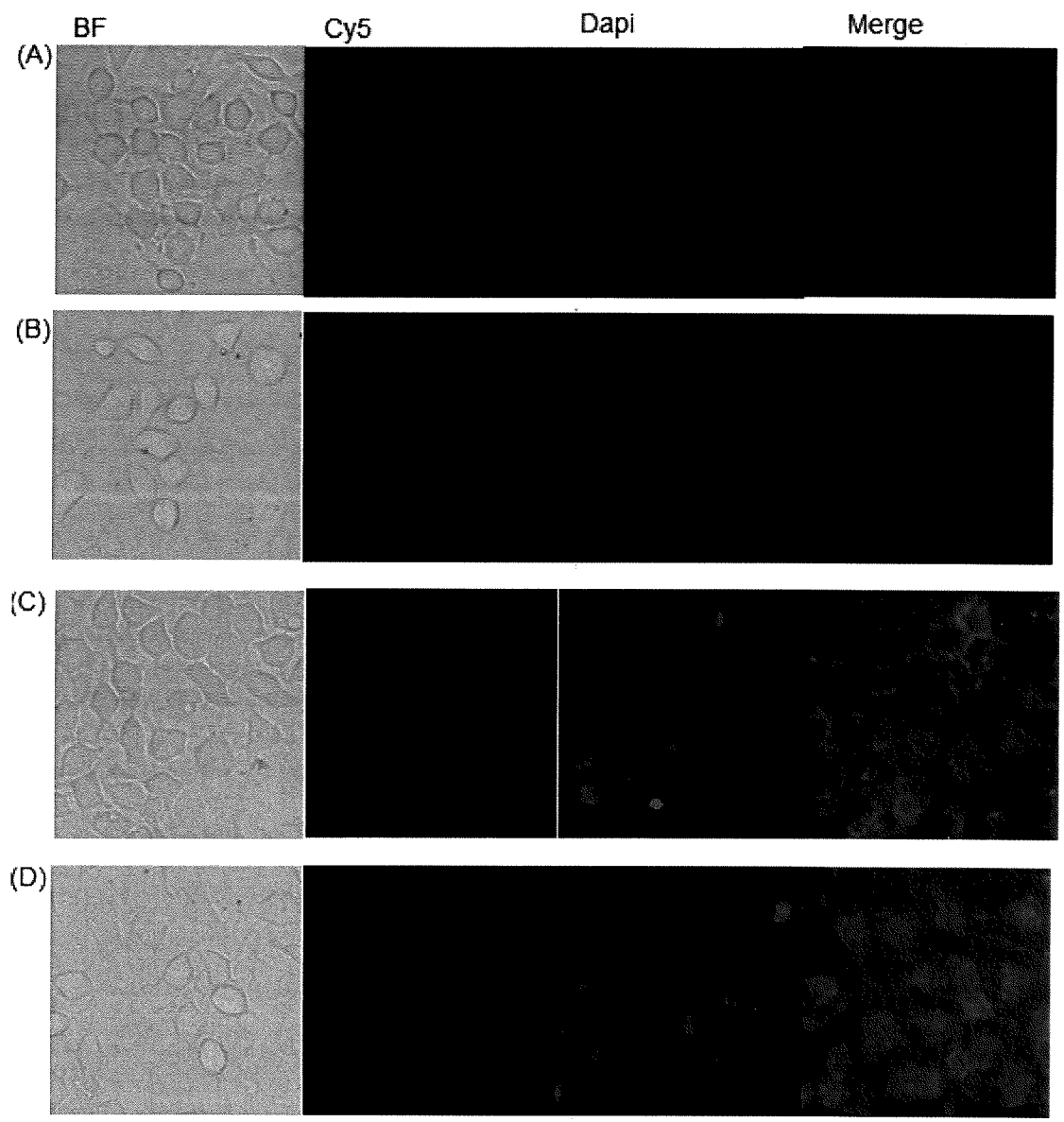
FIG. 6: Fluorescence microscopy of P5f binding to CXCR4 expressing Chem-1 cells. (A) P5f, 500 nM, 4° C. (B) P5f, 500 nM, 4° C. in the presence of 100 µM AMD3100 (C) P5f, 500 nM, 37° C. (D) P5f, 500 nM, 37° C. in the presence of 100 µM AMD3100. Cells were also stained with Hoechst [2 µg/ml] (cell nuclei, blue) and Lysotracker Green [2 µM] (lysosomes, green) for visual aid. Cy5 images were taken with an excitation time of 8 s. Original magnification ×20.
Figure 7:
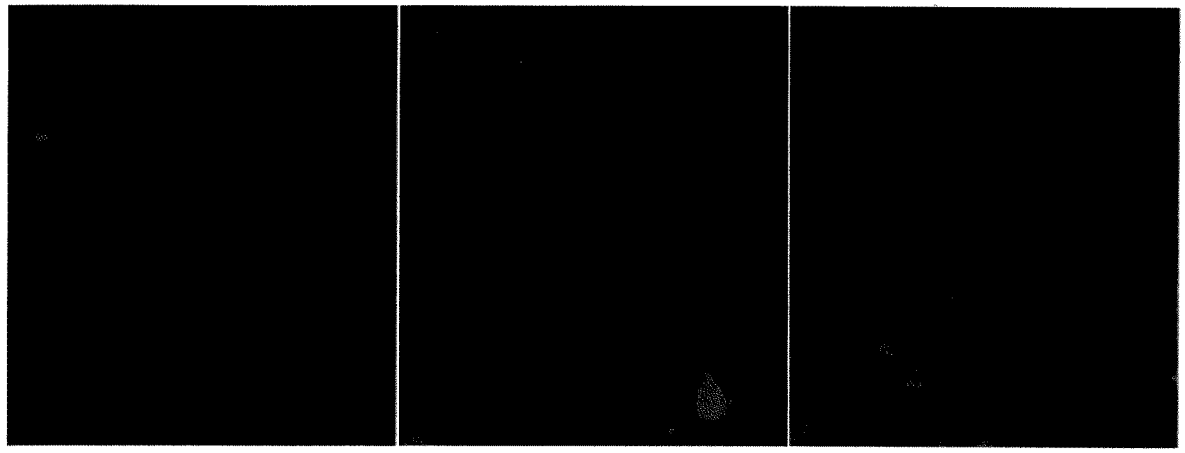
FIG. 7: Fluorescence microscopy of Pc5-QD binding to different CXCR4 expressing cell lines. Left: human Daudi lymphoma cells, 100 nM Pc5-QD, 1 h, RT; Middle: Ep-Myc1080 mouse B-cell lymphoma cells, 25 nM Pc5-QD, 1 h, RT; Right: hCXCR4 expressing Chem-1 cells, 25 nM Pc5-QD, 1 h, RT. Original magnification ×20.
Figure 8:
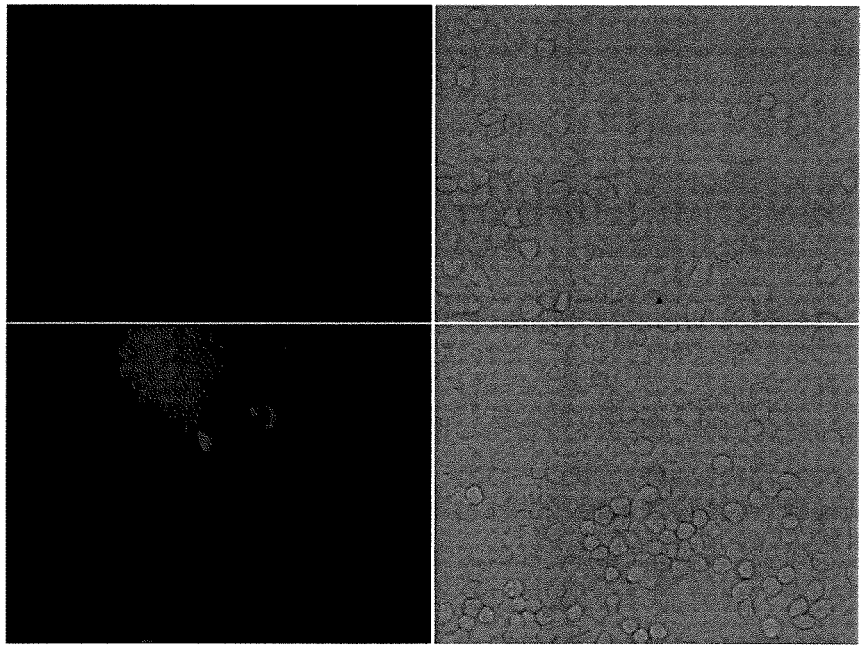
FIG. 8: Specificity of Pc5-QD binding to hCXCR4 expressing Chem-1 cells. Upper panel: uncoated QD's, 25 nM, 1 h, RT (negative control) and corresponding light microscopy image Lower panel: Pc5-QD, 25 nM, 1 h, RT, and corresponding light microscopy image. Original magnification ×20.
Figure 9:
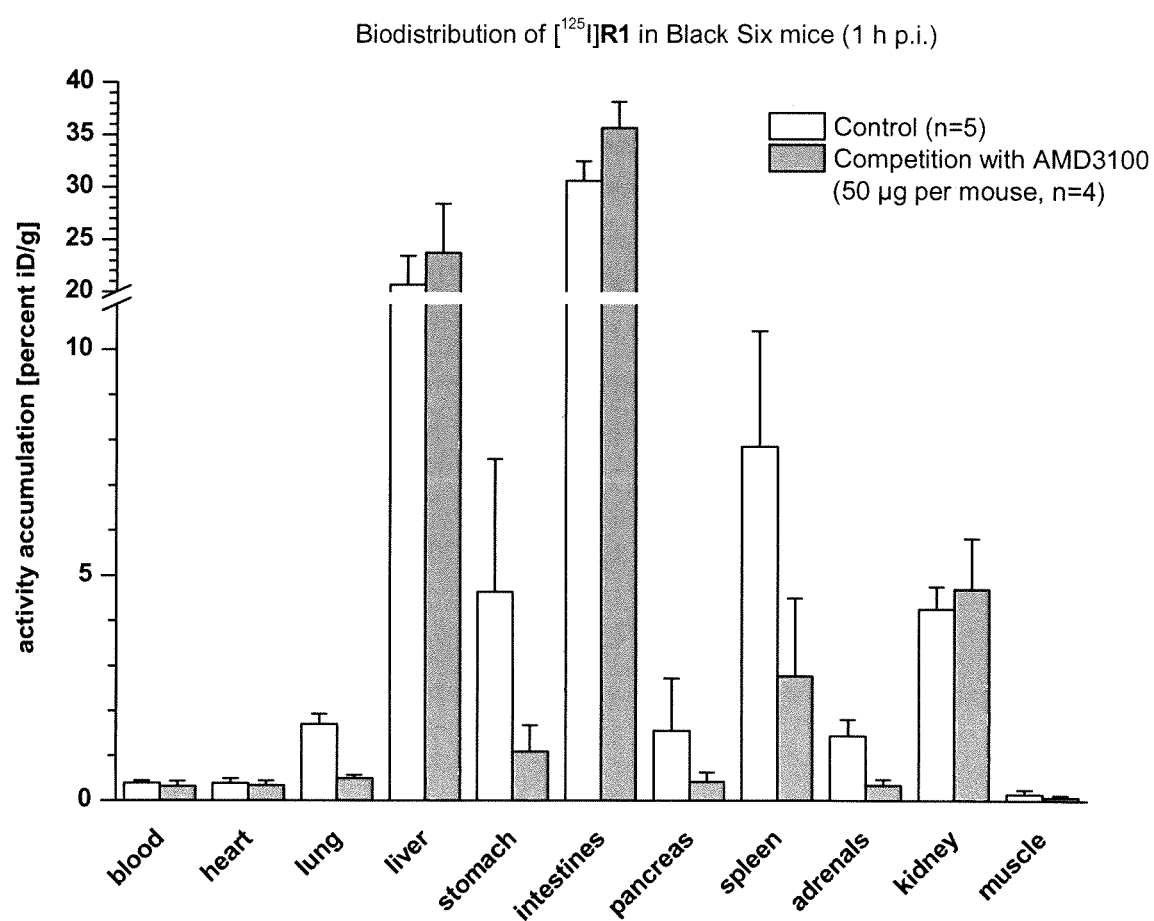
FIG. 9: Biodistribution of [$^{125}$I]R1 in Black Six normal mice at 1 h p.i. White bars: tracer only (n=5), grey bars: coinjection of 50 µg AMD3100 (2 mg/kg, n=4). Data are represented as % iD/g and are means±SD.
Figure 10:
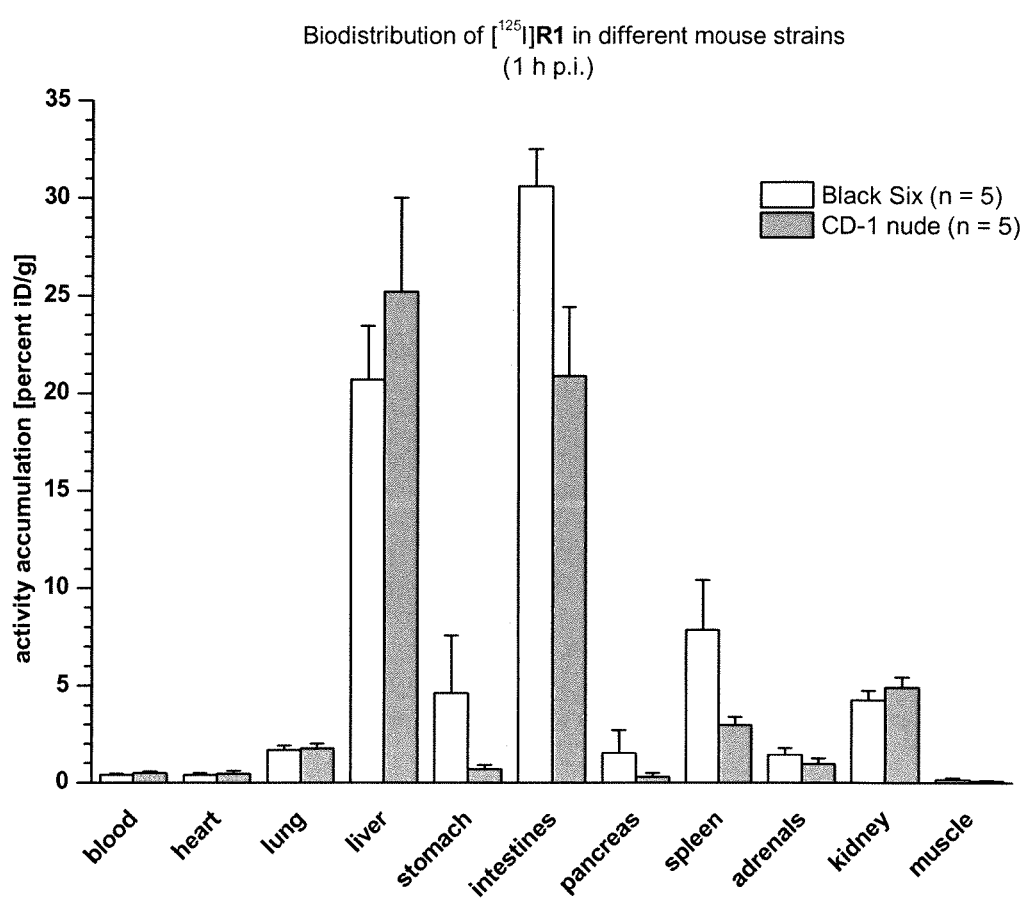
FIG. 10: Biodistribution of [$^{125}$I]R1 in Black Six normal mice and CD-1 nude mice at 1 h p.i. White bars: Black Six mice (n=5), grey bars: CD-1 nude mice. Data are represented as % iD/g and are means±SD.
Figure 11:
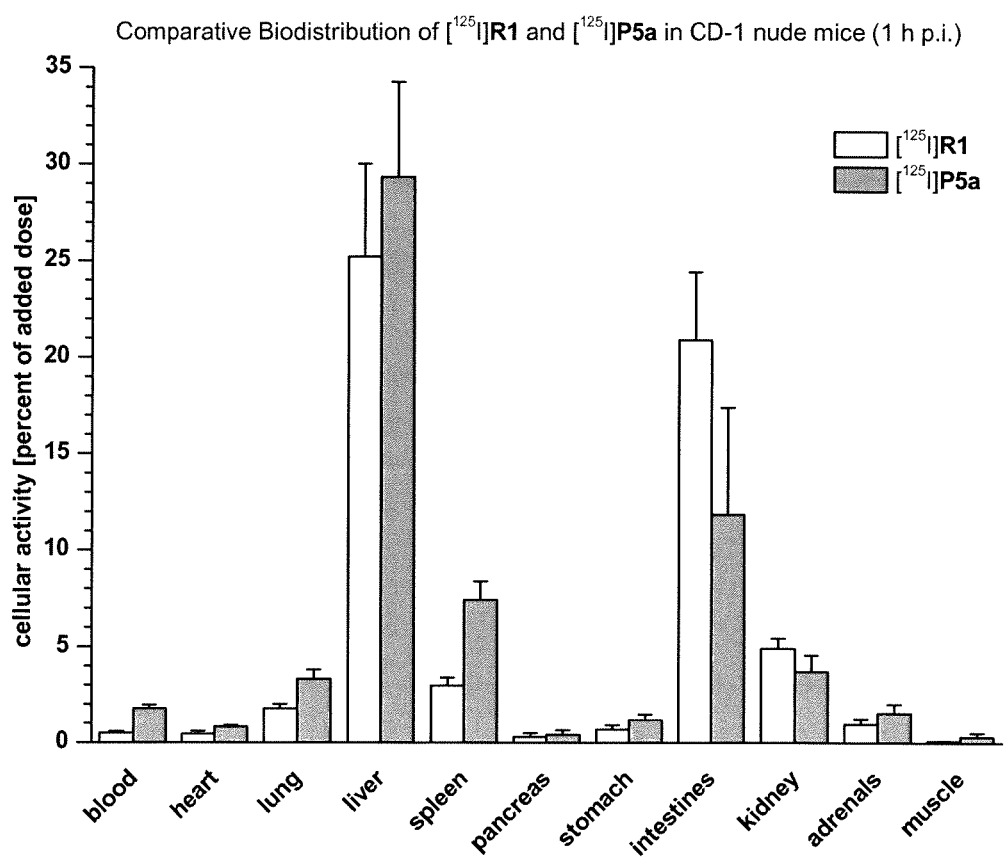
FIG. 11: Biodistribution of [$^{125}$I]R1 and [$^{125}$I]P5a in CD-1 nude mice at 1 h p.i. White bars: [$^{125}$I]R1, tracer only (n=5); grey bars: [$^{125}$I]P5a, tracer only (n=5). Data are represented as % iD/g and are means±SD.
Figure 12:
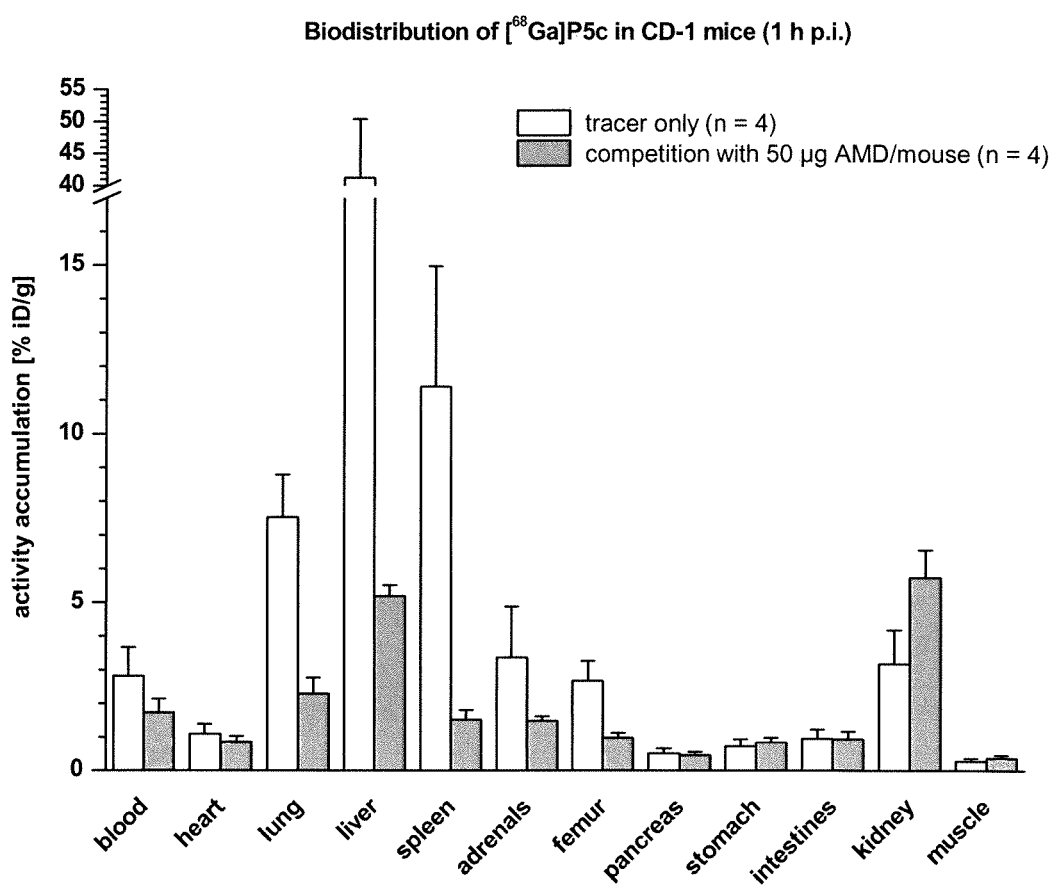
FIG. 12: Biodistribution of [$^{68}$Ga]P5c in CD-1 nude mice at 1 h p.i. White bars: tracer only 25 (n=4), grey bars: coinjection of 50 µg AMD3100 (2 mg/kg, n=4). Data are represented as % iD/g and are means±SD.
Figure 13:
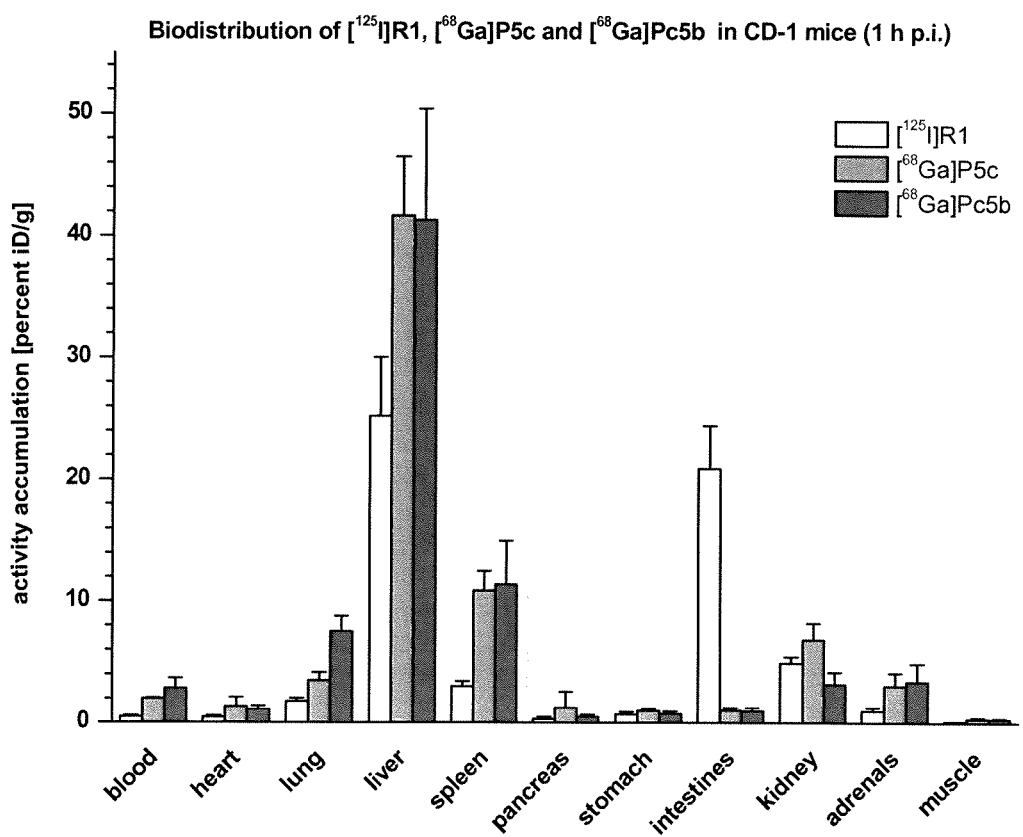
FIG. 13: Biodistribution of [$^{125}$I]R1, [$^{68}$Ga]P5c and [$^{68}$Ga]Pc5b in CD-1 nude mice at 1 h p.i. White bars: [$^{125}$I]R1 (n=5), grey bars: [$^{68}$Ga]P5c (n=4), dark grey bars: [$^{68}$Ga]Pc5b (n=4). Data are represented as % iD/g and are means±SD.
Figure 14:
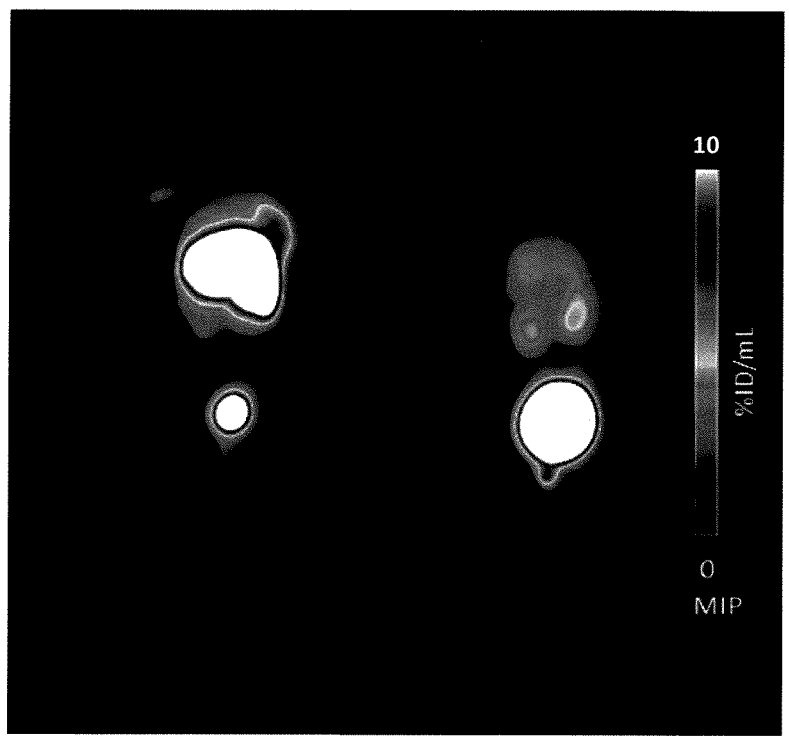
FIG. 14: Small animal [$^{68}$Ga]P5c-PET (MIP) of Daudi lymphoma bearing CB-17 SCID mice at 1 h p.i. Animals received app. 12 MBq of [$^{68}$Ga]P5c. Left panel: tracer only (red arrow indicates the lymphoma xenograft); right panel: coinjection of 50 µg AMD3100.
Figure 15:
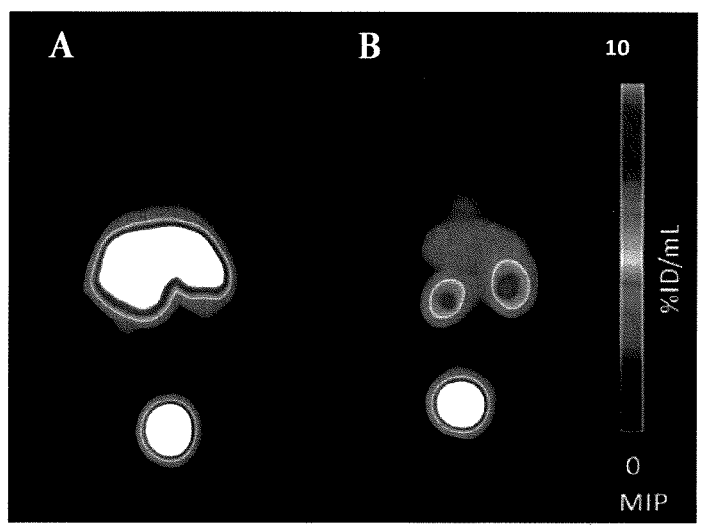
FIG. 15: Small animal [$^{68}$Ga]Pc5b-PET (MIP) of healthy CB-17 SCID mice at 1 h p.i. Animals received app. 13 MBq of [$^{68}$Ga]Pc5b. A: tracer only, B: coinjection of 50 µg AMD3100.

Chem-1 cells stably transfected with hCXCR4 were incubated with the respective Sulfo-Cy5 conjugated peptides for 1 h at 4° C. or at 37° C. The ligand concentrations used in the respective experiments are cited in the Figure captions. Non-specific ligand binding was determined in the presence of AMD3100 (100 µM). Cell nuclei were stained with Hoechst (2 µg/ml), and ligand internalization into endosomes and lysosomes was confirmed by co-staining using lysotracker green (2 µM). See FIGS. 2 to 8.

FURTHER REFERENCES

1. Zlotnik A. Yoshie O. Chemokines: a new classification system and their role in immunity. Immunity 2000; 12:121-127.
2. Domanska U M, Kruizinga R C, Nagengast W B, Timmer-Bosscha H, Huls G, de Vries E G, et al. A review on CXCR4/CXCL12 axis in oncology: no place to hide. European journal of cancer 2013; 49:219-230.
3. Feng Y, Broder C C, Kennedy P E, Berger E A. HIV-1 entry cofactor: functional cDNA cloning of a seven-transmembrane, G protein-coupled receptor. Science 1996; 272:872-877.
4. Nagasawa T, Hirota S, Tachibana K, Takakura N, Nishikawa S-i, Kitamura Y, et al. Defects of B-cell lymphopoiesis and bone-marrow myelopoiesis in mice lacking the CXC chemokine PBSF/SDF-1. Nature 1996; 382:635-638.
5. Loetscher P, Moser B, Baggiolini M. Chemokines and their receptors in lymphocyte traffic and HIV infection. Advances in immunology 2000; 74:127-180.
6. Aiuti A, Webb I, Bleul C, Springer T, Gutierrez-Ramos J. The chemokine SDF-1 is a chemoattractant for human CD34+ hematopoietic progenitor cells and provides a new mechanism to explain the mobilization of CD34+ progenitors to peripheral blood. The Journal of experimental medicine 1997; 185:111-120.
7. Ma Q, Jones D, Borghesani P R, Segal R A, Nagasawa T, Kishimoto T, et al. Impaired B-lymphopoiesis, myelopoiesis, and derailed cerebellar neuron migration in CXCR4- and SDF-1-deficient mice. Proc Natl Acad Sci 0 S A 1998; 95:9448-9453.
8. Nagafuchi Y, Shoda H, Sumitomo S, Nakachi S, Kato R, Tsuchida Y, et al. Immunophenotyping of rheumatoid arthritis reveals a linkage between HLA-DRB1 genotype, CXCR4 expression on memory CD4(+) T cells, and disease activity. Sci Rep 2016; 6:29338.
9. Galkina E, Ley K. Immune and inflammatory mechanisms of atherosclerosis (*). Annu Rev Immunol 2009; 27:165-197.
10. Schober A, Bernhagen J, Weber C. Chemokine-like functions of MIF in atherosclerosis. J Mol Med (Berl) 2008; 86:761-770.
11. Burger J A, Burger M, Kipps T J. Chronic lymphocytic leukemia B cells express functional CXCR4 chemokine receptors that mediate spontaneous migration beneath bone marrow stromal cells. Blood 1999; 94:3658-3667.
12. Müller A, Homey B, Soto H, Ge N, Catron D, Buchanan M E, et al. Involvement of chemokine receptors in breast cancer metastasis, nature 2001; 410:50-56.
13. Burger J A, Kipps T J. CXCR4: a key receptor in the crosstalk between tumor cells and their microenvironment. Blood 2006; 107:1761-1767.
14. Chatterjee S, Azad B B, Nimmagadda S. The intricate role of CXCR4 in cancer. Advances in cancer research 2014; 124:31.
15. Brave M, Farrell A, Ching Lin S, Ocheltree T, Pope Miksinski S, Lee S L, et al. FDA review summary: Mozobil in combination with granulocyte colony-stimulating factor to mobilize hematopoietic stem cells to the peripheral blood for collection and subsequent autologous transplantation. Oncology 2010; 78:282-288.

16. Liu T, Li X, You S, Bhuyan S S, Dong L. Effectiveness of AMD3100 in treatment of leukemia and solid tumors: from original discovery to use in current clinical practice. Exp Hematol Oncol 2015; 5:19.
17. Taromi S, Kayser G, Catusse J, von Elverfeldt D, Reichardt W, Braun F, et al. CXCR4 antagonists suppress small cell lung cancer progression. Oncotarget 2016; 7:85185-85195.
18. Bodart V, Anastassov V, Darkes M C, Idzan S R, Labrecque J, Lau G, et al. Pharmacology of AMD3465: a small molecule antagonist of the chemokine receptor CXCR4. Biochem Pharmacol 2009; 78:993-1000.
19. Ling X, Spaeth E, Chen Y, Shi Y, Zhang W, Schober W, et al. The CXCR4 antagonist AMD3465 regulates oncogenic signaling and invasiveness in vitro and prevents breast cancer growth and metastasis in vivo. PLoS One 2013; 8:e58426.
20. Liang Z, Zhan W, Zhu A, Yoon Y, Lin S, Sasaki M, et al. Development of a unique small molecule modulator of CXCR4. PLoS One 2012; 7:e34038.
21. Wong D, Kandagatla P, Korz W, Chinni S R. Targeting CXCR4 with CTCE-9908 inhibits prostate tumor metastasis. BMC Urol 2014; 14:12.
22. Beider K, Darash-Yahana M, Blaier O, Koren-Michowitz M, Abraham M, Wald H, et al. Combination of imatinib with CXCR4 antagonist BKT140 overcomes the protective effect of stroma and targets CML in vitro and in vivo. Mol Cancer Ther 2014; 13:1155-1169.
23. Fahham D, Weiss I D, Abraham M, Beider K, Hanna W, Shlomai Z, et al. In vitro and in vivo therapeutic efficacy of CXCR4 antagonist BKT140 against human non-small cell lung cancer. J Thorac Cardiovasc Surg 2012; 144: 1167-1175 e1161.
24. Peled A, Abraham M, Avivi I, Rowe J M, Beider K, Wald H, et al. The high-affinity CXCR4 antagonist BKT140 is safe and induces a robust mobilization of human CD34+ cells in patients with multiple myeloma. Clin Cancer Res 2014; 20:469-479.
25. Karpova D, Dauber K, Spohn G, Chudziak D, Wiercinska E, Schulz M, et al. The novel CXCR4 antagonist POL5551 mobilizes hematopoietic stem and progenitor cells with greater efficiency than Plerixafor. Leukemia 2013; 27:2322-2331.
26. Sison E A, Magoon D, Li L, Annesley C E, Romagnoli B, Douglas G J, et al. POL5551, a novel and potent CXCR4 antagonist, enhances sensitivity to chemotherapy in pediatric ALL. Oncotarget 2015; 6:30902-30918.
27. Xiang J, Hurchla M A, Fontana F, Su X, Amend S R, Esser A K, et al. CXCR4 Protein Epitope Mimetic Antagonist POL5551 Disrupts Metastasis and Enhances Chemotherapy Effect in Triple-Negative Breast Cancer. Mol Cancer Ther 2015; 14:2473-2485.
28. Azad B B, Chatterjee S, Lesniak W G, Lisok A, Pullambhatla M, Bhujwalla Z M, et al. A fully human CXCR4 antibody demonstrates diagnostic utility and therapeutic efficacy in solid tumor xenografts. Oncotarget 2016; 7:12344-12358.
29. Peng S-B, Zhang X, Paul D, Kays L M, Ye M, Vaillancourt P, et al. Inhibition of CXCR4 by LY2624587, a Fully Humanized Anti-CXCR4 Antibody Induces Apoptosis of Hematologic Malignancies. PloS one 2016; 11:e0150585.
30. Ramsey D M, McAlpine S R. Halting metastasis through CXCR4 inhibition. Bioorg Med Chem Lett 2013; 23:20-25.
31. Cho B S, Zeng Z, Mu H, Wang Z, Konoplev S, McGueen T, et al. Antileukemia activity of the novel peptidic CXCR4 antagonist LY2510924 as monotherapy and in combination with chemotherapy. Blood 2015; 126:222-232.
32. Peng S B, Zhang X, Paul D, Kays L M, Gough W, Stewart J, et al. Identification of LY2510924, a novel cyclic peptide CXCR4 antagonist that exhibits antitumor activities in solid tumor and breast cancer metastatic models. Mol Cancer Ther 2015; 14:480-490.
33. Di Maro S, Di Leva F S, Trotta A M, Brancaccio D, Portella L, Aurilio M, et al. Structure-Activity Relationships and Biological Characterization of a Novel, Potent, and Serum Stable C—X—C Chemokine Receptor Type 4 (CXCR4) Antagonist. J Med Chem 2017; 60:9641-9652.
34. Di Maro S, Trotta A M, Brancaccio D, Di Leva F S, La Pietra V, Ierano C, et al. Exploring the N-Terminal Region of C—X—C Motif Chemokine 12 (CXCL12): Identification of Plasma-Stable Cyclic Peptides As Novel, Potent C—X—C Chemokine Receptor Type 4 (CXCR4) Antagonists. J Med Chem 2016; 59:8369-8380.
35. Ierano C, Portella L, Lusa S, Salzano G, D'Alterio C, Napolitano M, et al. CXCR4-antagonist Peptide R-liposomes for combined therapy against lung metastasis. Nanoscale 2016; 8:7562-7571.
36. Fontanella R, Pelagalli A, Nardelli A, D'Alterio C, Ierano C, Cerchia L, et al. A novel antagonist of CXCR4 prevents bone marrow-derived mesenchymal stem cell-mediated osteosarcoma and hepatocellular carcinoma cell migration and invasion. Cancer Lett 2016; 370:100-107.
37. Santagata S, Napolitano M, D'Alterio C, Desicato S, Maro S D, Marinelli L, et al. Targeting CXCR4 reverts the suppressive activity of T-regulatory cells in renal cancer. Oncotarget 2017; 8:77110-77120.
38. George G P, Stevens E, Åberg O, Nguyen Q-D, Pisaneschi F, Spivey A C, et al. Preclinical evaluation of a CXCR4-specific $^{68}$Ga-labelled TN14003 derivative for cancer PET imaging. Bioorganic & medicinal chemistry 2014; 22:796-803.
39. Yan X, Niu G, Wang Z, Yang X, Kiesewetter D O, Jacobson O, et al. Al [$^{18}$F] NOTA-T140 Peptide for Noninvasive Visualization of CXCR4 Expression. Molecular Imaging and Biology 2015:1-8.
40. Jacobson O, Weiss I D, Kiesewetter D O, Farber J M, Chen X. PET of tumor CXCR4 expression with 4-$^{18}$F-T140. Journal of Nuclear Medicine 2010; 51:1796-1804.
41. Wang Z, Zhang M, Wang L, Wang S, Kang F, Li G, et al. Prospective Study of $^{68}$Ga-NOTA-NFB: Radiation Dosimetry in Healthy Volunteers and First Application in Glioma Patients. Theranostics 2015; 5:882-889.
42. Buckle T, van Berg N S, Kuil J, Bunschoten A, Oldenburg J, Borowsky A D, et al. Non-invasive longitudinal imaging of tumor progression using an (111)indium labeled CXCR4 peptide antagonist. Am J Nucl Med Mol Imaging 2012; 2:99-109.
43. Kuil J, Buckle T, Oldenburg J, Yuan H, Borowsky A D, Josephson L, et al. Hybrid peptide dendrimers for imaging of chemokine receptor 4 (CXCR4) expression. Mol Pharm 2011; 8:2444-2453.
44. Kuil J, Buckle T, Yuan H, van den Berg N S, Oishi S, Fujii N, et al. Synthesis and evaluation of a bimodal CXCR4 antagonistic peptide. Bioconjug Chem 2011; 22:859-864.
45. Nishizawa K, Nishiyama H, Oishi S, Tanahara N, Kotani H, Mikami Y, et al. Fluorescent imaging of high-grade bladder cancer using a specific antagonist for chemokine receptor CXCR4. Int J Cancer 2010; 127:1180-1187.
46. Portella L, Vitale R, De Luca S, D'Alterio C, Ierano C, Napolitano M, et al. Preclinical development of a novel 47. Fujii N, Oishi S, Hiramatsu K, Araki T, Ueda S, Tamamura H, et al. Molecular-size reduction of a potent CXCR4-chemokine antagonist using orthogonal combination of conformation- and sequence-based libraries. Angew Chem Int Ed Engl 2003; 42:3251-3253.
48. Tamamura H, Araki T, Ueda S, Wang Z, Oishi S, Esaka A, et al. Identification of novel low molecular weight CXCR4 antagonists by structural tuning of cyclic tetrapeptide scaffolds. Journal of medicinal chemistry 2005; 48:3280-3289.
49. Tamamura H, Esaka A, Ogawa T, Araki T, Ueda S, Wang Z, et al. Structure-activity relationship studies on CXCR4 antagonists having cyclic pentapeptide scaffolds. Org. Biomol. Chem. 2005; 3:4392-4394.
50. Tanaka T, Nomura W, Narumi T, Esaka A, Oishi S, Ohashi N, et al. Structure-activity relationship study on artificial CXCR4 ligands possessing the cyclic pentapeptide scaffold: the exploration of amino acid residues of pentapeptides by substitutions of several aromatic amino acids. Organic & biomolecular chemistry 2009; 7:3805-3809.
51. Inokuchi E, Oishi S, Kubo T, Ohno H, Shimura K, Matsuoka M, et al. Potent CXCR4 antagonists containing amidine type Peptide bond isosteres. ACS Med Chem Lett 2011; 2:477-480.
52. Kobayashi K, Oishi S, Hayashi R, Tomita K, Kubo T, Tanahara N, et al. Structure-activity relationship study of a CXC chemokine receptor type 4 antagonist, FC131, using a series of alkene dipeptide isosteres. J Med Chem 2012; 55:2746-2757.
53. Narumi T, Hayashi R, Tomita K, Kobayashi K, Tanahara N, Ohno H, et al. Synthesis and biological evaluation of selective CXCR4 antagonists containing alkene dipeptide isosteres. Organic & biomolecular chemistry 2010; 8:616-621.
54. Demmer O, Dijkgraaf I, Schottelius M, Wester H-J, Kessler H. Introduction of functional groups into peptides via N-alkylation. Organic letters 2008; 10:2015-2018.
55. Demmer O, Dijkgraaf I, Schumacher U, Marinelli L, Cosconati S, Gourni E, et al. Design, synthesis, and functionalization of dimeric peptides targeting chemokine receptor CXCR4. Journal of medicinal chemistry 2011; 54:7648-7662.
56. Demmer O, Gourni E, Schumacher U, Kessler H, Wester H J. PET imaging of CXCR4 receptors in cancer by a new optimized ligand. ChemMedChem 2011; 6:1789-1791.
57. Gourni E, Demmer O, Schottelius M, D'Alessandria C, Schulz S, Dijkgraaf I, et al. PET of CXCR4 expression by a 68Ga-labeled highly specific targeted contrast agent. J. Nucl. Med. 2011; 52:1803-1810.
58. Wester H J, Keller U, Schottelius M, Beer A, Philipp-Abbrederis K, Hoffmann F, et al. Disclosing the CXCR4 expression in iymphoproliferative diseases by targeted molecular imaging. Theranostics 2015; 5:618.
59. Philipp-Abbrederis K, Herrmann K, Knop S, Schottelius M, Eiber M, Luckerath K, et al. In vivo molecular imaging of chemokine receptor CXCR4 expression in patients with advanced multiple myeloma. EMBO Mol Med 2015; 7:477-487.
60. Lapa C, Schreder M, Schirbel A, Samnick S, Kortum K M, Herrmann K, et al. [$^{68}$Ga]Pentixafor-PET/CT for imaging of chemokine receptor CXCR4 expression in multiple myeloma—Comparison to [(18)F]FDG and laboratory values. Theranostics 2017; 7:205-212.
61. Avanesov M, Karul M. Deriin T. [$^{68}$Ga-pentixafor PET: clinical molecular imaging of chemokine receptor CXCR4 expression in multiple myeloma]. Radiologe 2015; 55:829-831.
62. Herhaus P, Habringer S, Philipp-Abbrederis K, Vag T, Gerngross C, Schottelius M, et al. Targeted positron emission tomography imaging of CXCR4 expression in patients with acute myeloid leukemia. Haematologica 2016; 101:932-940.
63. Lapa C, Luckerath K, Rudelius M, Schmid J S, Schoene A, Schirbel A, et al. [$^{68}$Ga]Pentixafor-PET/CT for imaging of chemokine receptor 4 expression in small cell lung cancer-initial experience. Oncotarget 2016; 7:9288-9295.
64. Lapa C, Luckerath K, Kleinlein I, Monoranu C M, Linsenmann T, Kessler A F, et al. $^{68}$Ga-Pentixafor-PET/CT for Imaging of Chemokine Receptor 4 Expression in Glioblastoma. Theranostics 2016; 6:428-434.
65. Vag T, Gerngross C, Herhaus P, Eiber M, Philipp-Abbrederis K, Graner F P, et al. First Experience with Chemokine Receptor CXCR4-Targeted PET Imaging of Patients with Solid Cancers. J Nucl Med 2016; 57:741-746.
66. Lapa C, Reiter T, Werner R A, Ertl G, Wester H J, Buck A K, et al. [$^{68}$Ga]Pentixafor-PET/CT for Imaging of Chemokine Receptor 4 Expression After Myocardial Infarction. JACC Cardiovasc Imaging 2015; 8:1466-1468.
67. Rischpler C, Nekolla S G, Kossmann H, Dirschinger R J, Schottelius M, Hyafil F, et al. Upregulated myocardial CXCR4-expression after myocardial infarction assessed by simultaneous GA-68 pentixafor PET/MRI. J Nucl Cardiol 2016; 23:131-133.
68. Thackeray J T, Derlin T, Haghikia A, Napp L C, Wang Y, Ross T L, et al. Molecular Imaging of the Chemokine Receptor CXCR4 After Acute Myocardial Infarction. JACC Cardiovasc Imaging 2015; 8:1417-1426.
69. Schmid J S, Schirbel A, Buck A K, Kropf S, Wester H J, Lapa C. [$^{68}$Ga]Pentixafor-Positron Emission Tomography/Computed Tomography Detects Chemokine Receptor CXCR4 Expression After Ischemic Stroke. Circ Cardiovasc Imaging 2016; 9:e005217.
70. Hyafil F, Pelisek J, Laitinen I, Schottelius M, Mohring M, Doring Y, et al. Imaging the Cytokine Receptor CXCR4 in Atherosclerotic Plaques with the Radiotracer $^{68}$Ga-Pentixafor for PET. J Nucl Med 2017; 58:499-506.
71. Li X, Heber D, Leike T, Beitzke D, Lu X, Zhang X, et al. [68Ga]Pentixafor-PET/MRI for the detection of Chemokine receptor 4 expression in atherosclerotic plaques. Eur J Nucl Med Mol Imaging 2017.
72. Weiberg D, Thackeray J T, Daum G, Sohns J M, Kropf S, Wester H J, et al. Clinical Molecular Imaging of Chemokine Receptor CXCR4 Expression in Atherosclerotic Plaque using $^{68}$Ga-Pentixafor PET: Correlation with Cardiovascular Risk Factors and Calcified Plaque Burden. J Nucl Med 2017.
73. Bouter C, Meller B, Sahlmann C O, Staab W, Wester H J, Kropf S, et al. Imaging chemokine receptor CXCR4 in chronic infection of the bone with $^{68}$Ga-Pentixafor-PET/CT—first insights. J Nucl Med 2017.
74. Derlin T, Gueler F, Brasen J H, Schmitz J, Hartung D, Herrmann T R, et al. Integrating MRI and Chemokine Receptor CXCR4-Targeted PET for Detection of Leukocyte Infiltration in Complicated Urinary Tract Infections After Kidney Transplantation. J Nucl Med 2017; 58:1831-1837.
75. Schottelius M, Osl T, Poschenrieder A, Herrmann K, Lapa C, Hoffmann F, et al. [$^{177}$Lu]pentixather: preclinical and first patient results with a highly promising CXCR4-directed endoradiotherapeutic agent. Journal of Nuclear Medicine 2015; 56:339-339.
76. Habringer S, Lapa C, Herhaus P, Schottelius M, Istvanffy R, Steiger K, et al. Dual Targeting of Acute Leukemia and Supporting Niche by CXCR4-Directed Theranostics. Theranostics 2018; 8:369-383.
77. Herrmann K, Schottelius M, Lapa C, Osl T, Poschenrieder A, Haenscheid H, et al. First-in-man experience of CXCR4-directed endoradiotherapy with $^{177}$Lu- and $^{90}$Y-labelled pentixather in advanced stage multiple myeloma with extensive intra- and extramedullary disease. Journal of Nuclear Medicine 2015:jnumed. 115.167361.
78. Lapa C, Herrmann K, Schirbel A, Hanscheid H, Luckerath K, Schottelius M, et al. CXCR4-directed endoradiotherapy induces high response rates in extramedullary relapsed Multiple Myeloma. Theranostics 2017; 7:1589-1597.
79. Demmer O, Frank A O, Hagn F, Schottelius M, Marinelli L, Cosconati S, et al. A conformationally frozen peptoid boosts CXCR4 affinity and anti-HIV activity. Angew Chem Int Ed Engl 2012; 51:8110-8113.
80. Fang H Y, Munch N S, Schottelius M, Ingermann J, Liu H, Schauer M, et al. CXCR4 Is a Potential Target for Diagnostic PET/CT Imaging in Barrett's Dysplasia and Esophageal Adenocarcinoma. Clin Cancer Res 2018; 24:1048-1061.

The invention claimed is:
1. A compound of formula (Ib)

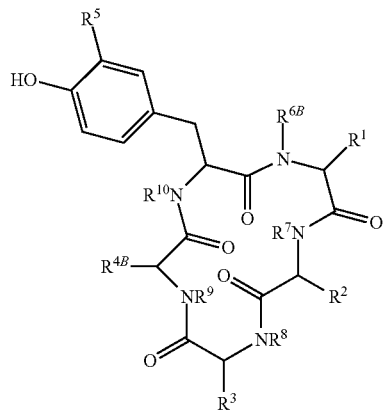

(Ib)

or a pharmaceutically acceptable salt thereof, wherein:
$R^1$ is alkyl;
$R^2$ is H or alkyl, which alkyl is optionally substituted with at least one substituent selected from —$NH_2$, —NH—C(=NH)—$NH_2$, —C(O)$NH_2$, —C(O)OH, —OH, —SH, —$SCH_3$ and a 5 to 10-membered carbocycle or 5 to 10-membered heterocycle containing oxygen, nitrogen or sulfur as heteroatom(s);
$R^3$ is H or alkyl, which alkyl is optionally substituted with at least one substituent selected from —$NH_2$, —NH—C(=NH)—$NH_2$, —C(O)$NH_2$, —C(O)OH, —OH, —SH, —$SCH_3$ and a 5 to 10-membered carbocycle or 5 to 10-membered heterocycle containing oxygen, nitrogen or sulfur as heteroatom(s);
$R^{4B}$ is alkyl substituted with one —$SR^A$;
$R^5$ is H or I;
$R^{6B}$ is alkyl substituted with one substituent selected from —$NH_2$, —NH—C(=NH)—$NH_2$, —NH—C(=NH)—NH—$R^{14}$, and —NH—C(=NH)—NH—C(=O)—$R^{15}$,
$R^7$ to $R^{10}$ are each independently H or alkyl;
$R^{14}$ and $R^{15}$ are independently C1-C10 alkyl, which alkyl is optionally substituted by at least one substituent selected from —NH—C(=O)—$CH_3$ and —C≡CH; and
$R^A$ is a group which comprises at least one selected from:
(i) a chelating moiety,
(ii) a chelate wherein a chelating moiety (i) is bound to a chelated radioactive or non-radioactive cation,
(iii) a phosphonate moiety, and
(iv) a fluorescent label.
2. The compound or salt of claim 1, wherein $R^1$ is a C1-C6 alkyl group.
3. The compound or salt of claim 1, wherein $R^2$ is C1-C6 alkyl, substituted with one group selected from —$NH_2$ and —NH—C(=NH)—$NH_2$.
4. The compound or salt of claim 1, wherein $R^3$ is methyl, substituted with a 5 to 10-membered carbocycle.
5. The compound or salt of claim 1, wherein $R^7$ to $R^{10}$ are H.
6. The compound or salt of claim 1, wherein $R^{4B}$ is C1-C6 alkyl substituted with one substituent —$SR^A$.
7. The compound or salt of claim 1, wherein $R^{6B}$ is -(linear C6 alkyl)-NH—C(=NH)—$NH_2$.
8. A pharmaceutical or diagnostic composition comprising a compound or salt of claim 1 and an excipient.
9. The compound or salt of claim 1, wherein $R^1$ is C1-C6 alkyl.
10. The compound or salt of claim 9, wherein $R^1$ is methyl.

* * * * *